US012788328B2

(12) United States Patent
Ong et al.

(10) Patent No.: US 12,788,328 B2
(45) Date of Patent: Nov. 10, 2026

(54) WIRELESS MEASUREMENT OF SUTURE TENSION

(71) Applicant: University of Oregon, Eugene, OR (US)

(72) Inventors: Keat Ghee Ong, Eugene, OR (US); Salil Sidharthan Karipott, Eugene, OR (US); Robert Erling Guldberg, Eugene, OR (US); Kaylee M. Meyers, Eugene, OR (US)

(73) Assignee: University of Oregon, Eugene, OR (US)

( * ) Notice: Subject to any disclaimer, the term of this patent is extended or adjusted under 35 U.S.C. 154(b) by 275 days.

(21) Appl. No.: 18/682,599

(22) PCT Filed: Aug. 9, 2022

(86) PCT No.: PCT/US2022/039799
§ 371 (c)(1),
(2) Date: Feb. 9, 2024

(87) PCT Pub. No.: WO2023/018693
PCT Pub. Date: Feb. 16, 2023

(65) Prior Publication Data

US 2025/0127457 A1 Apr. 24, 2025

Related U.S. Application Data

(60) Provisional application No. 63/347,122, filed on May 31, 2022, provisional application No. 63/231,102, filed on Aug. 9, 2021.

(51) Int. Cl.
*A61B 5/00* (2006.01)
*A61B 5/07* (2006.01)
(Continued)

(52) U.S. Cl.
CPC ............ *A61B 5/6883* (2013.01); *A61B 5/076* (2013.01); *A61B 5/4523* (2013.01); *A61B 5/486* (2013.01);
(Continued)

(58) Field of Classification Search
CPC ..... A61B 5/6883; A61B 5/076; A61B 5/4523; A61B 5/486; A61B 17/06166;
(Continued)

(56) References Cited

U.S. PATENT DOCUMENTS 3,805,601 A 4/1974 Jeffers
7,913,569 B2 3/2011 Girshovich et al.
(Continued)

FOREIGN PATENT DOCUMENTS

WO WO 2020/223207 11/2020

OTHER PUBLICATIONS

A Wireless Sensor for Real-Time Monitoring of Tensile Force on Sutured Wound Sites by DeRouin et al. (Year: 2016).*
(Continued)

*Primary Examiner* — Xin Y Zhong
(74) *Attorney, Agent, or Firm* — Husch Blackwell LLP; Bryan D. Stewart

(57) ABSTRACT

Certain examples of the disclosure concern an implantable sensor. The implantable sensor includes a sensor assembly configured to connect to a suture. The sensor assembly also includes a substrate and a resonant circuit coupled to the substrate. The resonant circuit is configured to electrically resonate at a resonant frequency when exposed to a first electromagnetic field and to emit a second remotely detectable electromagnetic field. The substrate is configured to deform in response to a tensile force applied by the suture and to change a resonant parameter of the resonant circuit in response to the deformation.

18 Claims, 23 Drawing Sheets

(51) Int. Cl.
*A61B 17/06* (2006.01)
*A61B 17/00* (2006.01)
*A61B 90/00* (2016.01)

(52) U.S. Cl.
CPC .................. *A61B 17/06166* (2013.01); *A61B 2017/00004* (2013.01); *A61B 2090/064* (2016.02); *A61B 2562/164* (2013.01)

(58) Field of Classification Search
CPC .... A61B 2017/00004; A61B 2090/064; A61B 2562/164; A61B 2017/0414; A61B 5/4533; A61B 5/4848; A61B 5/686; A61B 90/06; A61B 2017/0404; A61B 2017/0406; A61B 2017/044; A61B 2017/0445; A61B 17/0401; A61B 2560/0219; A61B 2562/0223; A61B 2562/0261; A61B 2562/028; A61B 2562/12; A61B 2562/166; A61B 5/0031
See application file for complete search history.

(56) References Cited

U.S. PATENT DOCUMENTS

| | | | | |
|---|---|---|---|---|
| 10,736,621 | B2 | 8/2020 | Zhao et al. | |
| 2008/0077016 | A1* | 3/2008 | Sparks | A61B 5/0031 600/459 |
| 2009/0299216 | A1* | 12/2009 | Chen | A61B 5/031 600/561 |
| 2014/0084943 | A1 | 3/2014 | Kroh et al. | |
| 2014/0228880 | A1 | 8/2014 | Bisson et al. | |
| 2017/0150886 | A1 | 6/2017 | Lin | |
| 2022/0401031 | A1* | 12/2022 | Ho | A61L 17/00 |

OTHER PUBLICATIONS

Arai et al., “The effect of flatfoot deformity and tendon loading on the work of friction measured in the posterior tibial tendon,” *Clinical Biomechanics* 22, pp. 592-598, 2007.
Bascuñan et al., “Large Animal Models for Anterior Cruciate Ligament Research,” *Frontiers in Veterinary Science*, vol. 6, Article 292, 12 pages, Aug. 2019.
Brosky et al., “The Ankle Ligaments: Consideration of Syndesmotic Injury and Implications for Rehabilitation,” *Journal of Orthopaedic & Sports Physical Therapy*, vol. 21, No. 4, 9 pages, Apr. 1995.
Chaudhury et al., “Tensile and shear mechanical properties of rotator cuff repair patches,” *Journal of Shoulder and Elbow Surgery*, vol. 21, pp. 1168-1176, 2012.
Davidson et al., “Rotator cuff repair tension as a determinant of functional outcome,” *Journal of Shoulder and Elbow Surgery*, vol. 9, No. 6, pp. 502-506.
Deprés-tremblay et al., “Rotator cuff repair: a review of surgical techniques, animal models, and new technologies under development,” *Journal of Shoulder and Elbow Surgery*, vol. 25, pp. 2078-2085, 2016.
Derouin et al., “A Wireless Sensor for Real-Time Monitoring of Tensile Force on Sutured Wound Sites,” *IEEE Transactions on Biomedical Engineering*, vol. 63, No. 8, pp. 1665-1671, Aug. 2016.
DeRouin et al., “A Wireless Inductive-Capacitive Resonant Circuit Sensor Array for Force Monitoring,” *Journal of Sensor Technology*, vol. 3, pp. 63-69, Sep. 2013.
DeRouin et al., “Development and Application of the Single-Spiral Inductive-Capacitive Resonant Circuit Sensor for Wireless, Real-Time Characterization of Moisture in Sand,” *Journal of Sensors*, vol. 2013, Article ID 894512, 7 pages, 2013.
Derwin et al., “Extracellular matrix scaffold devices for rotator cuff repair,” *Journal of Shoulder and Elbow Surgery*, vol. 19, pp. 467-476, 2010.
Dong et al., “Multi-Parameters Detection Implemented by LC Sensors With Branching Inductors,” *IEEE Sensors Journal*, vol. 19, No. 1, pp. 304-310, Jan. 1, 2019.
Ebramzadeh et al., “Biomechanical Comparison of Syndesmotic Injury Fixation Methods Using a Cadaveric Model,” *Foot and Ankle International*, vol. 34, No. 12, pp. 1710-1717, 2013.
Elliot et al., “Treatment of unfavourable results of flexor tendon surgery: Ruptured repairs, tethered repairs and pulley incompetence,” *Indian Journal of Plastic Surgery*, vol. 46, No. 3, pp. 458-471, Sep. 2013.
Evans et al., “Local deformation behavior of surface porous polyether-ether-ketone,” *Journal of the Mechanical Behavior of Biomedical Materials* 65, pp. 522-532, 2016.
Fleming et al., “In Vivo Measurement of Ligament/Tendon Strains and Forces: A Review,” *Annals of Biomedical Engineering*, vol. 32, No. 3, pp. 318-328, Mar. 2004.
Freedman et al., “Dynamic Loading and Tendon Healing Affect Multiscale Tendon Properties and ECM Stress Transmission,” *Scientific Reports*, www.nature.com/scientificreports, 13 pages, Jul. 18, 2018.
Gimbel et al., “The role of repair tension on tendon to bone healing is an animal model of chronic rotator cuff tears,” *Journal of Biomechanics* 40, pp. 561-568, 2007.
Godry et al., “Pullout strength and failure mode of industrially manufactured and self-made all-suture anchors: a biomechanical analysis,” *Journal of Shoulder and Elbow Surgery*, vol. 29, pp. 1479-1483, 2020.
Gornitzky et al., “Sport-Specific Yearly Risk and Incidence of Anterior Cruciate Ligament Tears in High School Athletes, A Systematic Review and Meta-analysis,” *The American Journal of Sports Medicine*, vol. 44, No. 10, pp. 2716-2723, 2016.
Hecker et al., “Pull-out strength of suture anchors for rotator cuff and Bankart lesion repairs,” *The American Journal of Sports Medicine*, vol. 21, No. 6, pp. 874-879, 1993.
Höer et al., “Miniaturized Sensors Registering the Long-Term Course of Suture Tension In Vivo under Varying Intra-Abdominal Pressure,” *Sensors*, vol. 18, 1729, 13 pages, 2018.
Horton et al., “A Varactor-Based, Inductively Coupled Wireless pH Sensor,” *Sensors*, vol. 11, No. 4, Apr. 2011, 6 pages.
Karipott et al., “An Embedded Wireless Temperature Sensor for Orthopedic Implants,” *Sensors*, vol. 18, No. 3, pp. 1265-1272, 2018.
Karipott et al., “Clinical potential of implantable wireless sensors for orthopedic treatments,” *Expert Review of Medical Devices*, 11 pages, 2018.
Kelly et al., “Fatigue behavior of As-built selective laser melted titanium scaffolds with sheet-based gyroid microarchitecture for bone tissue engineering,” *Acta Biomaterialia*, pp. 610-626, 2019.
Kim et al., “An in vitro study of individual ankle muscle actions on the center of pressure,” *Gait and Posture*, pp. 125-131, 2002.
Kim et al., “Clinical outcomes and repair integrity of arthroscopic rotator cuff repair using suture-bridge technique with or without medical tying: prospective comparative study,” *Journal of Orthopaedic Surgery and Research*, 8 pages, 2018.
Kjær et al., “Progressive early passive and active exercise therapy after surgical rotator cuff repair—study protocol for a randomized controlled trial (the CUT-N-MOVE trial),” *BMC*, 12 pages, 2018.
Ledet et al., “Smart implants in orthopedic surgery, improving patient outcomes: a review,” *Dove Press*, pp. 41-51, 2018.
Lewis et al., “Comparison of four alternative national universal anterior cruciate ligament injury prevention programme implementation strategies to reduce secondary future medical costs,” *Br J Sports Med.*, 7 pages, 2016.
Luque-Seron, et al., “Anterior Cruciate Ligament Strain In Vivo: A Systematic Review,” *Sports Health*, vol. 8, No. 5, pp. 451-455, 2016.
Mather et al., “The Societal and Economic Value of Rotator Cuff Repair,” *Journal of Bone and Joint Surgery, Inc.*, pp. 1993-2000, 2013.
Minagawa et al., “Prevalence of symptomatic and asymptomatic rotator cuff tears in the general population: From mass-screening in one village,” *Journal of Orthopaedics*, vol. 10, pp. 8-12, 2013.
Möller et al., “Acute rupture of tendo Achillis,” *Journal of Bone & Joint Surgery*, pp. 84308482000.

(56) References Cited

OTHER PUBLICATIONS

Naqvi et al., "Tightrope fixation of ankle syndesmosis injuries: Clinical outcome, complications and technique modification," *Injury*, vol. 43, pp. 838-842, 2012.
Neary et al., "Suture Button Fixation Versus Syndesmotic Screws in Supination-External Rotation Type 4 Injuries," *American Journal of Sports Medicine*, vol. 45, No. 1, pp. 210-217, 2017.
O'Connor et al., "Wireless Sensors for Smart Orthopedic Implants," *J Bio Tribo Corros*, 8 pages, 2017.
Ong et al., "Design and application of a wireless, passive, resonant-circuit environmental monitoring sensor," Sensors and Actuators, vol. A, No. 93, pp. 33-43, 2001.
Raschhofer et al., "Early active rehabilitation after arthroscopic rotator cuff repair: a prospective randomized pilot study," *Clinical Rehabilitation*, vol. 31, pp. 1332-1339, 2017.
Ravary et al., "Strain and force transducers used in human and veterinary tendon and ligament biomechanical studies," *Clinical Biomechanics*, vol. 19, pp. 433-447, 2004.
Samitier et al., "Failure of Anterior Cruciate Ligament Reconstruction," *Archives of Bone and Joint Surgery*, pp. 220-240, 2015.
Schachtrupp et al., "An implantable sensor device measuring suture tension dynamics: results of developmental and experimental work," *Hernia*, pp. 601-606, 2016.
Schachtrupp et al., "Influence of Elevated Intra-abdominal Pressure on Suture Tension Dynamics in a Porcine Model," *Journal of Surgical Research*, pp. 207-212, 2019.
Silbernagel et al., "Continued Sports Activity, Using a Pain-Monitoring Model, During Rehabilitation in Patients with Achilles Tendinopathy," *American Journal of Sports Medicine*, vol. 35, No. 6, pp. 897-906, 2007.
Slane et al., "The challenges of measuring in vivo knee collateral ligament strains using ultrasound," *Journal of Biomechanics*, vol. 61, pp. 258-262, 2017.
Thomopoulos et al., "Mechanisms of Tendon Injury and Repair," *Journal of Orthopaedic Research*, pp. 832-839, 2015.
Urch et al., Improved Rotator Cuff Footprint Contact Characteristics With an Augmented Repair Construct Using Lateral Edge Fixation, *American Journal of Sports Medicine*, vol. 48, No. 2, pp. 444-449, 2019.
Van der eng et al., "Rerupture Rate after Early Weightbearing in Operative Versus Conservative Treatment of Achilles Tendon Ruptures: A Meta-analysis," *Journal of Foot & Ankle Surgery*, vol. 52, pp. 622-628, 2013.
Van der list et al., "Arthroscopic Primary Anterior Cruciate Ligament Repair With Suture Augmentation," *Arthroscopy Techniques*, vol. 6, No. 5, pp. e1529-e1534, 2017.
Vand der Meijden et al., "Rehabilitation After Arthroscopic Rotator Cuff Repair: Current Concepts Review and Evidence-Based Guidelines," *International Journal of Sports Physical Therapy*, vol. 7, No. 2, pp. 197-218, 2012.
Willmott et al., "Outcome and complications of treatment of ankle diastasis with tightrope fixation," *Injury*, vol. 40, pp. 1204-1206, 2009.
Woo et al., "Functional Tissue Engineering of Ligament and Tendon Injuries," *Principles of Regenerative Medicine, Third Edition*, Ch. 67, p. 1179-1198, 2019.
Woo et al., "Biomechanics of knee ligaments: injury, healing, and repair," *Journal of Biomechanics*, vol. 39, pp. 1-20, 2006.
Woo et al., "The Importance of Controlled Passive Mobilization on Flexor Tendon Healing: A Biomechanical Study," *Acta Orthopaedica Scandinavica*, vol. 52, pp. 615-622, 1981.
Wylie et al., "A Comprehensive Evaluation of Factors Affecting Healing, Range of Motion, Strength, and Patient-Reported Outcomes After Arthroscopic Rotator Cuff Repair," *The Orthopaedic Journal of Sports Medicine*, vol. 6, No. 1, 7 pages, 2018.
Zhang et al., "A systematic review of suture-button versus syndesmotic screw in the treatment of distal tibiofibular syndesmosis injury," *BMC Musculoskeletal Disorders*, 12 pages, 2017.
Beeresha et al., "Design Optimization of Interdigital Capacitor," *International Journal of Research in Engineering and Technology*, vol. 5, Special Issue 21, pp. 73-78, 2016.
Wikipedia, "Gauge factor," https://en.wikipedia.org/wiki/Gauge_factor, 2 pages (accessed Jun. 2, 2021).
Wikipedia, "Strain gauge," https://en.wikipedia.org/wiki/Strain_gauge, 7 pages (accessed Jun. 9, 2021).
Wu et al., "Tendon injuries: basic science and new repair proposals," *EFFORT Open Reviews*, vol. 2, pp. 332-342, 2017.
Patel et al., "Epidemiology of sports-related musculoskeletal injuries in young athletes in United States," *Translational Pediatrics*, vol. 6, No. 3, pp. 160-166, 2017.
Barroso et al., "Muscle Injuries in Athletes," *Rev Bras Ortop.*, vol. 46, No. 4, pp. 354-358, 2011.
Kowalsky et al., "Evaluation of Suture Abrasion Against Rotator Cuff Tendon and Proximal Humerus Bone," *Arthroscopy: The Journal of Arthroscopic and Related Surgery*, vol. 24, No. 3, pp. 329-334, 2008.
Momose et al., "The Effect of Knot Location, Suture Material, and Suture Size on the Gliding Resistance of Flexor Tendons," *Biomed Mater Res*, vol. 53, pp. 806-811, 2000.
Lightsey et al., "Online Physical Therapy Protocol Quality, Variability, and Availability in Achilles Tendon Repair," *Foot & Ankle Specialist*, pp. 16-24, 2019.
Strom et al., "Achilles Tendon Rehabilitation," *Foot Ankle Clinic North America*, vol. 14, pp. 773-782, 2009.
Klosterhoff et al., "Implantable Sensors for Regenerative Medicine," *Journal of Biomechanical Engineering*, vol. 139, 11 pages, 2017.
Kiriyama et al., "A miniature tension sensor to measure surgical suture tension of deformable musculoskeletal tissues during joint motion," *Journal of Engineering in Medicine*, vol. 228, No. 2, pp. 140-148, 2014.
Kim et al., "Thin, Flexible Sensors and Actuators as "Instrumented" Surgical Sutures for Targeted Wound Monitoring and Therapy," *Small*, vol. 8, No. 21, pp. 3263-3268, 2012.
Liu et al., "Soft Elastomeric Capacitor for Strain and Stress Monitoring on Sutured Skin Tissues," *ACS Sensors*, vol. 6, pp. 3706-3714, 2021.
Dennis et al., "Suture materials—Current and emerging trends," *Journal of Biomed Mater Res Part A*, pp. 1544-1559, 2016.
Houshyar et al., "Multifunctional Sutures with Temperature Sensing and Infection Control," *Macromolecular Bioscience*, vol. 21, No. 3, 30 pages, 2021.
Saranya et al., "Review on next generation wireless power transmission technology for implantable biomedical devices," *Intl. J. Biomedical Engineering and Technology*, vol. 35, No. 3, pp. 207-222, 2021.
Zhao et al., "The recent advances in self-powered medical information sensors," *InfoMat.*, vol. 2, pp. 212-234, 2020.
Ferguson et al., "Wireless communication with implanted medical devices using the conductive properties of the body," *Expert Review of Medical Devices*, vol. 8, No. 4, 7 pages, 2011.
Haerinia et al., "Wireless Power Transfer Approaches for Medical Implants: A Review," *Signals*, vol. 1, pp. 209-229, 2020.
Teshome et al., "A Review of Implant Communication Technology in WBAN: Progress and Challenges," *IEEE Reviews in Biomedical Engineering*, vol. 12, pp. 88-99, 2019.
Bechir et al., "Planar inductor equivalent circuit model taking into account magnetic permeability, loss tangent, skin and proximity effects versus frequency," *Analog Intergr Circ Sig Process*, vol. 88, pp. 105-113, 2016.
Pinto et al., "Comparative failure analysis of PLA, PLA/GNP and PLA/CNTCOOH biodegradable nanocomposites thin films," *Procedia Engineering*, vol. 114, pp. 635-642, 2015.
Kharazi et al., "Quantifying mechanical loading and elastic strain energy of the human Achilles tendon during walking and running," *Scientific Reports*, vol. 11, 13 pages, 2021.
Escamilla et al., "Anterior Cruciate Ligament Strain and Tensile Forces for Weight-Bearing and Non-Weight-Bearing Exercises: A Guide to Exercise Selection," *Journal of Orthopaedic & Sports Physical Therapy*, vol. 42, No. 3, pp. 208-221, 2012.

(56) References Cited

OTHER PUBLICATIONS

Barrie et al., "The Role of Multiple Strands and Locking Sutures on Gap Formation of Flexor Tendon Repairs During Cyclical Loading," *Journal of Hand Surgery*, vol. 25A, No. 4, pp. 714-720, 2000.
International Search Report and Written Opinion for PCT/US2022/039799, dated Nov. 23, 2022 (24 pages).
International Preliminary Report on Patentability for PCT/US2022/039799, dated Feb. 13, 2024 (14 pages).
Meyer et al., "In vivo tendon force measurement of 2-week duration in sheep," *Journal of Biomechanics*, vol. 37, No. 1, pp. 135-140, Jan. 1, 2004.
Karipott et al., "A Wireless, Battery-Free Embedded Sensor for Monitoring Tension on a Suture Anchor," *IEEE Sensors Journal*, vol. 22, No. 2, pp. 1173-1179, Nov. 30, 2021.

* cited by examiner

WIRELESS MEASUREMENT OF SUTURE TENSION

CROSS REFERENCE TO RELATED APPLICATIONS

This is a U.S. National Stage application of PCT International Application No. PCT/US2022/039799, filed Aug. 9, 2022, which was published in English under PCT Article 21(2), which in turn claims the benefit of U.S. Provisional Application No. 63/347,122, filed May 31, 2022, and U.S. Provisional Application No. 63/231,102, filed Aug. 9, 2021, all of which are incorporated herein in their entirety.

ACKNOWLEDGMENT OF GOVERNMENT SUPPORT

This invention was made with government support under R43 AR078728 awarded by the National Institutes of Health. The government has certain rights in the invention.

FIELD

The present disclosure concerns examples of inductor-capacitor based sensors and related systems and methods for monitoring suture tension in a medical implant.

BACKGROUND

Tendon and ligament injuries are common complications in orthopedic and sports medicine. Tears to tendons and ligaments, many of which are treated surgically via suturing, require post-operative physical therapy to restore tissue structure and function. However, to effectively treat these injuries, the duration and intensity of rehabilitation need to be regulated to prevent tissue reinjury while promoting regeneration. Currently, physical therapy procedures following tendon and ligament repair rely on qualitative factors such as tissue swelling or patient pain tolerance, which can prevent optimal healing outcomes due to patient and medical caregiver variability.

Post-operative rehabilitation is important to achieve optimal functional restoration following orthopedic injuries. A typical rehabilitation process for a post-operation patient includes multiple stages that need trained physical therapists and/or surgeons to determine the patient's readiness to proceed to the subsequent stage. The evaluation process often relies on patient feedback, primarily focused on reported levels of pain and ability to conduct certain tasks. However, due to patient variability in anatomy and pain tolerance, the evaluation process is not consistent, which can lead to suboptimal healing or surgery failure. Thus, there is a need for improved apparatus, systems, and methods that provide non-intrusive, patient-specific, real-time, and quantitative biofeedback.

SUMMARY

Certain examples of the disclosure concern an implantable sensor. The implantable sensor includes a sensor assembly configured to connect to a suture. The sensor assembly also includes a substrate and a resonant circuit coupled to the substrate. The resonant circuit is configured to electrically resonate at a resonant frequency when exposed to a first electromagnetic field and to emit a second remotely detectable electromagnetic field. The substrate is configured to deform in response to a tensile force applied by the suture and to change a resonant parameter of the resonant circuit in response to the deformation.

Certain examples of the disclosure also concern an implantable sensor including an enclosure and a resonant circuit disposed inside the enclosure. The sensor is configured to connect to a suture. The resonant circuit includes at least one inductor and at least one capacitor. The resonant circuit has a resonant frequency determined at least by an inductance of the at least one inductor and a capacitance of the at least one capacitor. The enclosure is configured to deform in response to a tensile force applied by the suture. Deformation of the enclosure is configured to change the inductance of the at least one inductor and/or the capacitance of the at least one capacitor, thereby changing the resonant frequency of the resonant circuit.

Certain examples of the disclosure further concern an implantable sensor including an enclosure and a resonant circuit disposed inside the enclosure. The sensor is configured to connect to a suture. The resonant circuit includes at least one inductor, at least one capacitor, and a resistive transducer having a resistance that varies in response to the deformation. The resonant circuit has a resonance quality factor determined at least by an inductance of the at least one inductor, a capacitance of the at least one capacitor, and the resistance of the resistive transducer. The enclosure is configured to deform in response to a tensile force applied by the suture. Deformation of the enclosure is configured to deform the resistive transducer, thereby changing the resistance of the resistive transducer and the resonance quality factor of the resonant circuit.

Certain examples of the disclosure also concern an implantable sensor including a substrate and a resonant circuit connected to the substrate. The sensor is configured to connect to a suture. The resonant circuit includes at least one inductor, at least one capacitor, and a resistive transducer having a resistance that varies in response to the deformation. The resonant circuit has a resonance quality factor determined at least by an inductance of the at least one inductor, a capacitance of the at least one capacitor, and the resistance of the resistive transducer. The substrate is configured to deform in response to a tensile force applied by the suture. Deformation of the substrate is configured to deform the resistive transducer, thereby changing the resistance of the resistive transducer and the resonance quality factor of the resonant circuit.

Certain examples of the disclosure concern a device including a coil antenna configured to be placed over a body surface portion of the patient that is adjacent to a medical implant, and an impedance analyzer which is in electrical communication with the coil antenna. The impedance analyzer is configured to generate a first electromagnetic field that causes a resonant circuit of the medical implant to resonate at a resonant frequency and emit a second electromagnetic field. The impedance analyzer is further configured to detect the second electromagnetic field and measure a resonant parameter of the resonant circuit associated with a suture tension based on the detected second electromagnetic field.

Certain examples of the disclosure concern a system including a medical implant configured to be implanted inside a body of a patient, and a detector located outside the body of the patient. The medical implant includes a sensor and a suture connected to the sensor. The sensor includes a substrate and a resonant circuit coupled to the substrate. A tensile force applied by the suture is configured to cause a deformation of the substrate which changes a resonant parameter of the resonant circuit. The detector is configured to wirelessly detect the change of the resonant parameter and measure the tensile force applied by the suture based on the detected change of the resonant parameter.

Certain examples of the disclosure concern a method of fabricating an implantable sensor. The method includes coupling a resonant circuit to a substrate. The resonant circuit and the substrate can be any of the respective resonant circuits and substrates described above.

Certain examples of the disclosure also concern a method of assembling a detection device. The method includes connecting an impedance analyzer to a coil antenna. The impedance analyzer and the coil antenna can be any of the respective impedance analyzers and coil antennas described above.

Certain examples of the disclosure further concern a method including generating a first electromagnetic field with an interrogation source. The first electromagnetic field produces a resonance at a resonant frequency in a resonant circuit of a sensor wirelessly spaced apart from the interrogation source and causes the sensor to emit a second electromagnetic field. The sensor includes a substrate and the resonant circuit is coupled to the substrate. The substrate is configured to deform in response to a tensile force applied by a suture. The deformation of the substrate is configured to change a resonant parameter of the resonant circuit. The method further includes detecting the second electromagnetic field and measuring the resonant parameter of the resonant circuit based on the detected second electromagnetic field.

Certain examples of the disclosure also concern a system including a detector configured to wirelessly detect a change of resonant parameter of a resonant circuit and measure a tensile force applied to a suture based on the detected change of the resonant parameter. The resonant circuit is coupled to a substrate. The tensile force applied to the suture is configured to cause a deformation of the substrate which changes the resonant parameter of the resonant circuit.

Certain examples of the disclosure further concerns one or more computer-readable media having encoded thereon computer-executable instructions causing one or more processors to perform a method. The method includes generating a first electromagnetic field that causes a resonant circuit to resonate at a resonant frequency and emit a second electromagnetic field, detecting the second electromagnetic field, measuring a resonant parameter of the resonant circuit based on the detected second electromagnetic field, and converting the measured resonant parameter of the resonant circuit to a tensile force applied by a suture. The resonant circuit is coupled to a substrate. The substrate is configured to deform in response to the tensile force applied by the suture. The deformation of the substrate is configured to change the resonant parameter of the resonant circuit.

Certain examples of the disclosure concern an implantable, biodegradable pledget sensor, which can comprise: a sensing platform containing an electrical resonant circuit incorporated into a substrate body designed to be integrated with surgical sutures as a suture accessory, wherein the embedded resonant circuit undergoes electrical resonance at the intrinsic resonant frequency of the circuit when exposed to an electromagnetic field where resonant frequency can be remotely measured from an emitted secondary electromagnetic field. The sensor is configured to deform in response to suture loading, changing the electrical resonance characteristics of the circuit where these measured alterations in resonance behavior are then correlated to changes in suture loading behavior in real-time. The sensor can utilize conductive suture material to assist in signal coupling and sensor functionality. The implanted sensor can be configured to degrade partially or fully within the body after its functional lifetime is complete.

In some examples, the resonant circuit comprises at least one inductive, capacitive, and resistive constituent, including both deliberates and parasitics, that determine electrical resonant behavior. For example, parasitic capacitance and deliberate inductor can be used to form resonant circuit, deliberate capacitor and deliberate inductor can be used to form resonant circuit, etc.

In some examples, deformation of the sensor substrate body can comprise bending of any portion of the sensor substrate.

In some examples, deformation of the sensor substrate body can comprise elongation of any portion of the sensor substrate.

In some examples, deformation of the sensor substrate body can comprise flexion of any portion of the sensor substrate.

In some examples, deformation of the sensor substrate body can comprise compression of any portion of the sensor substrate.

In some examples, the sensor substrate body shape can be altered to influence deformation behavior and therefore sensitivity and detection ranges of the circuit. For example, the sensor can have rectangular/box sensor body outline or rounded sensor body outline shapes.

In some examples, the sensor substrate body geometry can be altered to influence deformation behavior and therefore sensitivity and detection ranges of the circuit. For example, the width or height of the sensor body legs can be changed to alter sensor body deformation (e.g., taller legs allow more flexion to occur, thicker legs allow less flexion to occur).

In some examples, the sensor substrate body aspect ratio can be altered to influence deformation behavior and therefore sensitivity and detection ranges of the circuit. For example, the ratio between the length and width of the sensor body can be changed to alter sensor body deformation (e.g., increased sensor body length and decreased sensor body width allows more flexion to occur).

In some examples, the sensor substrate body feature thicknesses can be altered to influence deformation behavior and therefore sensitivity and detection ranges of the circuit. For example, the thickness of sensor body sheet/membrane can be changed to alter sensor body deformation (e.g., thicker sheet/membrane allows for less flexion to occur).

In some examples, the sensor substrate body feature spacing can be altered to influence deformation behavior and therefore sensitivity and detection ranges of the circuit. For example, the distance between sensor body holes (e.g., holes in which suture pass through) can be changed to alter sensor body deformation (e.g., decreasing space between holes increases sensor flexion by concentrating the load on the sensor body).

In some examples, the sensor substrate body material can be altered to influence deformation behavior and therefore sensitivity and detection ranges of the circuit. For example, the stiffness of the sensor body can be changed by using a different material or composite/copolymer composition (e.g., a stiffer sensor body material will decrease sensor body deformation).

In some examples, the sensor substrate body orientation relative to suture direction can be altered to influence deformation behavior and therefore sensitivity and detection ranges of the circuit. For example, different faces (e.g., top, bottom, sides) of the sensor body can be selected for the surgical sutures to pass through.

In some examples, deformation of the sensor can be configured to change the inductive element(s) of the circuit to alter resonant behavior.

In some examples, deformation of the sensor can be configured to change the capacitive element(s) of the circuit to alter resonant behavior.

In some examples, deformation of the sensor can be configured to change the resistive element(s) of the circuit to alter resonant behavior.

In some examples, deformation of the sensor can be configured to bring the resonant circuit in proximity to a secondary conductive element to alter resonant behavior. For example, the resonant behavior of the resonant circuit can be altered in a distance or proximity dependent fashion in the presence of a conductive material. In some examples, this principle can be used to transduce suture loading force in the sensor design. As another example, referring to the pledget sensor depicted in FIGS. 15A-15B and described below, the spiral conductive pattern can be embedded in the top layer (also referred to as bending layer) of the sensor, while a conductive layer can be embedded in the bottom layer. As the top layer moves closer to the bottom layer due to tensile pulling from the suture, the inductance and capacitance of the top conductive pattern can change due to the changes in electromagnetic coupling with the bottom conductive layer. Compared to the single conductor pattern design, this configuration can result in larger changes in the sensor resonance for the same suture tension. In some examples, the secondary conductive element can be made of conductive materials such as zinc, magnesium, iron and their alloys, semiconductors, or magnetic materials such as iron oxides. Example alloys include magnesium-calcium alloy, magnesium-yttrium-neodymium-zirconium alloy (or WE43 alloys), iron-manganese-palladium-carbon alloy (or Fe—Mn—Pd alloy), etc.

In some examples, two spiral conductive patterns of slightly different designs and resonant frequencies can be embedded in the top and bottom layers of the sensor, respectively. The spiral directions of these two spiral conductive patterns can be the same or opposite to each other. As the top layer bends towards the bottom layer, the mutual inductance coupling between the two spirals conductive patterns can affect the resonant frequencies of both spiral conductive patterns, allowing measuring the suture loading force.

In some examples, the inductive constituent comprises a planar coil or parasitic inductor.

In some examples, the capacitive constituent comprises an interdigital, parallel plate, or parasitic capacitor.

In some examples, the resistive constituent comprises a resistive transducer or parasitic resistor, including the conductive suture material(s) as a strain-sensing element. For example, as the conductive suture material is loaded in tension, its resistance can change. In some examples, this principle can be utilized with the resonant circuit to function as strain-sensing element to transduce suture loading in the senor design.

In some examples, multiple resonant circuits can be used with different resonant frequencies to improve sensor performance. For example, the baseline or starting resonant behavior and resonant frequency of the sensor can be tailored by altering initial inductive, capacitive, or resistive values of the equivalent circuit. In some examples, one resonant circuit can transduce/sense suture loading while another resonant circuit with a different resonant frequency can be used to account for alterations in environmental conditions such as changes in body temperature. Mutual coupling between the two resonant circuits can be reduced, e.g., by placing the secondary resonant circuit (for sensing environmental conditions) at least a predefined distance away from the first resonant circuit (for load-sensing) to prevent cross-talks.

In some examples, multiple inductor coils can be stacked within a bending layer of the sensor to improve signal transmission ranges. For example, assembling or stacking or packing multiple inductors within the senor body can be used to increase signal transmission.

In some examples, the inductive and capacitive constituents can be placed in series configurations. For example, one or more deliberate inductor(s) and deliberate capacitor(s) can be placed in series.

In some examples, the inductive and capacitive constituents can be placed in parallel configurations. For example, one or more deliberate inductor(s) and deliberate capacitor (s) can be placed in parallel.

In some examples, the resonant parameter of the resonant circuit comprises resonant frequency of the resonant circuit.

In some examples, the resonant parameter of the resonant circuit comprises resonant quality factor of the resonant circuit.

In some examples, the resonant parameter of the resonant circuit comprises real impedance magnitude of the resonant circuit.

In some examples, the substrate body comprises a biocompatible material that fully encloses and isolates the resonant circuit(s). For example, the resonant circuit can be electrically isolated from the body for its functional lifetime to operate properly. Example insulation materials can include polymeric materials, such as polylactic acid, polyglycolic acid, polycaprolactone, and their copolymer combinations.

In some examples, the substrate body can include an enclosure to further isolate sensor from implantation environment. For example, an enclosure could encase sensor substrate body to prevent tissue from interfering with sensor bending function.

In some examples, the sensor can have an enclosure design to prevent contact damage with surrounding tissue(s). For example, the sensor can have a softer outer enclosure configured to protect delicate surrounding tissues from ripping, cutting, or tearing damage the enclosed sensor body could cause. Examples of soft outer enclosure materials include meshes of polylactic acid, polyglycolic acid or polycaprolactone and their copolymer combinations, etc.

In some examples, the substrate body material can be partially or fully biodegradable by using bioresorbable polymers. Examples of bioresorbable polymers include polylactic acid, polyglycolic acid or polycaprolactone and their copolymer combinations.

In some examples, the resonant circuit constituents can be partially or fully biodegradable by using bioresorbable metals and polymers. Examples of bioresorbable metals include zinc, magnesium, the combination of zinc and magnesium, and certain alloys, etc.

In some examples, degradation rates of the metal constituents of the device can be controlled by altering alloying composition ratios.

In some examples, degradation rates of the polymer constituents of the device can be controlled by altering copolymer composition ratios and polymer molecular weight.

In some examples, degradation rates of the polymer constituents of the device can be controlled by using polymer that is heat sensitive. For example, focused ultrasound can be used to accelerate the degradation of the polymer at any time after implantation.

In some examples, the sutures utilized with the sensor can be rendered conductive to facilitate sensor performance. For example, conductive polymers can be used to make suture conductive. Examples of conductive polymers includes polyaniline, polypyrrole, poly(3,4-ethylenedioxythiophene) polystyrene sulfonate, etc.

In some examples, a conductive element can be integrated into current suture design via a coating. For example, a suture can be dip coated in a conductive polymer solution. As another example, a suture can be plasma treated or chemically functionalized to bind a conductive polymer.

In some examples, a conductive element can be integrated into current suture design via braiding of a conductive material. For example, a surgical suture or surgical suture strand can be wrapped or braided with another surgical suture that has been rendered conductive.

In some examples, a conductive element can be integrated into current suture design via a secondary material attachment during primary surgical stitching. For example, as a surgical suture is being passed through tissue, another surgical suture that has been rendered conductive and is electrically coupled to the resonant circuit can be placed or integrated within the loops of the primary surgical suture pattern.

In some examples, the conductive suture can be configured as an antenna to increase signal coupling and transmission depth. For example, the suture can act as an antenna for the resonant circuit.

In some examples, the sensing platform can be utilized with absorbable and nonabsorbable suture types. Examples of absorbable sutures include poly(lactic-co-glycolic acid) sutures, etc. Examples of nonabsorbable sutures include polyamide, polypropylene, polyester sutures, etc.

In some examples, the sensing platform can be used with continuous or interrupted forms of any suture pattern. Examples of suture patterns with interrupted and continuous configurations include horizontal mattress sutures, subcuticular sutures, vertical mattress sutures, etc.

In some examples, physical and/or chemical affixation methods can be used to couple the sensor substrate body containing the resonant circuit to surgical sutures. Examples of physical methods include clamping, clipping, tying, etc. Examples of chemical methods include adhesive surgical glue, etc.

In some examples, the sensors can be configured to improve sensor visualization intra and post operatively. For example, the sensor body color can be configured to be allow easy identification during surgery. In certain cases, radiopaque additives (e.g., barium sulfate) can be incorporated into the sensor body material to make the sensor body visible with standard x-ray procedures.

Certain aspects of the disclosure concern methods to compensate for sensor substrate plastic deformation. For example, after the sensor is fully fabricated and assembled, an increased prestress (e.g., 200% percent of the maximum load specification of the sensor) can be applied so that plastic deformation effects in the sensor loading range can be minimized (loading on the sensor stays in the elastic deformation range of the material). As another example, running calibration curves with the sensor can be used to identify and account for effects of plastic deformation when taking sensor readings.

Certain aspects of the disclosure concern methods to compensate for implanted environmental conditions. For example, running calibration curves with the sensor can be used to identify and account for effects of variation in body temperature when taking sensor readings. As another example, running calibration curves with the sensor can be used to identify and account for effects of variation in body tissue thickness above sensor when taking sensor readings. In some examples, a secondary, independent resonant circuit can be incorporated within the sensing system.

Certain aspects of the disclosure concern methods to compensate for effects of the type of tissue being sutured. For example, running calibration curves with the sensor can be used to identify and account for effects of variation in body tissue types around sensor when taking sensor readings (e.g., suturing in a soft tissue like a muscle versus a stiffer tissue like a ligament can create variations sensor deformation and therefore sensor readings).

Certain aspects of the disclosure concern methods of fabricating and assembling sensor substrate body. For example, the sensor substrate body can be created by means of 3D printing or injection molding.

Certain aspects of the disclosure concern methods of fabricating and assembling resonant circuit(s). For example, the resonant circuit traces and constituents can be printed by photolithography or similar printing techniques.

Certain aspects of the disclosure concern a detection device comprising: an external antenna coil configured to be placed superficially to the implanted sensor, and an impedance analyzer (e.g., a vector network analyzer) electrically connected to the external antenna coil. The impedance analyzer can be configured to produce a primary electromagnetic field to cause the implanted resonant circuit to resonate and emit a secondary electromagnetic field containing resonant parameters associated with suture loading that can be measured with the impedance analyzer.

In some examples, the detection device can have a single detection coil system where a single coil is responsible for both excitation and detection. For example, the single coil can receive electrical current from the electronics. Sensor response can alter the reflected voltage to the coil. The change in the reflected voltage, measured as a function of frequency, can be used to determine the resonance characteristics of the sensor.

In some examples, the detection device can have a dual detection coil system where one coil is used for excitation and another coil is used for detection. In certain circumstances, having one coil for excitation and another coil for detection can improve signal detection ranges of the sensor.

In some examples, the external detection and excitation system (e.g., the detection device) can be incorporated into a brace-like device worn by the patient with the implanted sensor. For example, electronics can be embedded in an ankle brace, a knee brace, a wrist brace, ab elbow brace, etc.

In some examples, a microcontroller can be connected to the impedance analyzer can mediate excitation signal frequency sweeps to detect resonant parameters.

In some examples, the microcontroller can collect raw data of the emitted secondary electromagnetic field measured by the impedance analyzer.

In some examples, a computer or mobile device can be used for patient and healthcare professional interfacing with the detection device.

In some examples, the computer or mobile device can be configured to wirelessly control the microcontroller and therefore the entirety of the detection device remotely.

In some examples, the computer or mobile device can be configured to receive raw resonant parameter data from the microcontroller remotely.

In some examples, the computer or mobile device can be configured to utilize signal postprocessing methods and software to translate raw resonant parameter data into measured suture loading force in a form that is easily understood by the designated user. In some examples, the software can be configured to compare raw resonant parameter data with a suture loading calibration curve to determine suture loading force.

Certain aspects of the disclosure concern methods to increase detection distance through modifications to the design of the external detection system. For example, excitation/detection coil size, shape, and/or material can be altered to increase detection distance.

The foregoing and other objects, features, and advantages of the disclosed technologies will become more apparent from the following detailed description, which proceeds with reference to the accompanying figures.

DETAILED DESCRIPTION

General Considerations

Figure 1:
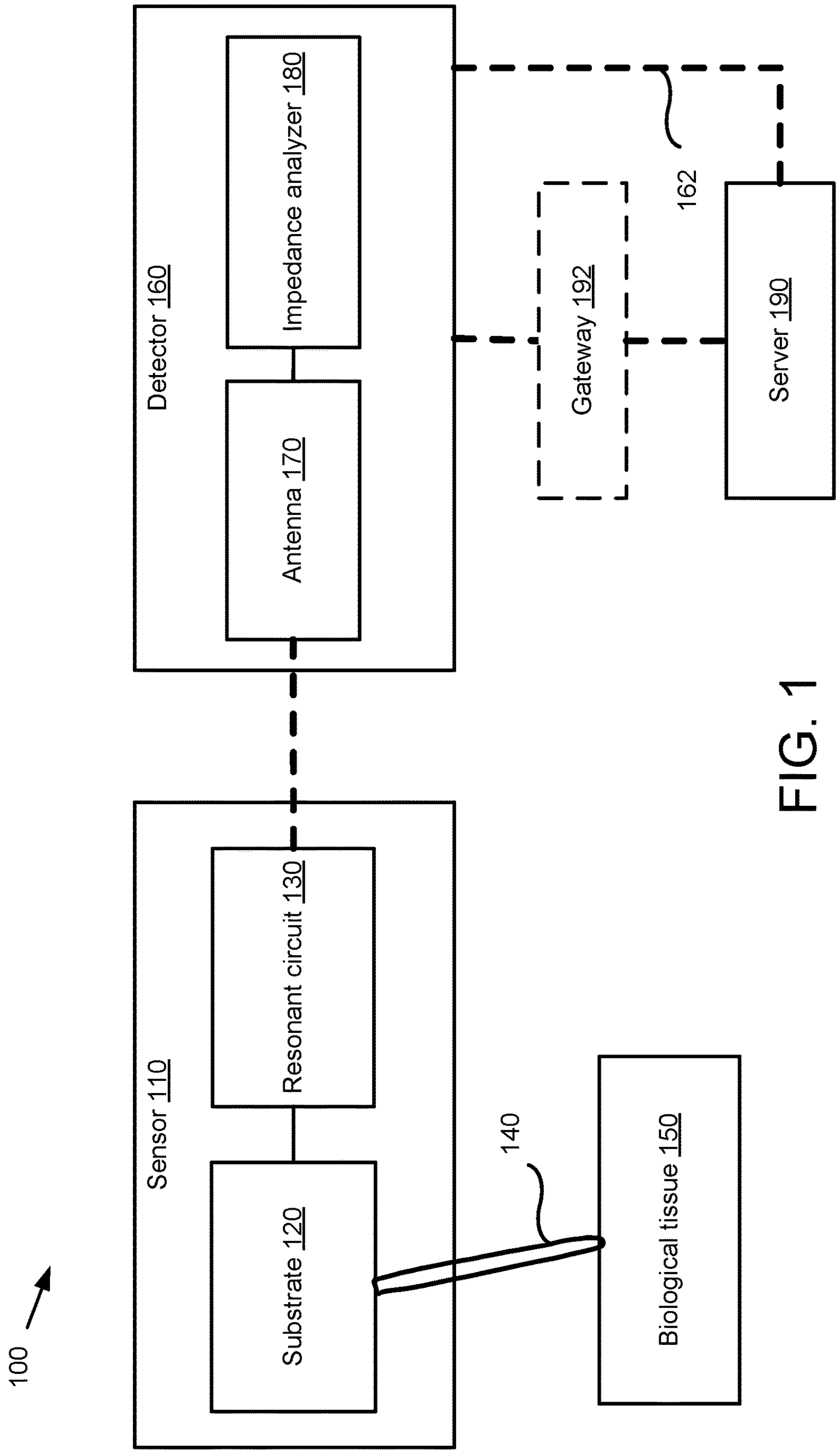
FIG. 1 is a block diagram depicting an example system for detecting a tensile force applied to a suture.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed examples, alone and in various combinations and sub-combinations with one another. The methods, apparatus, and systems are not limited to any specific aspect or feature or combination thereof, nor do the disclosed examples require that any one or more specific advantages be present or problems be solved. The technologies from any example can be combined with the technologies described in any one or more of the other examples. In view of the many possible examples to which the principles of the disclosed technology may be applied, it should be recognized that the illustrated examples are only preferred examples and should not be taken as limiting the scope of the disclosed technology.

Although the operations of some of the disclosed examples are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "connected" generally mean electrically, electromagnetically, and/or physically (e.g., mechanically or chemically) coupled or linked and does not exclude the presence of intermediate elements between the coupled or associated items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated examples. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or," as well as "and" and "or."

As used herein, the term "approximately" and "about" means the listed value and any value that is within 20% of the listed value. For example, "about 1" means any value between about 0.8 and about 1.2, inclusive.

Post-Operative Rehabilitation Monitoring

General Overview

The number of soft tissue injuries, many of which require surgical interventions for recovery, has steadily increased in the past few decades. In most cases, the success of surgical interventions for these injuries is primarily contingent upon the mechanical stability of the injury site during the healing process. Thus, postoperative monitoring of tensile loading in soft tissue injuries is useful for assessing tissue healing, as well as providing new insights for refining surgical intervention techniques and detecting implant failure. However, although surgeons can measure and control the tensile force applied to soft tissue during the surgery, there is a lack of practical technique to continue the measurement afterward. This creates a challenge for surgeons to properly assess the conditions of the implant post-surgery to administer personalized and evidence-based rehabilitation therapy.

A typical rehabilitation process for a post-operation patient includes multiple stages that need trained physical therapists and/or surgeons to determine the patient's readiness to proceed to the subsequent stage. A typical orthopedic surgery may require the patient to spend a significant recovery time prior to resuming normal activities with cautions. Standard post-surgery care often relies on patient feedback, primarily focused on self-reported levels of pain and ability to conduct certain tasks. This could lead to significant over or underestimations of patient readiness due to the variability in patient's pain tolerance and communication errors. For example, without a quantitative evaluation tool to provide biofeedback during the rehabilitation process, health care providers have no choice but to use a conservative approach, unnecessarily delaying the healing process which leads to more physical therapy sessions (thus added healthcare cost), added wage loss, and less than optimal healing outcomes. On the other hand, there are situations where the healthcare provider misjudges the healing progress of patients and prescribes over-aggressive treatment, leading to reinjury of the soft tissue.

The technology described herein can provide quantitative data to precisely gauge the state of healing, allowing healthier patients to resume normal activities faster while preventing re-injuries for patients with slower recovery.

More specifically, the disclosed technology is based on an implantable sensor configured to measure a tension force in a suture (also referred to as "suture tension") which is used to anchor the soft tissue. For soft tissue injuries such as tendon and ligament tears, a general surgical treatment approach is to suture the torn tissues to a device (e.g., a suture button or a suture anchor) that is anchored into a bone. Since the suture is connected to the torn or damaged soft tissues, the mechanical environment of the injury site can be quantified by measuring the tensile force in the suture. A number of studies have indicated that suture techniques affect clinical outcome of orthopedic repairs, suggesting that functional suture strains during recovery play an important role in post-operative healing and failure rates. Moreover, many studies have demonstrated the effects of dynamic loading on tendon healing. Thus, measurement of suture tension can be used as a biofeedback indicator of post-operative healing status.

As described more fully below, the implantable sensor includes a substrate and a resonant circuit coupled to the substrate. A tensile force applied by the suture can be configured to cause a deformation of the substrate which changes a resonant parameter (e.g., a resonant frequency and/or a resonance quality factor) of the resonant circuit. As described herein, deformation of the substrate can include elongation, compression, bending, torsion, displacement, and/or other changes to the form and/or shape of at least a portion of the substrate. A detector outside the patient can be configured to wirelessly detect the change of the resonant parameter and measure the tensile force applied by the suture based on the detected change of the resonant parameter.

Post-Operative Monitoring of Tendon/Ligament Repair

Within the United States, there are over 16 million tendon and ligament injuries a year. These complications are particularly prevalent in physically active populations, such as professional and recreational athletes, due to over-use with repetitive motion or traumatic accidents. When surgical intervention is required to facilitate tendon and ligament repair, non-absorbable sutures (polyamide, polyester, polyethylene, and polypropylene-based) are typically utilized to treat partially or fully torn tissues. After surgery, early mobilization is vital to restoring tissue strength, but there is always risk of suture breakage and re-rupture of the tissue. Therefore, during this recovery period, physical therapy regimes are typically performed for 4-12 weeks following surgery. Modern physical therapy guidelines for the duration and intensity of rehabilitation sessions are largely inconsistent and rely on qualitative factors such as tissue swelling or patient pain tolerance. Medical imaging techniques including ultrasound, magnetic resonance imaging, and computed tomography can provide some indication of wound healing status but cannot fully capture tissue loading with dynamic patient movements required during physical therapy sessions. A tool that could monitor real-time suture conditions, such as loading during rehabilitation exercises, could aid physical therapists in making better informed treatment decisions, allowing patients to return to normal physical activities more safely and quickly.

One approach to accomplishing this task includes sensitizing suture accessories (e.g., pledgets, buttons, anchors, etc.) to evaluate the local healing environment and suture status. Some examples of sensitized suture devices have been developed in laboratories for temperature, pressure, tension, pH, and bacteria monitoring. These sensing platforms may perform well in benchtop settings but often fail to be translated into the clinic due to battery or transcutaneous wire connection requirements for power supply and data transmission, limiting their applications to superficial skin wounds where there is less need due to the convenience of visual assessment. Additionally, implanted sensors that require wire connections increase the potential for infection and produce noise artifacts associated with wire movement while implementing batteries in implantable sensor designs can also be detrimental to device functionality and tissue healing due to increased size demands, decreased platform lifetime, accidental toxic leakage, and heat generation.

The technology disclosed herein involves a passive inductor-capacitor (LC) based biosensor that allows remote transfer of data and power via electromagnetic coupling. Specifically, one of the designs for this technology consists of a single resonant element such as a spiral inductor. Due to the parasitic capacitance and resistance among conductor traces, a planar, spiral printed inductor forms a resonance circuit that undergoes electrical resonance when the impedances of the capacitive and inductive constituents of the circuit are equal. Since capacitance and inductance are frequency-dependent, this phenomenon occurs at a specific frequency, which is the intrinsic resonance frequency of the circuit. Any modifications to the capacitance or inductance of the circuit will result in a change in the circuit's measured resonance frequency which can be detected wirelessly via electromagnetic coupling. One method to altering the resonance behavior of the circuit in this study includes flexion of the planar inductor coil pattern. In this case, a suture pledget with an embedded LC resonant circuit is designed to bend in response to suture loading, changing the electrical resonance characteristics of the circuit. These measured alterations in resonance behavior can then be correlated to changes in suture loading magnitude.

In order to increase the utility of suture sensors in a clinical environment, a passive, remotely operated sensing platform is developed that could measure suture loading force. The platform includes an implantable pledget sensor and an external communication system that provided inductive coupling for signal and power transmission. Suture force sensing can be based on deformation of pledgets containing the LC resonant circuit pattern with applied loading. This sensor design is advantageous to fabrication with fully bioresorbable materials to enable future iterations of the device to degrade within the body, eliminating the need for surgical removal. To engineer pledget sensors with desired load range and sensitivity, finite element analysis (FEA) and imaging techniques were first utilized to evaluate pledget sensor under different loading conditions. Following the fabrication of the pledget sensors, mechanical testing studies were then implemented to characterize the sensitivity and repeatability of the sensing platform over multiple loading cycles. Tissue mimics were also used to test signal transmission depth ranges of the pledget sensor. Overall, preliminary studies have demonstrated basic functionality of a wireless suture pledget sensing device that could enable physical therapists to better monitor tendon and ligament loading and healing during rehabilitation sessions.

Alternative Implementations of Disclosed Technologies

Although sutures are described in various examples below, it is to be understood that the disclosed technology can be configured to measure a tensile force applied by a biological tissue without a suture. For example, in certain examples, a surgery can be performed that directly connects a tendon or ligament to the implantable sensor, instead of using a suture as an intermediary to connect the tendon or ligament to the implantable sensor. In such circumstances, instead of measuring the suture tension, the disclosed technology can directly measure the tension in the tendon or ligament, according to the same principles described herein.

Although specific implantable sensors with specific structural and/or electrical components are described below as representative examples, it should be understood that the same principles described herein can also be applied to many implantable sensors having different structural and/or electrical components. Despite such differences, these implantable sensors share certain commonalities. For example, they are all battery-less, and each includes at least one resonant circuit attached to at least one deformable substrate such that deformation of the substrate causes a change of resonant parameter of the resonant circuit. Likewise, although a specific circuit design for a detector and specific wearable configurations for affixing the detector to a body part based on specific orthopedic surgeries are described below as representative examples, it should be understood that, according to the same principles described herein, the detector can have a different circuit design and/or other structural configurations configured for post-operative monitoring of different types of orthopedic surgeries.

Example Overall System for Tensile Force Measurement in Surgical Sutures

FIG. 1 is a block diagram depicting an example system 100 for detecting a tensile force applied to a suture 140, which is connected to a biological tissue 150 (e.g., a tendon, ligaments, a muscle, etc.) of a patient.

As described herein, the suture 140 can be made of natural and/or synthetic materials. Example suture materials include silk, cotton, linen, nylon, steel, carbon fiber, polypropylene, polybutester, polyethylene, etc. As described herein, the patient can be a person or an animal.

The system 100 includes a sensor 110 which can be implanted inside a patient's body and a detector 160 (also referred to as an "interrogation source") which is located outside the body of the patient.

As shown, the sensor 110 includes a substrate 120 and a resonant circuit 130 connected to the substrate 120. As described more fully below, the resonant circuit 130 can be configured to electrically resonate at a resonant frequency when exposed to an excitation electromagnetic field and to emit a secondary, remotely detectable electromagnetic field. The substrate 120 can be configured to deform in response to a tensile force applied by the suture 140 and to change a resonant parameter of the resonant circuit 130 in response to the deformation.

As shown, the detector 160 includes an antenna 170 (such as a coil antenna) and an impedance analyzer 180 which is in electrical communication with the antenna 170. The antenna 170 can be configured to be placed over a body surface portion of the patient that is adjacent to the implanted sensor 110. The impedance analyzer 180 can be configured to generate the excitation electromagnetic field that causes the resonant circuit 130 of the sensor 110 to resonate at a resonant frequency and emit the secondary electromagnetic field. While generating the excitation field, the impedance analyzer 180 can also measure the electrical impedance of the antenna 170. Any secondary electromagnetic field generated by the sensor's resonant circuit 130 can affect the electrical impedance of the antenna 170. Thus, based on measurement of the impedance of the antenna 170, the detector 160 can measure a resonant parameter of the resonant circuit 130 associated with a tensile force applied to the suture 140 (e.g., by the biological tissue 150).

Based on the measured resonant parameter, the detector 160 can be configured to calculate the tension force applied to the suture 140, thus evaluating the mechanical properties or healing status of the biological tissue 150. In certain examples, the detector 160 can save and/or output the calculated tension force applied to the suture 140 in reatime. In certain examples, the detector 160 can be configured to monitor the tensile force applied to the suture 140 over a period of time (e.g., a week, a month, etc.), thus providing a way to longitudinally track the rehabilitation status of the patient.

In certain embodiments, the detector 160 can be configured to wirelessly communicate with multiple sensors 110 implanted in the body of the patient. For example, the patient may have multiple sutures 140, each of which is connected to a respective biological tissue 150. Each suture 140 can be connected to a respective sensor 110. The resonant circuits 130 in the sensors 110 can have different resonant frequencies when exposed to the excitation electromagnetic field generated by the detector 160. Thus, by analyzing the impedance spectra of these sensors 110, the detector 160 can be configured to simultaneously measure resonant parameters of resonant circuits 130 in multiple sensors 110. As such, the detector 160 can measure the tensile force applied to each of the sutures 140, thus allowing quantitative evaluation of the healing status of multiple biological tissues 150.

In certain examples, the system 100 can also include a server or server station 190 (e.g., a secured computer, a smartphone with secured cloud data storage that physicians can access to, etc.), which can be configured to establish wireless communication with the detector 160. In certain embodiments, the detector 160 can wirelessly communicate with the server 190 without any intermediary devices, as indicated by the dashed line 162. In other embodiments, the detector 160 can wireless communicate with the server 190 via one or more local-area gateway devices 192 (e.g., routers and/or modems). Such local-area gateway devices 192 can operate between the detector 160 and the server 190 in a repeater configuration. For example, the local-area gateway devices 192 can listen to the detector 160, receive data packets from the detector 160, and retransmit the packets to the server 190. In certain examples, the server 190 can transmit control data (e.g., acknowledgement to receipt of data package, commands and/or parameters for changing detector configurations, etc.) to the detector 160, either directly or via the one or more local-area gateway devices 192. Various known or to-be-developed wireless communication protocols can be used for communication between the detector 160 and the server 190, between the detector 160 and the gateway devices 192, and between the gateway devices 192 and the server 190.

Data communication between the detector 160 and the server 190 can be periodic (e.g., every second, every minute, every hour, every day, etc.), or on-demand, or even-triggered (e.g., upon detection that a suture tension exceeds a predetermined threshold). Thus, the server 190 can remotely aggregate (and log) the patient's sensor data (e.g., suture tension) measured by the detector 160. A physician can log into an application interfacing with the server 190 and access the patient's sensor data. Thus, the system 100 allows the physician to remotely monitor the patient's post-operative rehabilitation status.

In certain embodiments, the server 190 can be configured to wirelessly communicate with multiple detectors 160, each of which is configured to wirelessly measure the tensile force in a suture connected to a sensor 110 implanted in a patient. Thus, the system 100 described herein can be configured to support remote monitoring the post-operative rehabilitation status of multiple patients, each having one or more implanted sensors 110 and a corresponding detector 160.

Example Overall Method of Measuring Tensile Force in Surgical Sutures

Figure 2:
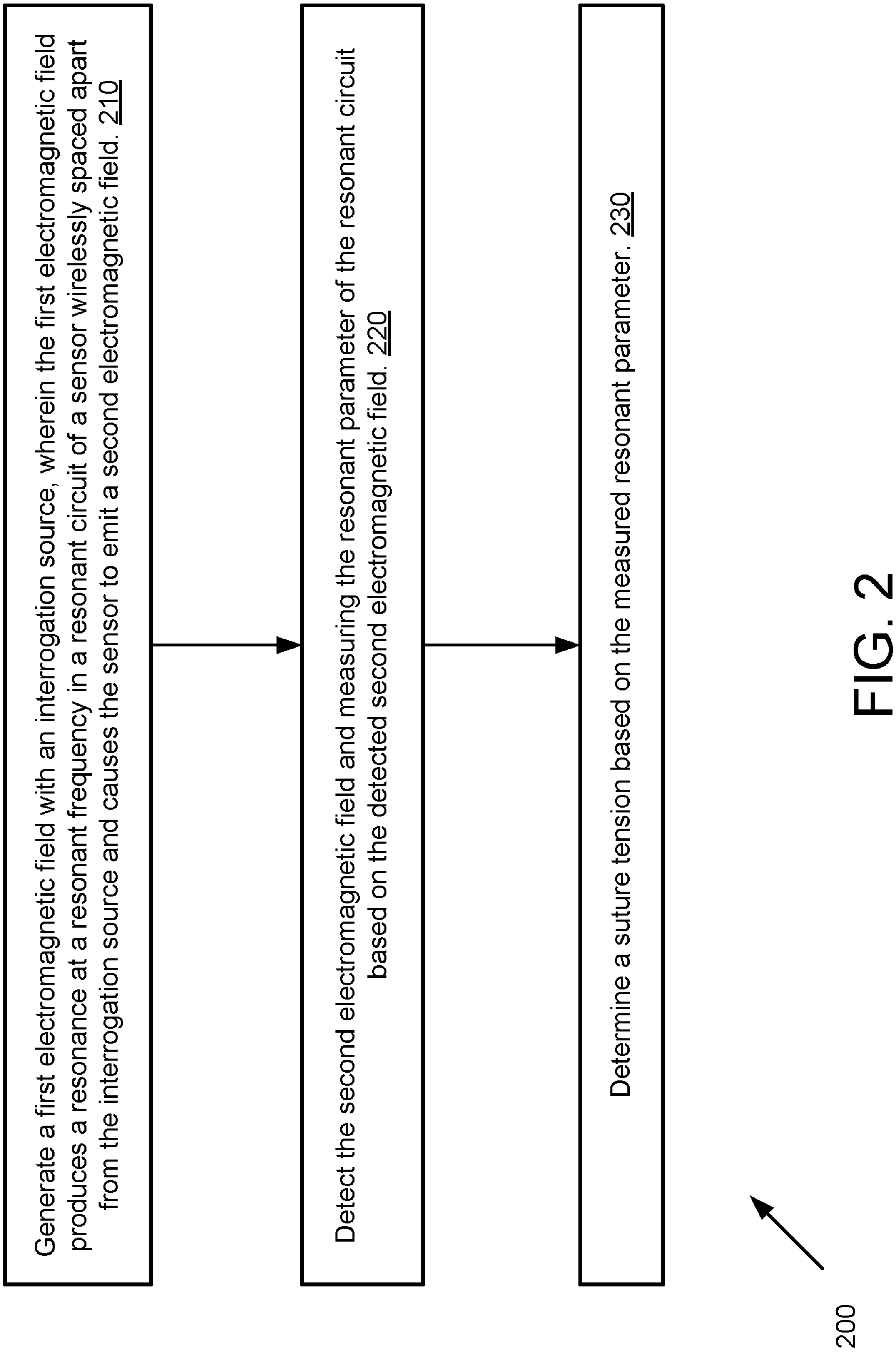
FIG. 2 is a flowchart depicting an example overall method of detecting a tensile force applied to a suture.

FIG. 2 is a flowchart 200 depicting an example overall method of detecting a tensile force applied to a suture.

In some examples, at 210, the method can generate a first electromagnetic field with an interrogation source. The first electromagnetic field can produce a resonance at a resonant frequency in a resonant circuit of a sensor wirelessly spaced apart from the interrogation source and cause the sensor to emit a second electromagnetic field.

In some examples, at 220, the method can detect the second electromagnetic field and measure the resonant parameter of the resonant circuit based on the detected second electromagnetic field.

In some examples at 230, the method can determine a suture tension based on the measured resonant parameter.

In certain examples, the method may include additional steps. For example, the method may include attaching the suture to a substrate of the sensor. In addition, the method may include adjusting a position and/or orientation of the interrogation source to increase a sensitivity of the interrogation source.

The method described in the flowchart 200 and any of the other methods described herein can be performed by computer-executable instructions (e.g., causing a computing system to perform the method) stored in one or more computer-readable media (e.g., storage or other tangible media) or stored in one or more computer-readable storage devices. Such methods can be performed in software, firmware, hardware, or combinations thereof. Such methods can be performed at least in part by a computing system (e.g., one or more computing devices).

Example Suture Tension Measurement Systems

Several suture tension measurement systems that can be used for rehabilitation monitoring after specific orthopedic surgeries are described herein as representative examples, although it should be understood that similar systems can be used for post-operative rehabilitation monitoring for other types of surgeries, or in other surgical or non-surgical applications.

Figure 3B:
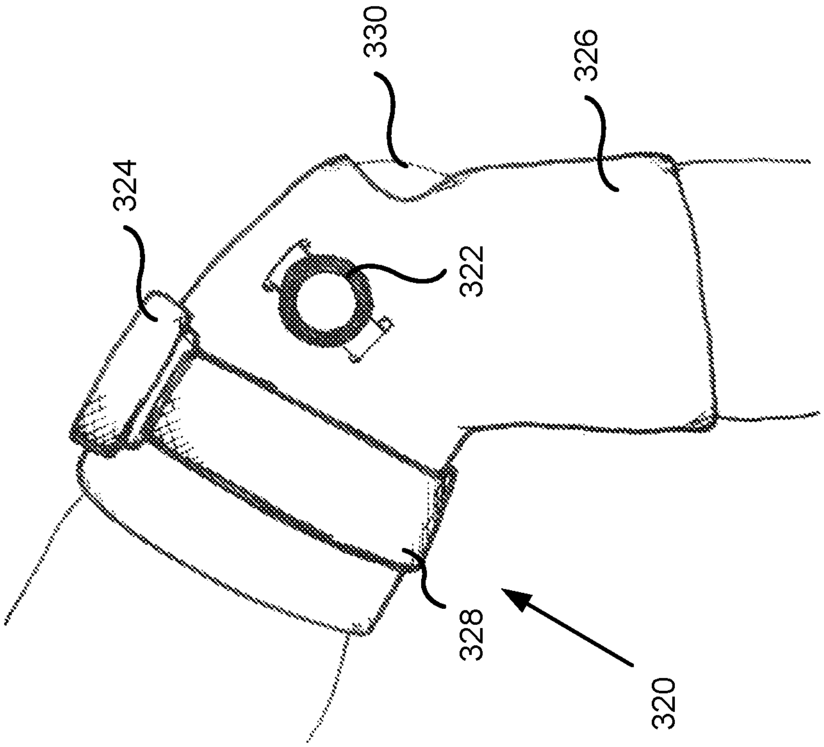
FIG. 3B illustrates a wearable detector configured to measure a tensile force applied to the suture of FIG. 3A, according to one example.
Figure 3A:
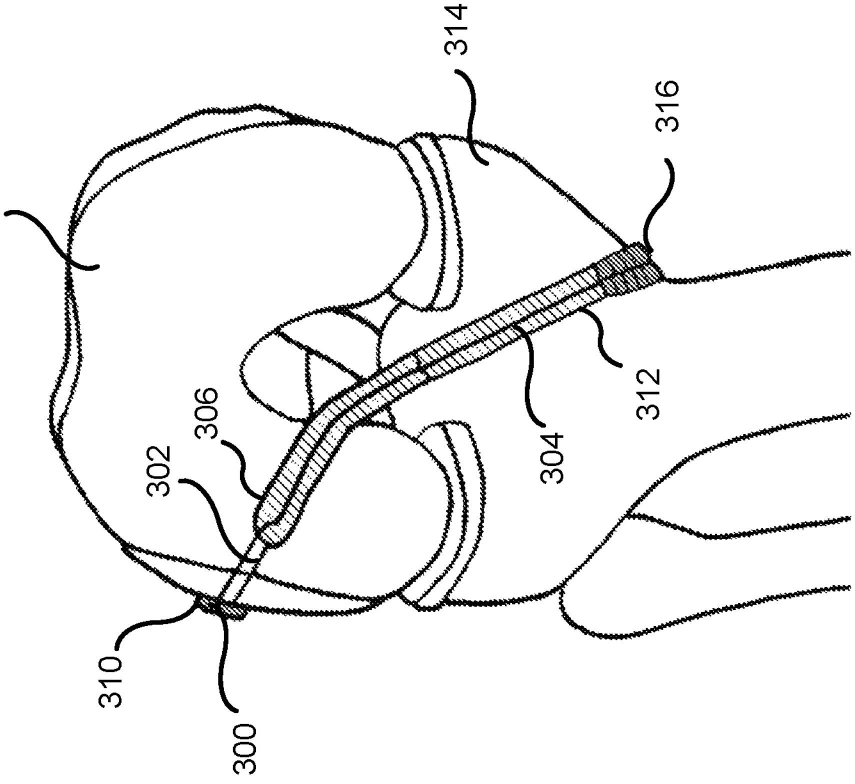
FIG. 3A schematically illustrates using a suture button for anterior cruciate ligament repair.

As one representative example, FIG. 3A schematically illustrates using a suture button 300 for anterior cruciate ligament (ACL) repair, and FIG. 3B depicts a wearable detector 320 configured to wirelessly communicate with the suture button 300 and measure a tensile force applied to a suture 302 shown in FIG. 3A.

Suture buttons are used for many orthopedic surgeries such as ACL repairs, elbow repairs, ankle repairs, etc. During an ACL repair, one end of a suture 302 can be looped through a folded ligament or graft 304, while the other end is looped through a suture button 300. The suture 302 and ligament/graft 304 can pass through a drilled tunnel 306 in the femur 308, while the suture button 300 can rest across an opening 310 of the tunnel 306 to serve as an anchor. The other end of the ligament 304 can pass through a tunnel 312 in the tibia 314 and be secured with bone screws 316 (or another suture button). Monitoring the force loading at the ligament 304 that connects to the femur 308 and tibia 314 can be helpful for evaluating the efficacy of surgical techniques, providing updated assessment of post-surgical healing conditions, and detecting failure of the repair.

As described herein, the suture button 300 can be sensorized (i.e., the suture button 300 becomes an implantable sensor) to allow wireless measurement of tensile force applied to the suture 302 by the ligament 304. As described more fully below, a battery-less sensor can be embedded in the suture button 300. The sensor can have an inductive-capacitive (LC) resonant circuit including at least an inductor and a capacitor embedded inside the suture button 300. When exposed to an electromagnetic field, the resonant circuit can experience an electrical resonance and emit a secondary field at a specific resonant frequency. When suture tension increases, a force can be generated onto the sensor and changes a resonant parameter of the resonant circuit (e.g., by causing a change in capacitance, inductance, and/or resistance value of the resonant circuit). Such change of the resonant parameter can be detected be a detector 320, as described below, thus allowing calculation of the suture tension.

As shown in FIG. 3B, the detector 320, including a detection coil 322 (also referred to as "coil antenna") and the associated electronics 324 (e.g., an impedance analyzer), can wirelessly generate the electromagnetic field and capture the resonant circuit's response. As described more fully below, as a tensile force is applied to the suture 302, it can deform a substrate in the suture button 300 and changes a resonant parameter (e.g., resonant frequency and/or resonance quality factor) of the resonant circuit, thereby allowing determination of the suture tension. Thus, physicians can use this real-time measurement as a continuous biofeedback to make informed decisions and accurately apply evidence-based care.

Generally, the detector 320 can be a portable device that can be placed over the patient's body surface. In certain embodiments, the detector 320 is a wearable device that can be worn by the patient at the surgery site (e.g., patient's knee in this example). As shown in FIG. 3B, the detector 320 can include a wearable mount such as a brace 326 configured to wrap around the knee 330 of the patient. The detection coil 322 and the associated electronics 324 (e.g., an impedance analyzer) can be attached to the brace 326. For example, the detection coil 322 can be affixed to the brace 326 (e.g., via glue, tape, hook-and-loop fastener, or other attachment mechanisms) at a location that is adjacent to the implanted suture button 300. The associated electronics 324 can be spaced apart from the detection coil 322 and secured to the brace 326 by a flexible band 328 (or other attachment mechanisms). Other types of wearable mount can also be used. For example, in certain embodiments, the wearable mount can include an adhesive tape that can be attached to a skin of the patient.

Figure 4B:
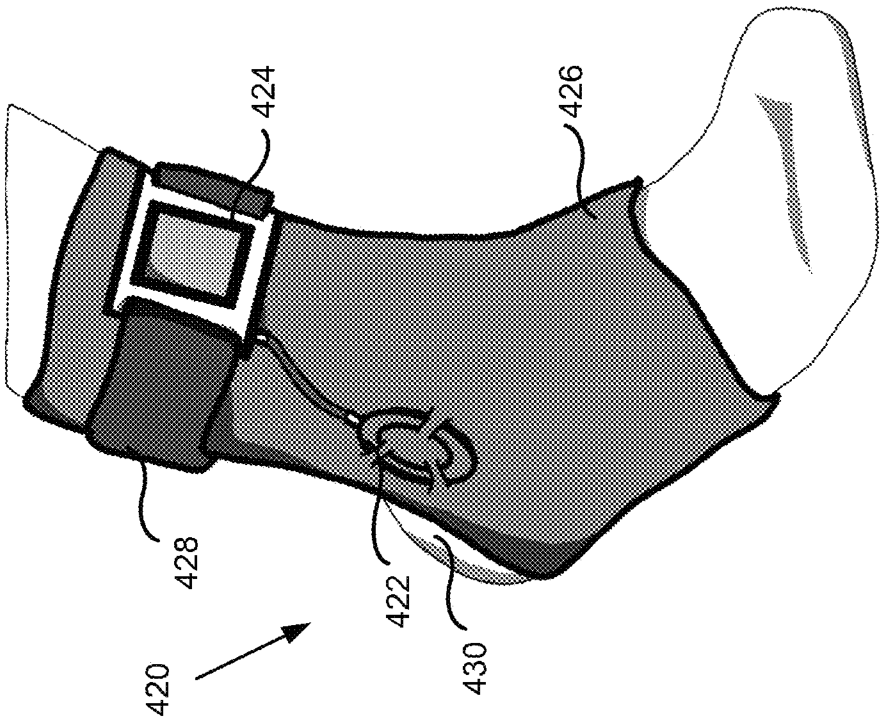
FIG. 4B illustrates a wearable detector configured to measure a tensile force applied to the suture of FIG. 4A, according to one example.
Figure 4A:
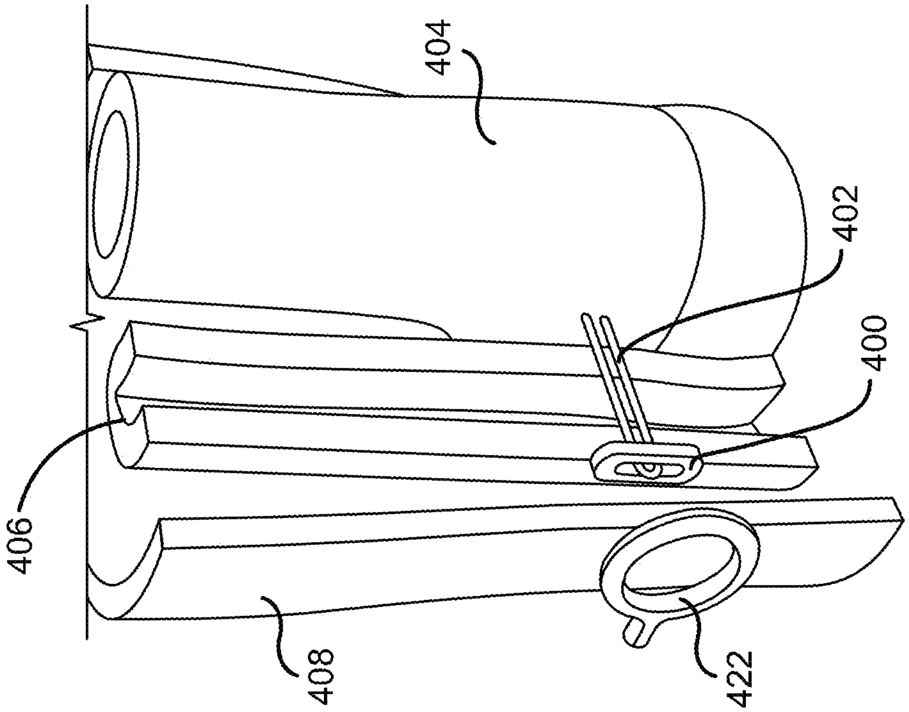
FIG. 4A schematically illustrates an example syndesmosis implant system that can track tension of a suture in a post-surgery patient.

As another example, FIG. 4A schematically illustrates an example syndesmosis (high ankle) implant system that can track tension of a suture 402 in a post-surgery patient, and FIG. 4B illustrates a detector 420 configured to measure a tensile force applied to the suture 402 of FIG. 4A.

Syndesmosis injuries occur when the distal attachment of the tibia and fibula are disrupted. Severe syndesmosis injuries often require surgical interventions that use sutures to stabilize the joint. Severe syndesmosis injuries require surgeries that use sutures to stabilize the ankle, and the tension of the sutures is critical to balance between stability and mobility of the joint.

As shown in FIG. 4A, the ends of the tibia 404 and fibula 406 can be connected to each other by a suture 402. One end of the suture 402 can be securely anchored at the fibula 406 (or another bone) by a suture button 400. Similar to 300 described above, the suture button 400 can be sensorized (i.e., the suture button 400 becomes an implantable sensor) by embedding therein a resonant circuit. A detector 420, as shown in FIG. 4B, can generate an electromagnetic field to excite the resonant circuit, which in turn can emit a secondary field at a specific resonant frequency. The detector 420 includes a detection coil 422, which can be placed over a body surface 408 of the patient at a location adjacent to the suture button 400 to capture the secondary field emitted by the resonant circuit. The detector 420 also includes associated electronics 424 (e.g., an impedance analyzer) connecting to the detection coil 422. As a tensile force is applied to the suture 402, it can deform a substrate in the suture button 400 and changes a resonant parameter (e.g., resonant frequency and/or resonance quality factor) of the resonant circuit, thereby allowing determination of the suture tension.

Similar to 320, the detector 420 can be portable or wearable. In the example depicted in FIG. 4B, the detector 420 includes a brace 426 configured to be worn at the ankle 430 of the patient. Both the detection coil 422 and the associated electronics 424 can be attached to the brace 426, e.g., via a flexible band 428 and/or other attachment mechanisms.

Figure 5B:
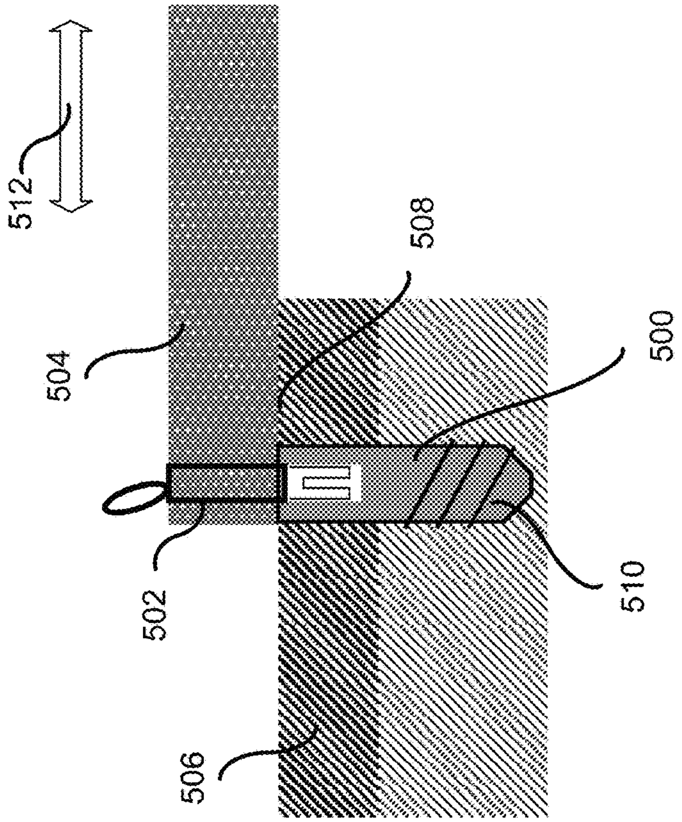
FIG. 5B schematically illustrates a tendon-bone interface with a suture anchor, according to another example.
Figure 5A:
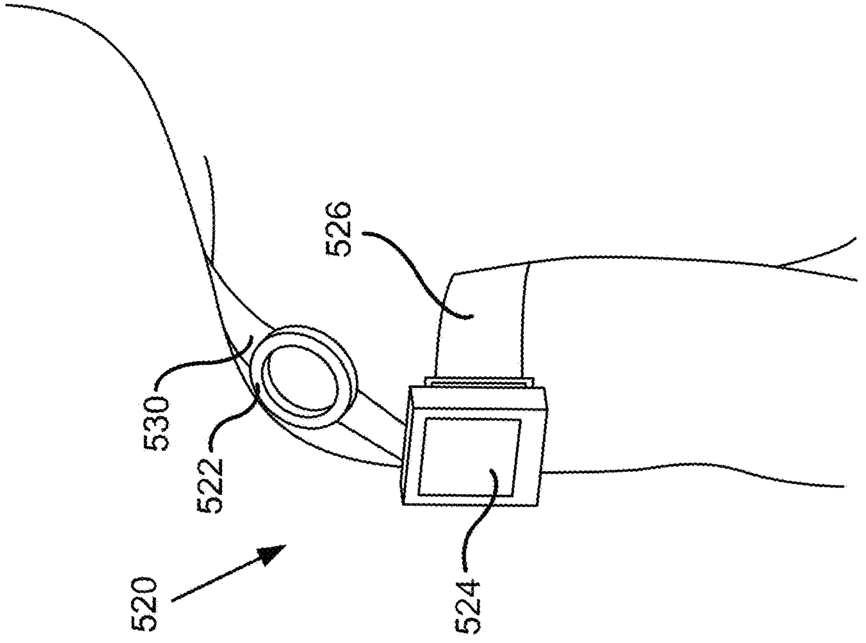
FIG. 5A schematically illustrates a wearable detector configured to measure a tensile force applied to a suture in a suture anchor used for rotator cuff surgery, according to one example.

As yet another example, FIG. 5A shows a detector 520 configured to measure the tensile force applied to a suture inside a patient's shoulder 530 following a rotator cuff repair surgery. Rotator cuff repair typically involves placing small screws (also referred to as "suture anchors") in the upper portion of the arm bone (e.g., humerus) where the rotator cuff tendon normally attaches. The suture anchors can be connected with high-strength sutures that are then placed through the torn tendon, and through a variety of pulley-type techniques the tendon is returned back to the bone at the location of the suture anchors. For illustrative purposes, FIG. 5B schematically shows a suture anchor 500 coupling a tendon 504 to a bone 506. Example embodiments of the suture anchor 500 are described more fully below. A suture 502 has one end that is fixedly coupled to an end portion of the tendon 504 and another end that is connected to the suture anchor 500. The suture anchor 500 has external threads 510 configured to be screwed into the bone 506, thereby attaching the tendon 504 to the bone 506.

Similar to the suture buttons 300 and 400 described above, the suture anchor 500 can be sensorized (i.e., the suture anchor 500 becomes an implantable sensor) by embedding therein a resonant circuit. When exposed to an electromagnetic field generated by the detector 520, the resonant circuit can emit a secondary field at a specific resonant frequency, which can be detected by a detection coil 522 and analyzed by the associated electronics 524 (e.g., an impedance analyzer) of the detector 520. As a tensile force is applied to the suture 502 by the tendon 504, it can deform a substrate in the suture anchor 500 and changes a resonant parameter (e.g., resonant frequency and/or resonance quality factor) of the resonant circuit, thereby allowing measurement of the suture tension.

As described herein, monitoring the change and/or trend of the measured suture tension can be used for quantitative assessment of the patient's post-operative healing status. As indicated by the arrow 512, the tensile force of the tendon 504 is generally along a longitudinal axis of the tendon 504. As a result, the measured suture tension can be generally in parallel to the tendon-bone interface 508. Prior to its healing, the tendon-bone interface 508 can be very weak or nonexistent. As the tendon-bone interface 508 begins to grow during the healing process, the tendon 504 becomes more connected to the bone 506. As a result, the measured suture strain by the suture anchor 500 can be initially high prior to healing (effectively in series with tendon due to the lack or weak tendon-bone interface) and can decrease over time due to the parallel load sharing by the healed tendon-bone interface tissue. Thus, the gradual decrease in measured suture strain can be used to indicate healing and as a quantitative feedback for rehabilitation. In addition, sudden change of the measured suture tension (e.g., exceeding a predefined threshold value) can also be an indicator of suture failure, e.g., due to excessive strain.

Although suture buttons 300, 400 and suture anchor 500 are described in the above examples, it should be understood that they are merely used to illustrate the principles of the technologies described herein, and different forms of implantable sensors can be used. For example, instead of using suture buttons 300, 400, one or more suture anchors similar to 500 can be used to anchor the sutures 302, 402 in FIGS. 3A and 4A. Likewise, instead of using suture anchor 500, one or more suture buttons similar to 300, 400 can be connected to the suture 502 in FIG. 5B. In certain scenarios, depending on the anatomical environment of the surgical site, the suture (e.g., 302, 402, 502) can be connected to an anchor device that has a different shape than a button (like suture button) or a screw (like suture anchor). In fact, the anchor device can have any geometric shape so long as it can securely hold the suture at an anchoring site (e.g., a bone). Such anchor device can be sensorized to become an implantable sensor by embedding a resonant circuit therein similar to the 300, 400, and 500 described above. Based on the same principles described above, a detector similar to 320, 420, and 520 can be used to wirelessly communicate with the anchor device and measure the tensile force applied to the suture.

Example Suture Button Embedded with an Inductor-Capacitor (LC) Resonant Circuit

Figure 6A:
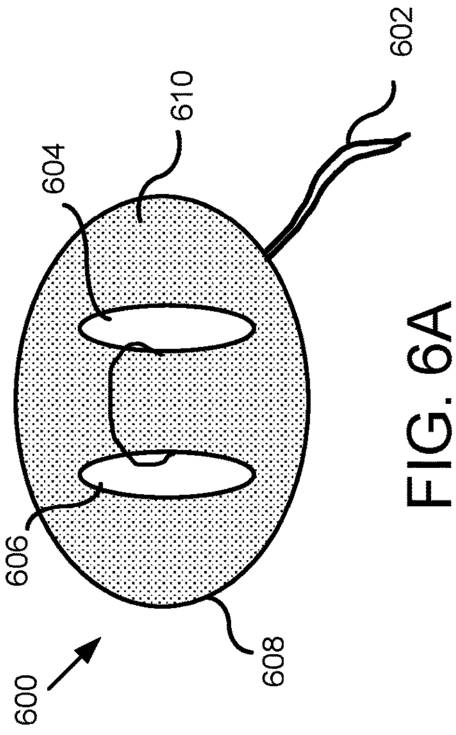
FIG. 6A schematically illustrates a top view of a suture button, according to one example.
Figure 6B:
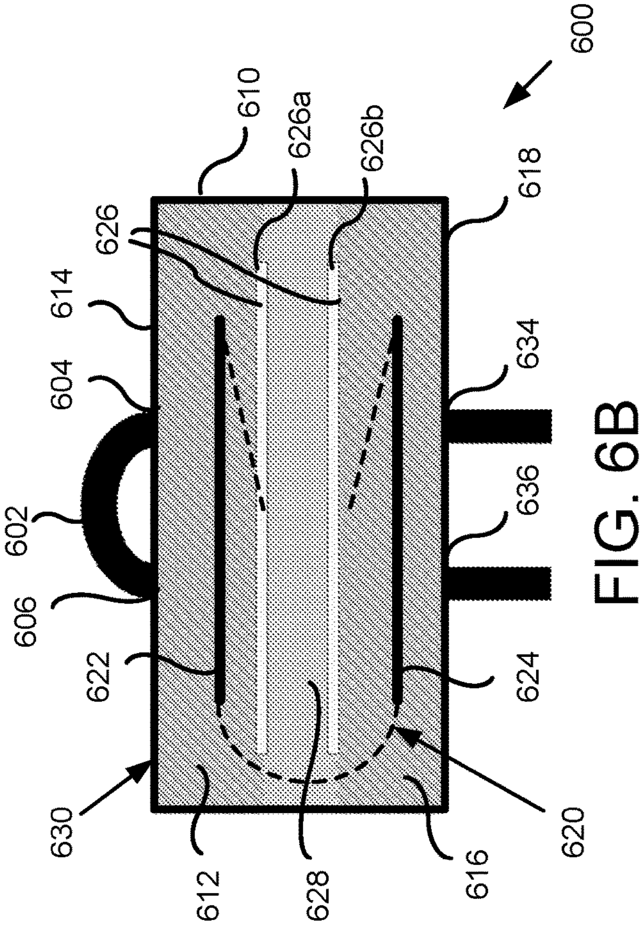
FIG. 6B schematically illustrates a cross-sectional view of the suture button of FIG. 6A.
Figure 6C:
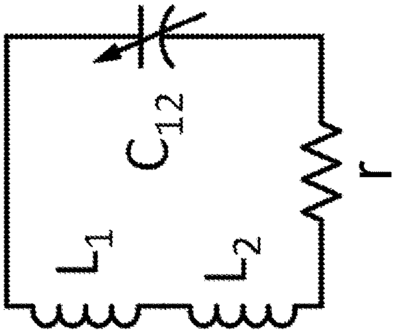
FIG. 6C depicts a circuit diagram of a resonant circuit embedded in the suture button of FIGS. 6A-6B.
Figure 6D:
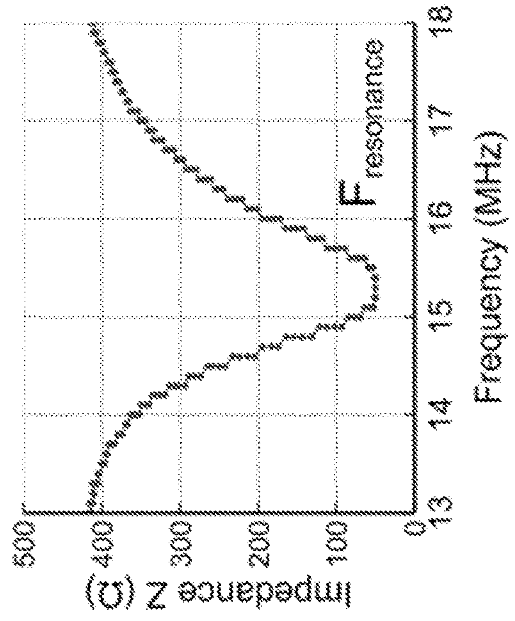
FIG. 6D depicts a resonance spectrum of the resonant circuit of FIG. 6C.

FIGS. 6A-6B (not drawn to scale) schematically depicts a suture button 600 that can be connected to a suture 602, according to one example. The loose ends of the suture 602 can be connected to a biological tissue, such as a ligament (not shown). The suture button 600 can be sensorized by embedding a resonant circuit 620 therein. Thus, the suture button 600 can be configured as an implantable sensor (which can also be referred to as a sensor assembly). A circuit diagram of the resonant circuit 620 is shown in FIG. 6C, and an example resonance spectrum of the resonant circuit 620 is depicted in FIG. 6D. The suture button 600 can be any one of the suture buttons 300, 400 described above.

The suture button 600 has a substrate 630 and the resonant circuit 620 is coupled to the substrate 630. In the depicted example, the resonant circuit 620 is an LC resonant circuit including two planar (and spiral) inductor coils 622, 624 and a capacitor 626 comprising two parallel conductive plates 626*a*, 626*b*.

In the depicted example, the substrate 630 includes two printed circuit boards (PCBs) 612, 616 and a compliant layer 628 situated between the two conductive plates 626*a*, 626*b*. The compliant layer 628 can comprise a compliant material (which can be natural and/or synthetic), such as neoprene. The substrate 630 also includes an enclosure 610 encasing the two PCBs 612, 616, the capacitor 626, and the compliant layer 628. The two inductor coils 622, 624 can be respectively printed on or embedded in the two PCBs 612, 616. The two conductive plates 626*a*, 626*b* can be respectively attached to or embedded in the two PCBs 612, 616. Thus, the resonant circuit 620 is also enclosed within the enclosure 610. In any of the examples described herein, the enclosure can also be referred to as a case or a housing.

The enclosure 610 can have one or more apertures through which the suture 602 can extend and loop around at least a portion of the enclosure 610. In the depicted example, the enclosure 610 has a first cover 614 and a second cover 618 that are generally parallel to each other. Two apertures 604, 606 are located on the first cover 614 and two apertures 634, 636 are located on the second cover 618. Thus, the suture 602 can be inserted into the substrate 630 through the aperture 634 and pulled out of the substrate 630 through the aperture 604. After looping over a portion of an outer surface of the first cover 614, the suture 602 can be inserted back into the substrate 630 through the aperture 606 and pulled out of the substrate 630 through the aperture 636.

Although only one loop is shown in FIG. 6A, it is to be understood that the suture 602 can loop over a portion of substrate 630 multiple times for more secure attachment. Although the apertures 604, 606 are shown in oval shapes, it is to be understood that apertures 604, 606, 634, 636 can have any geometric shape (and/or have different sizes) so long as they allow the suture 602 to extend therethrough. It is also understood that the number of apertures on the first cover 614 and/or the second cover 618 can be less than or more than two. For example, three, four, or more apertures can be placed on each of the first and second covers 614, 618 for threading the suture 602. Alternatively, the first and/or second covers 614, 618 can have only one aperture or no aperture at all. For example, the edge 608 of the first and/or second covers 614, 618 can have one or more recesses configured to receive the suture 602. Thus, instead of threading through apertures, the suture 602 can extend and loop around at least a portion of the enclosure 610 through such recesses. Any other suture retaining mechanisms (e.g., hooks, eyelets, glue, clips, etc.) can be used to attach the suture 602 to the substrate 630. In any of the examples described herein, one or more knots can be formed to more securely tie the suture 602 to the substrate 630.

The dimension of the suture button 600 can be configured differently based on applications and/or the surgical sites. In certain examples, the suture button 600 can have a length ranging from about 5 mm to about 40 mm and a width ranging from about 2 mm to about 20 mm. In certain examples, the thickness of each PCB 612, 616 can range from about 0.2 mm to about 5 mm. In certain examples, the compliant layer 628 an have a thickness ranging from about 0.5 mm to about 3 mm (e.g., about 1.5 mm). It is to be understood that the dimensions described herein are merely exemplary. The suture button 600 and its components can have larger or smaller dimensions than the values noted above depending on the particular applications.

The enclosure 610 can include a biocompatible material having a predefined stiffness and flexibility. For example, the enclosure 610 can be made of polyether ether ketone (PEEK) which is biocompatible, can withstand an external force of up to 200 N or higher, and has a relatively high flexural modulus (e.g., about 4 GPa). Thus, when a tensile force is applied to the suture 602, the enclosure 610 can deform as a result (e.g., pulling the suture 602 in a downward direction in FIG. 6B can cause the first cover 614 of the enclosure 610 to bend downwardly).

The enclosure 610 and the two PCBs 612, 616 can be held together, e.g., using a silicone elastomer adhesive which can also act as a compliant material (e.g., with a final cured hardness of about 24 A durometer). The adhesive can be selected to have an established ISO 10993 biocompatibility. In addition, the PCBs 612, 616 and the parallel-plate capacitor 626 can have a layer of conformal Parylene-C coating to prevent absorption of liquid that may interfere with the sensor's performance, and to further improve its biocompatibility.

The two PCBs 612, 616 can be made of flexible, biocompatible polyimide-based material so that they can deform when a bending force is applied to the PCBs. For example, when a tensile force is applied to the suture 602, it can deform (e.g., bend) the first cover 614 of the enclosure 610, which in turn can deform (e.g., bend) the PCB 612. Because the compliant layer 628 is sandwiched between the two conductive plates 626*a*, 626*b*, deformation of the first cover 614 and the corresponding deformation of the PCB 612 can also deform the compliant layer 628 sandwiched between the two conductive plates 626*a*, 626*b*, thereby changing the capacitance of the capacitor 626. For example, in FIG. 6B, increasing the suture tension in the downward direction can press the conductive plate 626*a* downwardly toward the conductive plate 626*b* (e.g., moving to a biased position), thereby increasing the capacitance of the capacitor 626. Conversely, reducing the suture tension can cause the conductive plate 626*a* to return toward its unbiased position (e.g., moving away from the conductive plate 626*b*), thereby decreasing the capacitance of the capacitor 626.

The two inductors 622, 624 and the parallel-plate capacitor 626 can be connected in series, forming the resonant circuit 620, the circuit diagram of which is shown in FIG. 6C. For illustrative purposes, the electrical connections between the inductors 622, 624 and the capacitor 626 are also indicated by the dotted lines in FIG. 6B. In the circuit diagram depicted in FIG. 6C, the inductance of the inductors 622, 624 are respectively denoted as L1 and L2, and the capacitance of the capacitor 626 is denoted as $C_{12}$. In the depicted example, L1 and L2 are constant, whereas $C_{12}$ can vary, e.g., due to variation of the tensile force applied to the suture 602, as described above. The inductance of the two inductors 622, 624 can be the same (i.e., L1=L2) or different (i.e., L1≠L2). The circuit diagram in FIG. 6C also shows a resistance r, which represents a conductor resistance of the resonant circuit (e.g., the inherent resistance of the inductors, the capacitor, and the connecting wires). Generally, the conductor resistance r is small (e.g., less than 1 Ohm) and remains constant.

When exposed to an electromagnetic field, the resonant circuit 620 can experience an electrical resonance and emit a secondary electromagnetic field at a specific resonant frequency. For a series LC resonant circuit (e.g., 620), the resonance occurs at a frequency at which the impedance of the circuit is at its minimum, e.g., if there is no reactance in the circuit. This occurs when the reactance of the inductor and the capacitor are equal and cancel each other because of their opposite signs. More specifically, this happens at the resonant frequency ($f_0$) given by the following equation:

$$f_0 = \frac{1}{2\pi\sqrt{LC}} \tag{1}$$

where C is the capacitance of the capacitor (equals to $C_{12}$ in this case) and L is the total inductance of the inductors. In the depicted example, because the two inductors 622, 624 are in series, the total inductance L of the inductors 622, 624 is the sum of L1 and L2 (i.e., L=L1+L2).

The resonance spectrum of the resonant circuit 620 can be extracted from a coil impedance spectrum measured by a detector such as 320, 420, and 520 noted above, and described more fully below. As an example, FIG. 6D shows the measured resonant frequency of a resonant circuit is between 15 MHz and 16 MHz.

As noted above, when a tensile force is applied to the suture 602, it can deform the substrate 630 and change the capacitance of the capacitor 626. As a result, different suture tensions can correspond to different resonant frequencies of the resonant circuit 620. Thus, by measuring the resonant frequency of the resonant circuit 620, the tensile force applied to the suture can be obtained (e.g., based on a previously obtained calibration curve the characterizes the relationship between the suture tension and the resonant frequency).

In the example depicted in FIG. 6B, increasing the suture tension can increase the capacitance of the capacitor 626 (thus decreasing the resonant frequency of the resonant circuit 620), and vice versa. Alternatively, the suture button 600 can be configured to decrease the capacitance of the capacitor 626 (thus increasing the resonant frequency of the resonant circuit 620) when increasing the suture tension. This can be achieved, for example, by fixedly attaching the suture 602 to the second cover 618 of the enclosure 610. For instance, the suture 602 can be inserted into the substrate 630 through the aperture 634 and then immediately pulled out of the substrate 630 through the aperture 636 (e.g., the suture 602 loops over a portion of an inner surface of the second cover 618, instead of looping over a portion of the outer surface of the first cover 614). Thus, increasing the suture tension in the downward direction (as in FIG. 6B) can pull the conductive plate 626*b* away from the conductive 626*a* (thus decreasing the capacitance of the capacitor 626), and vice versa.

Although two inductors 622, 624 are shown FIGS. 6B-6C, it is to be understood that, in certain examples, the suture button 600 can have only one inductor (e.g., one of the inductors 622 or 624 can be optional), and the total inductance of the resonant circuit 620 is the inductance of the remaining inductor. In other examples, the suture button 600 can have more than two inductors. For instance, additional coil conductors can be attached to the substrate 630, and these additional coil conductors can be connected to any of the electrical components (e.g., 622, 624, 626) in series and/or in parallel, thus resulting in different total inductance of the resonant circuit 620 and the corresponding shift of the resonant frequency. Likewise, although only one capacitor 626 is shown in FIGS. 6B-6C, it is to be understood that, in certain examples, the suture button 600 can have more than one capacitor. For instance, additional capacitors (which can be parallel-plate capacitors or other types of capacitors) can be attached to the substrate 630, and these additional capacitors can be connected to any of the electrical components (e.g., 622, 624, 626) in series and/or in parallel, thus resulting in different total capacitance of the resonant circuit 620 and the corresponding shift of the resonant frequency.

Although FIG. 6B shows only one resonant circuit 620 in the suture button 600, it is to be understood that, in certain circumstances, multiple resonant circuits having different resonant frequencies (when exposed to an excitation electromagnetic field) can be embedded in the suture button 600. Thus, one suture button 600 can embed multiple implantable sensors which can be simultaneously detected by a single detector (e.g., 160), as described above.

In certain embodiments, the multiple resonant circuits can be coupled to the same substrate 630 and configured to change respective resonant frequencies in response to the same deformation of the substrate 630. Such configuration can be used to provide multiple readings with different sensitivities for the same suture tension that causes the deformation of the substrate 630. In certain embodiments, multiple resonant circuits can be configured to change respective resonant frequencies in response to different deformations of the substrate 630. For example, while one resonant circuit is configured to change its resonant frequency in response to the deformation of the substrate 630 along a first axis, another resonant circuit can be configured to change its resonant frequency in response to the deformation of the substrate 630 in a second axis that is different from the first axis.

In certain embodiments, the multiple resonant circuits can be coupled to different substrates (e.g., another substrate that is separate from and/or independent of 630) of the suture button 600, wherein each substrate is configured to deform in response to the tensile force applied by the suture 602. In certain examples, the multiple substrates can be configured to deform in the same direction in response to the tensile force applied by the suture 602. Additionally, such multiple substrates can be configured to deform to different extents and/or degrees in response to the tensile force applied by the suture 602. In other examples, the multiple substrates can be configured to deform in different directions in response to the tensile force applied by the suture 602.

Figures 7A, 7B, 7C:
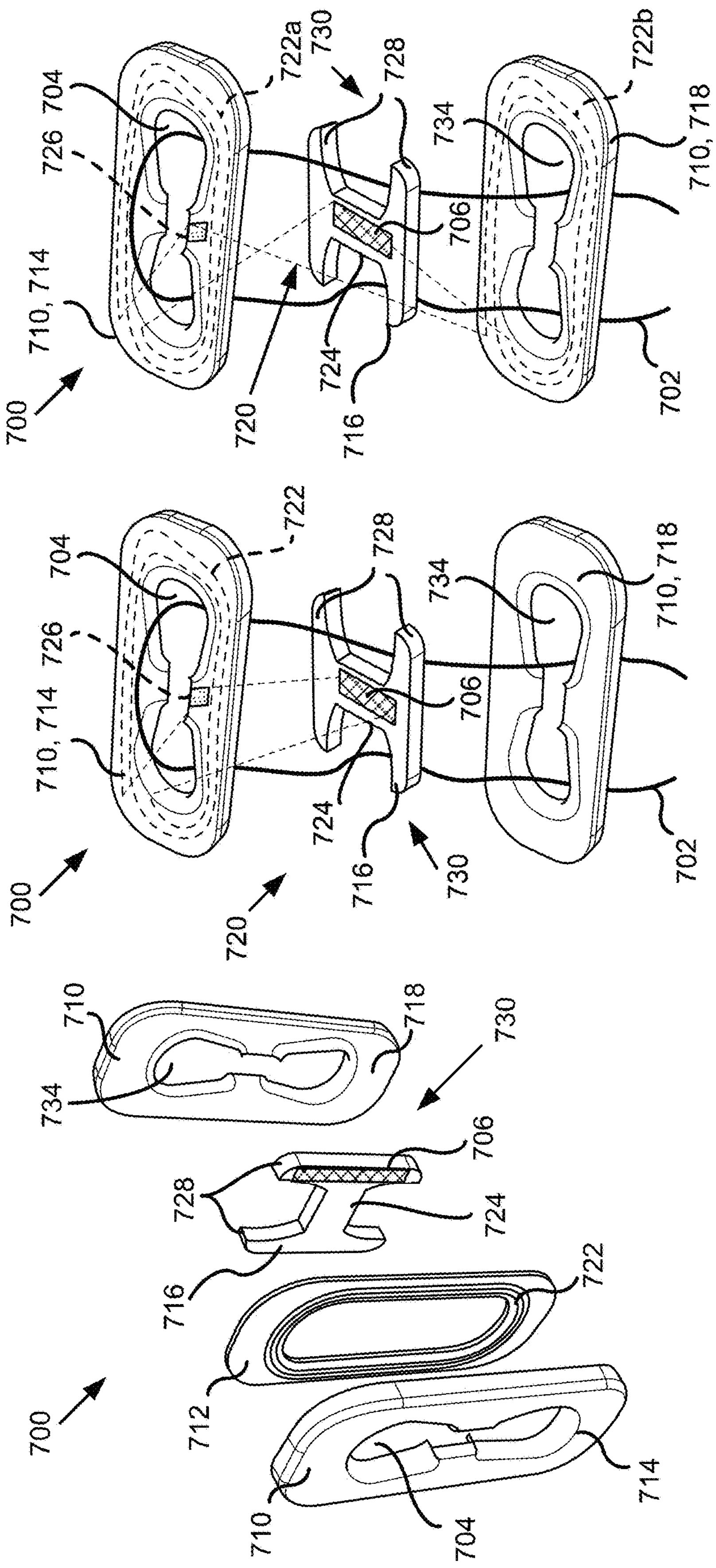
FIG. 7A is an exploded view of a suture button including a strain gauge, according to one example.
FIG. 7B schematically illustrates a suture button and an embedded resonant circuit including a strain gauge, according to another example.
FIG. 7C schematically illustrates a suture button and an embedded resonant circuit including a strain gauge, according to yet another example.

Example Suture Button Embedded with an Inductor-Capacitor-Resistor (LCR) Resonant Circuit FIGS. 7A-7C (not drawn to scale) schematically depicts a suture button 700 that can be connected to a suture 702, according to another example. The loose ends of the suture 702 can be connected to a biological tissue (not shown). The suture button 700 can be sensorized by embedding a resonant circuit 720 therein. Thus, the suture button 700 can be configured as an implantable sensor (which can also be referred to as a sensor assembly). The suture button 700 can be any one of the suture buttons 300, 400 described above. The dimension of the suture button 700 can be similar to the suture button 600.

The suture button 700 has a substrate 730 and the resonant circuit 720 is coupled to the substrate 730. In the depicted example, the resonant circuit 720 is a specific type of LC resonant circuit including a resistor, denoted herein as an inductor-capacitor-resistor (LCR) resonant circuit. Specifically, the resonant circuit 720 includes at least one capacitor 726, one or more inductors 722 (or 722*a*, 722*b*), and a strain gauge 706 having a resistance that varies in response to a deformation of the strain gauge 706. The electrical connections between the inductors 722 (or 722*a*, 722*b*), the capacitor 726, and the strain gauge 706 are indicated by the dotted lines in FIGS. 7B-7C.

In any of the examples described herein, the strain gauge (including 706) can be replaced with any other types of resistive transducer (also known as variable resistance transducer), as long as it has a resistance that varies in response to a deformation of the resistive transducer.

As described herein, various types of strain gauge 706 can be used. For example, the strain gauge 706 can be a semiconductor strain gauge, a thin-film strain gauge, a foil strain gauge, a wire strain gauge, etc. The strain gauge 706 can be configured to measure a positive strain due to elongation of the strain gauge 706 or a negative strain due to compression of the strain gauge 706. The strain gauge 706 can be configured to have a gauge factor with a predefined range (e.g., from about 2 to about 1,000).

In the depicted example, the substrate 730 includes an enclosure 710 comprising a first cover 714 and a second cover 718. Similar to 610, the enclosure 710 can be made of a biocompatible material (e.g., PEEK) having a predefined stiffness and flexibility. Likewise, the covers 714, 718 can have one or more apertures 704, 734 through which the suture 702 can extend (or using other suture retention mechanisms such as recesses, eyelets, hooks, etc.) and loop over a portion of the substrate 730. Additional fastening mechanism (e.g., multiple loops, knots, etc.) can be employed to attach the suture 702 more securely to the substrate 730. A layer of conformal Parylene-C coating can be deposited onto the enclosure 710 to prevent absorption of liquid and improve its biocompatibility.

The substrate 730 also includes a PCB 712 and a frame 716, both of which can be encased by the enclosure 710. The substrate 730 can be made of a flexible material similar to 612 and 616. As shown in FIG. 7A, a planar (and spiral) inductor coil 722 can be printed on or embedded in the PCB 712. The PCB 712 can be fixedly attached to or embedded within the first cover 714 (e.g., FIG. 7B depicts the inductor coil 722 embedded in the first cover 714). In certain examples, more than one inductor coils can be embedded in the enclosure 710. For example, FIG. 7C depicts two planar spiral inductor coils 722*a*, 722*b* that are respectively embedded in the first and second covers 714, 718. These two inductor coils 722*a*, 722*b* can be connected in series to increase the overall inductance of the resonant circuit 720.

The inductor coil(s) 722 (or 722*a*, 722*b*) can be connected to the capacitor 726 in series. The capacitor 726 can be a surface mount capacitor (e.g., a monolithic ceramic capacitor, a film capacitor, an interdigital capacitor, etc.) that is embedded within the substrate 730. In the example depicted in FIGS. 7B-7C, the capacitor 726 is embedded within the first cover 714. In other examples, the capacitor 726 can be embedded within the second cover 718 or any other location enclosed by the enclosure 710. In certain examples, the resonant circuit 720 can have more than one capacitors embedded within the substrate 730. As noted above, the additional inductors and/or capacitors can be connected to any of the electrical components in the resonant circuit 720 in series and/or in parallel, thus resulting in different resonant frequencies of the resonant circuit 720.

The strain gauge 706 can be fixedly attached (e.g., by way of gluing using epoxy resin, another adhesive, or other fastener or attachment mechanism) to the frame 716, which is sandwiched between and generally parallel to the first and second covers 714, 718. The frame 716 can have a predefined flexural modulus so that it can deform within a certain range under a force loading. The frame 716 can also have a predefined stiffness so that it can tolerate a force loading of up to 200 N or higher. In certain examples, the frame 716 can be made of stainless steel. In certain examples, the frame 716 can be made of other metal/alloy and/or nonmetallic materials.

In the depicted examples, the frame 716 has an "H" shape defined by two parallel bars 728 and a bridge 724 extending between and connecting the two parallel bars 728. Thus, the suture 702 can loop over the frame 716 by passing through spaces on both sides of the bridge 724 and between the two parallel bars 728. It is to be understood that the frame 716 can be designed to have any other shapes so long as it allows the suture 702 to pass through and loop over the frame 716. For example, the frame 716 can have a disk shape and have two or more apertures through which the suture 702 can extend.

The strain gauge 706 can be attached to the frame 716 at a location that maximizes sensitivity of the strain gauge 706 (e.g., the location where the strain gauge 706 is most sensitive to the external force applied to the frame 716). Depending on how the suture 702 is attached to the suture button 700 (e.g., the routing path of the suture 702 within the substrate 730), the location where the strain gauge 706 is attached to the frame 716 can vary. For example, in FIG. 7A, the strain gauge 706 is attached to one of the parallel bars 728 of the frame 716, whereas in FIGS. 7B-7C, the strain gauge 706 is attached to the bridge 724. In certain embodiments, the strain gauge 706 can be oriented relative to the frame 716 such that the strain gauge 706 is deformed substantially in the same direction as the tensile force applied by the suture 702. In certain embodiments, the strain gauge 706 can be oriented relative to the frame 716 such that the strain gauge 706 is deformed in a direction that forms an oblique angle relative to a direction of the tensile force applied by the suture 702.

Similar to the example described above in reference to FIGS. 6A-6B, applying a tensile force to the suture 702 can deform the substrate 730. For example, pulling the suture 702 in a downward direction in FIGS. 7B-7C can cause the first cover 714 to bend downwardly, which in turn can deform the frame 716 and the strain gauge 706 attached thereto. Deformation of the strain gauge 706 changes its resistance, thereby changing certain resonant properties (e.g., resonance quality factor) of the resonant circuit 720, as described below.

Figure 8B:
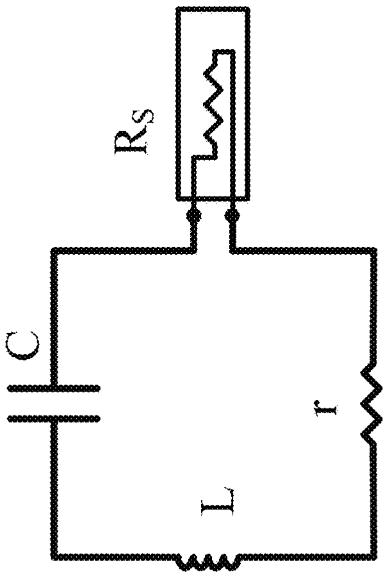
FIG. 8B depicts a circuit diagram of a resonant circuit embedded in the suture anchor of FIG. 8A or the suture button of FIGS. 7A-7C.

FIG. 8B depicts a circuit diagram of an LCR resonant circuit, which can represent the resonant circuit 720 embedded in the suture button 700. As shown, the LCR resonant circuit includes a capacitor (with a capacitance C), an inductor (with an inductance L), and a resistor (with a resistance $R_s$) connected in series. Referring to the resonant circuit 720, C can represent the capacitance of the capacitor 726, L can represent the inductance of the inductor 722 (or the combined inductance of inductors 722*a* and 722*b*), and $R_s$ can represent the resistance of the strain gauge. In such case, both C and L remain generally constant, whereas $R_s$ can vary in response to the deformation of the strain gauge 706 due to a tensile force applied to the suture 702. The LCR circuit diagram depicted in FIG. 8B also shows a resistance r, which represents a conductor resistance of the circuit. Generally, the conductor resistance r is much smaller than the resistance of the strain gauge (i.e., $r<<R_s$) and remains constant. For example, a lowest resistance of the strain gauge 706 (i.e., $\min(R_s)$) when it is deformed can be at least 10 times more than the conductor resistance r. In certain examples, the ratio between $\min(R_s)$ and r can range from about 50 to about 100. In certain examples, the ration between $\min(R_s)$ and r can be greater than 100.

The resonance quality factor (also referred to as the "Q factor") is a dimensionless parameter that describes how underdamped an oscillator or resonator is, thus the quality of a resonant circuit. For the resonant circuit depicted in FIG. 8B, its resonant frequency ($f_0$) is still determined by the inductance (L) and capacitance (C), as shown above in equation (1).

Figure 8C:
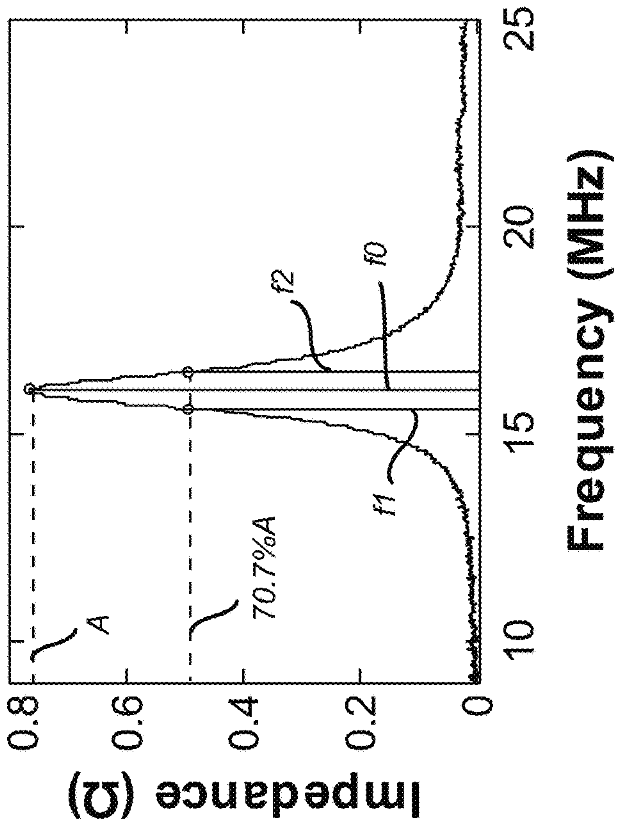
FIG. 8C depicts calculation of a resonance quality factor based on a resonance curve.

The resonance quality factor Q can be determined from the frequency response of the resonant circuit near its resonant frequency as illustrated in FIG. 8C. Specifically, the resonance quality factor Q can be calculated from the ratio of the resonant frequency $f_0$ and the half-power bandwidth B (i.e., the bandwidth between the two frequencies $f_1$, $f_2$ with signal strength equal to about 70.7% of the resonance amplitude A) as:

$$Q = \frac{f_0}{B} = \frac{f_0}{f_2 - f_1} \tag{2}$$

For the LCR resonant circuit depicted in FIG. 8B, it can be shown that the resonance quality factor Q factor is dependent on the total impedance of the sensor as:

$$Q = \frac{1}{r + R_s}\sqrt{\frac{L}{C}} \tag{3}$$

Thus, if L and C remain constant during deployment of the suture button 700, and the conductor resistance r is negligible (because $r \ll R_s$), then the resonance quality factor Q is approximately proportional to the inverse of the strain gauge resistance $R_s$. As noted above, $R_s$ varies in response to the deformation of the strain gauge 706 caused by the tensile force applied to the suture 702. Thus, by measuring the resonance quality factor of the resonant circuit 720, the tensile force applied to the suture 702 can be determined.

Although FIGS. 7A-7C show only one resonant circuit 720 in the suture button 700, it is to be understood that, in certain circumstances, multiple resonant circuits having different resonant frequencies can be embedded in the suture button 700. Thus, a single suture button 700 can embed multiple implantable sensors which can be simultaneously detected by a single detector (e.g., 160). Similarly, these multiple resonant circuits can be coupled to the same substrate 730 and configured to change respective resonant frequencies in response to the same or different deformations of the substrate 730. Alternatively, these multiple resonant circuits can be coupled to different substrates, each of which is configured to deform (e.g., to different extents and/or in different directions) in response to the tensile force applied by the suture 702.

Additional Examples of Suture Buttons and Suture Button Assemblies

The suture buttons 600, 700 described above are merely two examples of implantable sensors. FIGS. 7D-7G depict additional examples of implantable suture buttons and/or suture button assemblies.

Figure 7D:
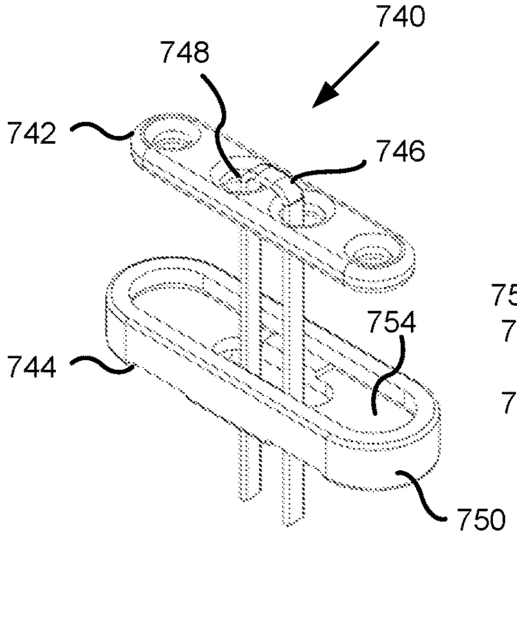
FIG. 7D depicts a suture button assembly, according to another example.
Figure 7E:
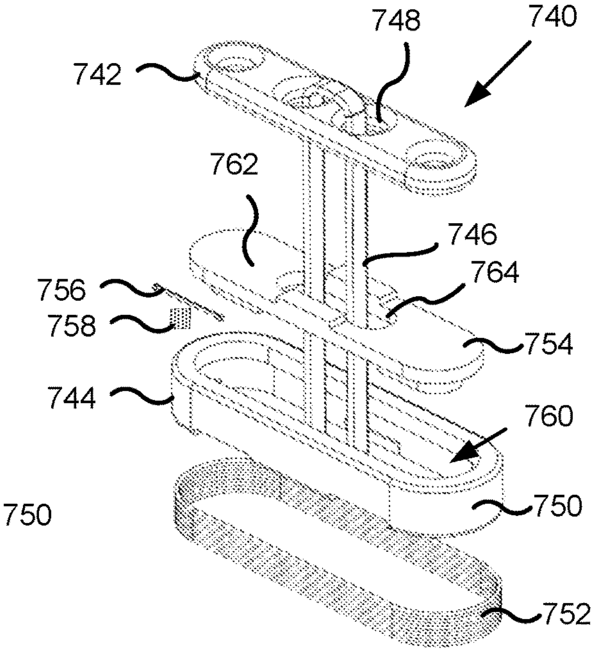
FIG. 7E is an exploded view of the suture button assembly of FIG. 7D.
Figure 7F:
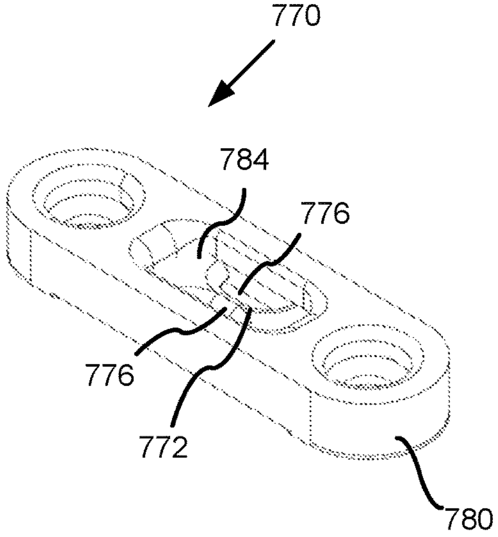
FIG. 7F depicts a suture button, according to yet another example.
Figure 7G:
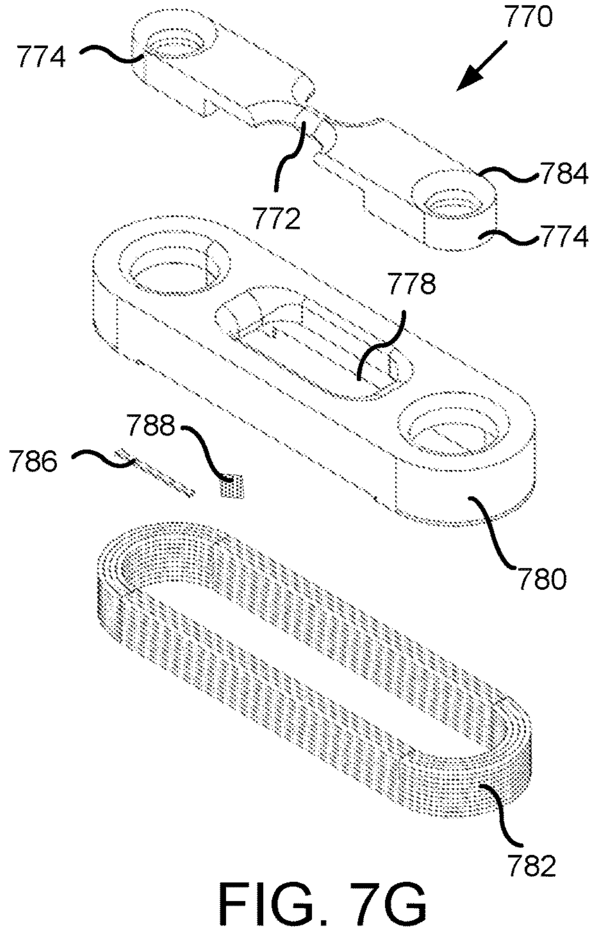
FIG. 7G is an exploded view of the suture button of FIG. 7F.

In one example, FIGS. 7F-7G depicts another sensor button 770 embedded with a resonant circuit. The sensor button 770 can be configured as an implantable sensor, which can also be referred to as a sensor assembly comprising a substrate (e.g., a deformable member 784) and a resonant circuit coupled to the substrate. Although the depicted sensor button 770 has a generally oblong button shape with a straight middle portion and two rounded end portions, it is to be understood that the sensor button 770 can be configured to different shapes (e.g., oval, rectangle, square, etc.).

As shown, the sensor button 770 includes an enclosure 780 which is embedded with a resonant circuit. In one example, the resonant circuit (similar to 720) can be formed by an inductor 782, a deformable member 784, a strain gauge 786, and a capacitor 788. In other examples, the strain gauge 786 can be optional, thus forming a resonant circuit similar to 620. For example, the capacitor 788 can comprise two opposing conductive plates (similar to 626*a*, 626), one of which is connected to the deformable member 784, whereas the other is spaced away from the deformable member 784.

The enclosure 780 can comprise a polymeric material and/or a metallic material. In some examples, the enclosure 780 can be configured to enclose and/or encapsulate the inductor 782, the deformable member 784, the strain gauge 786, and the capacitor 788. For example, the inductor 782 can be placed along an inner wall of the enclosure 780. In some examples, more than one inductor 782 can be placed within the enclosure 780. The strain gauge 786 and the capacitor 788 can be placed anywhere within the enclosure 780. In one particular example, the strain gauge 786 and the capacitor 788 can be disposed on a bottom surface of the deformable member 784.

The deformable member 784 has a predefined flexural modulus so that it can deform within a certain range under a force loading. In some examples, the deformable member 784 can comprise a bendable metal and/or a metallic alloy. In some examples, the deformable member 784 can comprise a compliant polymeric material. As shown in FIG. 7F, the deformable member 784 can be inserted into or embedded within a middle portion of the enclosure 780. For example, the enclosure 780 can have an upper portion and a lower portion, and the deformable member 784 can be sandwiched between the upper portion and the lower portion. In some examples, the enclosure 780 can have an aperture 778, which exposes at least a middle portion of the deformable member 784.

The deformable member 784 can have a coupling mechanism configured to receive a suture (not shown). In the depicted example, the deformable member 784 has a middle neck portion 772 and two end portions 774. The middle neck portion 772 is narrower than the two end portions 774. Thus, when inserted into or embedded within the enclosure 780, the middle neck portion 772 can be exposed through the aperture 778, and two openings 776 can be formed on both sides of the middle neck portion 772. Thus, a suture can loop through a top surface of the middle neck portion 772 through the openings 776. In other examples, the coupling mechanism can be configured differently, e.g., by using one or more apertures located on the deformable member 784, by using hooks or adhesives, etc.

Thus, when a tensile force is applied to the suture that is coupled to the deformable member 784, the deformable member 754 can deform as a result. The deformation of the deformable member 784 can in turn cause changes in characteristics of the resonant circuit, e.g., by changing the resistance of the strain gauge 786 which is attached to the deformable member 784. Thus, by measuring the resonant frequency of the resonant circuit, the tensile force applied to the suture can be obtained.

As another example, FIGS. 7D-7E depicts a suture button assembly 740, which includes a conventional/non-sensorized suture button 742, and a sensorized suture button adaptor 744 configured to receive the suture button 742. The suture button 742 can be any off-the-shelve suture button which has no embedded electronics. The suture button 742 can be configured to have any shape and/or size. A suture 746 can be attached to the suture button 742, e.g., through one or more apertures 748. In this example, the suture button assembly 740 can be configured as an implantable sensor and the suture button adaptor 744 can be deemed as a sensor assembly which includes a substrate (e.g., a deformable member 754) and a resonant circuit coupled to the substrate.

The suture button adaptor 744 can be sensorized by embedding a resonant circuit (similar to 620 or 720). In the depicted example, the suture button adaptor 744 includes an enclosure 750, an inductor 752, a deformable member 754, a strain gauge 756, and a capacitor 758. The inductor 754, the capacitor 758, and the strain gauge 756 can be electrically connected so as to form a resonant circuit similar to 720. In some examples, the strain gauge 756 can be optional, thus forming a resonant circuit similar to 620. For example, the capacitor 758 can comprise two opposing conductive plates (similar to 626*a*, 626), one of which is connected to the deformable member 754 whereas the other is spaced away from the deformable member 754.

The enclosure 750 can comprise a polymeric material and/or a metallic material. In some examples, the enclosure 750 can be configured to enclose and/or encapsulate the inductor 752, the deformable member 754, the strain gauge 756, and the capacitor 758. For example, the inductor 752 can be placed along an inner wall of the enclosure 750. In some examples, more than one inductor 752 can be placed within the enclosure 750. The deformable member 754 has a predefined flexural modulus so that it can deform within a certain range under a force loading. In some examples, the deformable member 754 can comprise a bendable metal and/or a metallic alloy. In some examples, the deformable member 754 can comprise a compliant polymeric material. The deformable member 754 can also be placed within the enclosure 750. In one example, one or more sides of the deformable member 754 can press against the inductor 752. The strain gauge 756 and the capacitor 758 can be placed anywhere within the enclosure 750. In one particular example, the strain gauge 756 and the capacitor 758 can be disposed on a bottom surface of the deformable member 754.

The enclosure 750 can have an upper opening 760 that matches the shape/size of the suture button 742. Thus, the suture button 742 can be inserted through the opening 760 until the suture button 742 contacts a top surface 762 of the deformable member 754. The deformable member 754 can include one or more apertures 764 through which the suture 746 can extend downwardly. Thus, a tensile force applied to the suture 746 can be transferred (through the suture button 742) to the deformable member 754. As a result, the deformable member 754 can deform responsive to the tensile force. For example, in the depicted configuration, when pulling the suture 746 in a downward direction relative to the suture button 742, a middle portion of the deformable member 754 surrounding the apertures 764 (where the suture 745 passes through) can bend downwardly relative to two end portions of the deformable member 754. The deformation of the deformable member 754 can in turn cause changes in characteristics of the resonant circuit, e.g., by changing the resistance of the strain gauge 756 which is attached to the deformable member 754. Thus, by measuring the resonant frequency of the resonant circuit, the tensile force applied to the suture can be obtained.

Example Suture Anchors Embedded with an LCR Resonant Circuit

Figure 8A:
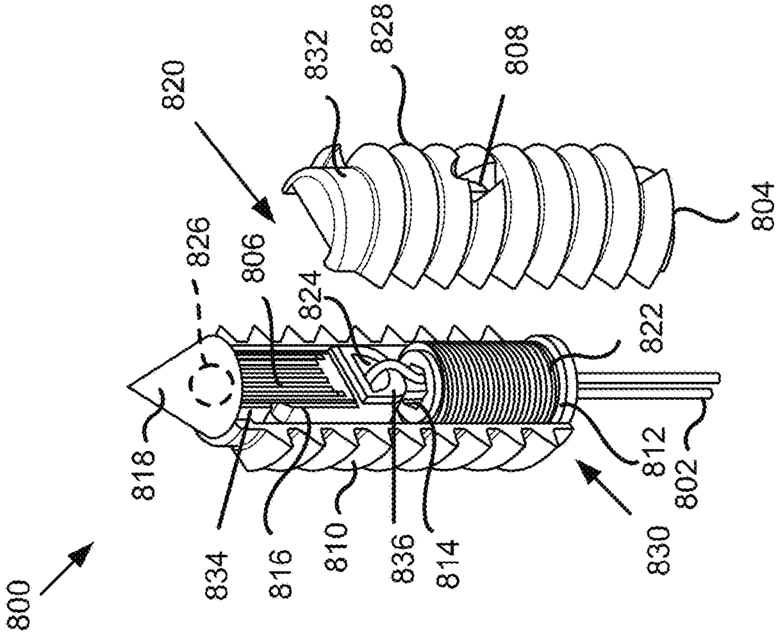
FIG. 8A depicts a suture anchor including a strain gauge, according to one example.
Figure 8D:
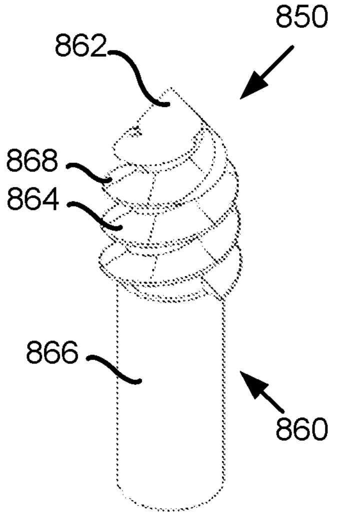
FIG. 8D depicts a suture anchor, according to another example.

FIG. 8A (not drawn to scale) schematically depicts a suture anchor 800 that can be connected to a suture 802, according to one example. The loose ends of the suture 802 can be connected to a biological tissue (not shown). The suture anchor 800 can be sensorized by embedding a resonant circuit 820 therein. Thus, the suture button 800 can be configured as an implantable sensor (which can also be referred to as a sensor assembly). The suture anchor 800 can be the suture anchor 500 described above.

The suture anchor 800 has a substrate 830 and the resonant circuit 820 is coupled to the substrate 830. In the depicted example, the resonant circuit 820 is also an LCR resonant circuit comprising at least one capacitor 826, at least one inductor 822, and a strain gauge 806 having a resistance that varies in response to a deformation of the strain gauge 806. The inductors 822, the capacitor 826, and the strain gauge 806 can be connected in series, forming a resonant circuit that can also be represented by the circuit diagram depicted in FIG. 8B. Thus, the same principles described above for detecting suture tension (which causes deformation of the strain gauge 806) based on the measurement of resonance quality factor at the resonant frequency also apply to the suture anchor 800.

In the depicted example, the substrate 830 includes an enclosure 810 having a generally conic tip portion 818 and a body portion 832 connected to the tip portion 818. The body portion 832 has a generally cylindrical shape. In addition, the body portion 832 can have a plurality of external threads 828 formed over at least a portion of the body portion 832 so as to facilitate screwing the suture anchor 800 into an anchoring body (e.g., a bone). An end of the body portion 832 opposite to the tip portion 818 can have an opening 804 through which the suture 802 can exit from the enclosure 810. Optionally, the enclosure 810 can have another opening which extends through a side wall of the body portion 832 to allow access to the suture 802 located inside the enclosure 810 (e.g., to adjust attachment of the suture 802 to the substrate 830 or for other purposes). Similarly, the enclosure 810 can be made of a biocompatible material and/or covered with a layer of Parylene-C coating. In some examples, the enclosure 810 can comprise a plastic material and/or polymeric material.

The substrate 830 can include a spring 816 disposed inside the enclosure 810. For example, one end 834 of the spring 816 can be fixedly attached to the tip portion 818 and the body of the spring 816 can extend axially within an inner lumen of the body portion 832. The strain gauge 806 can be fixedly attached (e.g., by gluing using epoxy resin, another adhesive, or other fastener or attachment mechanism) to the spring 816. Thus, axial elongation or compression of the spring 816 can cause corresponding elongation or compression of the strain gauge 806, thus changing its resistance.

In certain examples, the conic tip portion 818 and the spring 816 can be formed as a unitary piece. For example, the conic tip portion 818 can be a part of the spring 816 and rest over an end of the body portion 832.

In certain examples, the body portion 832 can have an axial length ranging from about 2 mm to about 8 mm (e.g., 5 mm), and the diameter of the body portion 832 can range from about 3 mm to about 9 mm (e.g., 6 mm). In certain examples, the body portion 832 can be dual-threaded with a thread pitch ranging from about 1 mm to about 3 mm (e.g., 2 mm), a thread depth ranging from about 0.5 mm to about 1.5 mm (e.g., 1 mm), and a thread angle ranging from about 500 to about 80° (e.g., 66°).

The spring 816 can be fabricated with different geometric designs and/or different materials to control and/or optimize strain sensitivity of the suture anchor 800 for a particular application. As examples, the tensile stiffness of the spring 816 can be configured to range from about 4 N/m to about 40 N/m, and the flexural stiffness of the spring 816 can range from about 4 N/m to about 2.5 N/m. In one particular example, the spring 816 can be made of stainless steel.

Similar to 706, the strain gauge 806 can be fabricated from different materials to obtain specific properties. In one particular example, the strain gauge 806 can be a low resistance (e.g., between about 1Ω to about 30Ω) semiconductor strain gauge with a gauge factor between about 50 and about 200.

The substrate 830 can further include an inductor holder 812 enclosed by the body portion 832 of the enclosure 810. As depicted in FIG. 8A, the inductor holder 812 is generally coaxial with the body portion 832, and the inductor 822 can be wrapped around the inductor holder 812. In certain examples, the inductor 822 can have a diameter ranging from about 3 mm to about 4 mm (e.g., 3.45 mm). The inductor holder 812 has an inner lumen 814 through which the suture 802 can extend. The inner lumen 814 can have various cross-sectional shapes (e.g., circle, square, hexagonal, etc.). In certain examples, the largest cross-sectional dimension of the inner lumen can range from about 1 mm to about 3 mm (e.g., 2 mm). In addition, the spring 816 has an eyelet 824 located at an end 836 of the spring 816 that is distal to the tip portion 818. The eyelet 824 is sized so that the suture 802 can extend through. Thus, the suture 802 can be inserted into the enclosure 810 through the opening 804, through the inner lumen 814, and across the eyelet 824. The suture 802 can then extend through the inner lumen 814 in a reverse direction, and exit from the enclosure 810 through the opening 804. In certain examples, the suture 802 can loop through the eyelet 824 multiple times. In certain examples, knots or other fastening mechanisms can be used to attach the suture 802 more securely to the spring 816.

In the depicted example, increasing the suture tension in the downward direction (as in FIG. 8A) can elongate the spring 816 and the strain gauge 806 attached thereto in the axial direction, thus changing the resistance of the strain gauge 806. Alternatively, the spring 816 and the strain gauge 806 can be configured to be axially compressed in response to an increase in suture tension. For example, the end 836 of the spring 816 can be fixedly attached to the side wall of the body portion 832 whereas the end 834 of the spring 816 can be detached from the tip portion 818 (thus can freely move in the axial direction). The eyelet 824 for looping through the suture 802 can be located at the end 834 instead of 836. Thus, pulling the suture 802 in the downward direction (as in FIG. 8A) can axially compress the spring 816 and the strain gauge 806.

The capacitor 826 can be a surface mount capacitor (e.g., a monolithic ceramic capacitor, a film capacitor, etc.) that is embedded in any part of the substrate 830. In the depicted example, the capacitor 826 is embedded in the tip portion 818 of the enclosure 810. The capacitance of the capacitor 826 and the inductance of the inductor 822 can be selected based on particular applications. In one particular example, the inductance of the inductor 822 can range from about 1 μH to about 5 μH, and capacitance of the capacitor 826 can range from about 100 nF to about 400 nF. In certain examples, the resonant circuit 820 can have more than one capacitors and/or more than one inductors 822 embedded within the substrate 830. As noted above, the additional inductors and/or capacitors can be connected to any of the electrical components in the resonant circuit 820 in series and/or in parallel, thus resulting in different resonant frequencies of the resonant circuit 820.

Although FIG. 8A shows only one resonant circuit 820 in the suture anchor 800, it is to be understood that, in certain circumstances, multiple resonant circuits having different resonant frequencies can be embedded in the suture anchor 800. Thus, a single suture anchor 800 can embed multiple implantable sensors which can be simultaneously detected by a single detector (e.g., 160). Similarly, these multiple resonant circuits can be coupled to the same substrate 830 and configured to change respective resonant frequencies in response to the same or different deformations of the substrate 830. Alternatively, these multiple resonant circuits can be coupled to different substrates, each of which is configured to deform (e.g., to different extents and/or in different directions) in response to the tensile force applied by the suture 802.

Additional Examples of Suture Anchors

The suture anchors 800, 950 described above are merely two examples of implantable sensors. FIGS. 8D-8H depict another example of implantable suture anchor 850.

The suture anchor 850 includes an enclosure 860 having a generally conic tip portion 862, a screw portion 864 connected to the tip portion 862, and a non-screw portion 866 connected to the screw portion 864. The screw portion 864 has a plurality of external threads 868 configured to facilitate screwing the suture anchor 850 into an anchoring body (e.g., a bone). The non-screw portion 866 has a generally cylindrical shape and has no external threads.

To improve the strength of the suture anchor 850, instead of using plastic and/or polymeric materials which may break under a high pressure (e.g., during screwing), the tip portion 862 and/or the screw portion 864 can comprise substantially a metallic material, such as stainless steel, titanium, or a metallic alloy (e.g., the alloy can comprise two or more materials selected from the group consisting of iron, cobalt, chromium, titanium, and tantalum).

The suture anchor 850 can include a deformable member 870 connected to the screw portion 864. In the depicted example, the deformable member 870 is configured as an elongated plate and extends along a longitudinal axis of the suture anchor 850. In another example, the deformable member 870 can be configured as a coiled or non-coiled spring. The deformable member 870 can have a coupling mechanism 872 configured to receive a suture 852. For example, an end portion of the deformable member 870 can have an aperture or a hook configured for the suture 852 to extend through. In other examples, the suture 852 can be coupled to the deformable member 870 via other means, e.g., by using adhesives, etc.

The deformable member 870 can comprise a metallic material that is similar to or the same as the material forming the tip portion 862 and/or the screw portion 864. In certain examples, the tip portion 862, the screw portion 864, and the deformable member 870 can be constructed as a unitary object (e.g., through laser cutting, metal injection molding, etc.). The deformable member 870 has a predefined flexural modulus so that it can deform within a certain range under a force loading. For example, when the suture 852 coupled to the deformable member 870 is pulled downwardly, the deformable member 870 can elongate in the longitudinal direction. The deformable member 870 can return to its original length when the tensile force on the suture 852 is removed.

Figure 8E:
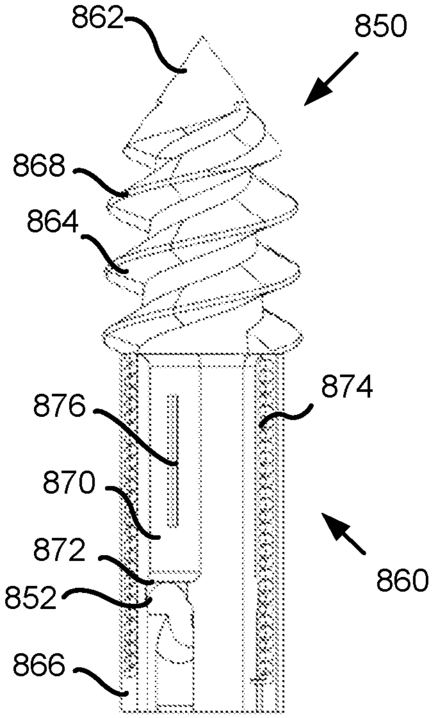
FIG. 8E shows a longitudinal cross-section of a non-screw portion of the suture anchor of FIG. 8D.
Figure 8F:
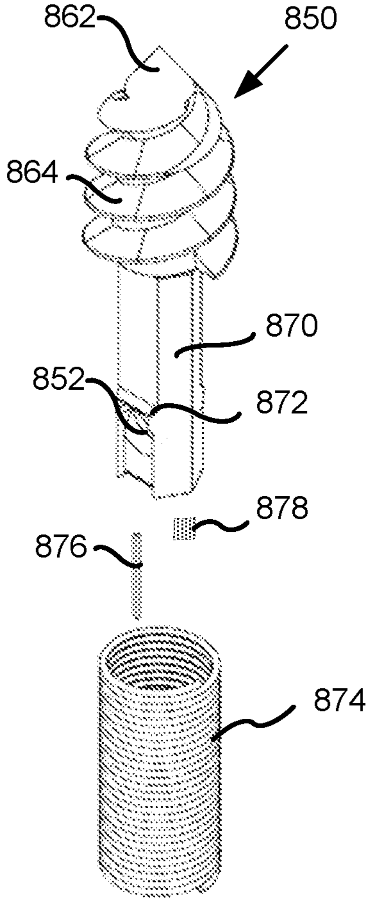
FIG. 8F shows an exploded view of the suture anchor of FIG. 8D.

Similar to 800 and 950, the suture anchor 850 includes a resonant circuit embedded within the enclosure 860. In the depicted example, the resonant circuit (similar to 720) is formed by an inductor coil 874, a strain gauge 876, and a capacitor 878. As depicted in FIG. 8E, the deformable member 870 can be inserted into the inductor coil 874, which is enclosed within a lumen of the non-screw portion 866. The strain gauge 876 can be attached to a surface of the deformable member 870 and extend in a direction that is parallel to the longitudinal axis of the suture anchor 850. The capacitor 878 can be placed anywhere within the enclosure 860. For example, the capacitor 878 can be disposed on any surface area of the deformable member 870. In some examples, the strain gauge 876 can be optional, thus forming a resonant circuit similar to 620. For example, the capacitor 878 can comprise two opposing conductive plates (similar to 626*a*, 626), one of which is connected to the deformable member 870 whereas the other is located at a fixed position (relative to the non-screw portion 866) within the enclosure 860. The non-screw portion 866 can comprise a non-metallic material (e.g., a plastic/polymeric material, etc.) so as not to create a metallic shield around the resonant circuit, thereby allowing the transmission of electromagnetic signals across the enclosure 860.

Thus, when a tensile force is applied to the suture 852 that is coupled to the deformable member 870, the deformable member 870 can deform (e.g., elongate in the longitudinal direction) as a result. The deformation of the deformable member 870 can in turn cause changes in characteristics of the resonant circuit, e.g., by changing the resistance of the strain gauge 876 that is attached to the deformable member 870. Thus, by measuring the resonant frequency of the resonant circuit, the tensile force applied to the suture 852 can be obtained.

Figure 8G:
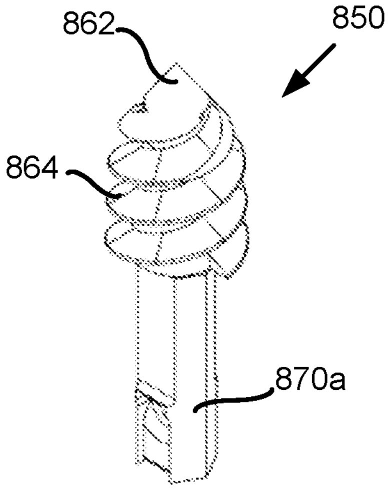
FIG. 8G-8H show two examples of a deformable member of the suture anchor of FIG. 8D.
Figure 8H:
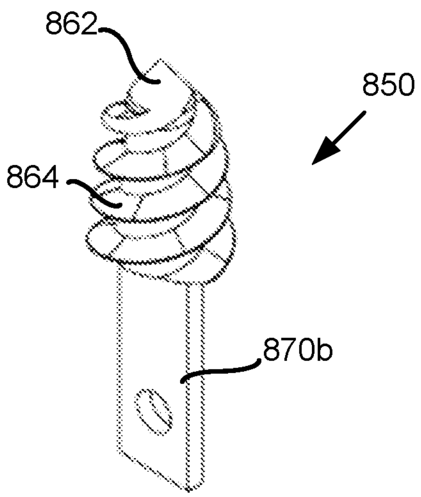

The flexural modulus of the deformable member 870 can be adjusted so as to achieve different deformation characteristics. Such adjusting can be achieved, for example, by choosing different materials for the deformable member 870, and/or adjusting dimension of the deformable member 870. For example, FIGS. 8G and 8H show two different designs of deformable member 870*a*, 870*b* comprising the same material. The deformable member 870*a* of FIG. 8G is thicker than the deformable member 870*b* of FIG. 8H. As a result, the deformable member 870*b* can deform to a greater extent than the deformable member 870*a* under the same force loading. Thus, a greater resonant response (and a greater sensitivity) can be achieved for a suture anchor using the deformable member 870*b* than using the deformable member 870*a*.

Example Variant Resonant Circuits

Although specific resonant circuits 620, 720, 820 are described above, it is to be understood that the implantable sensor, whether it is a sensorized suture button/anchor or any other sensorized suture attachment devices, can have different designs based on the same principles described herein. Two such examples are described below for illustrative purposes.

Figure 9B:
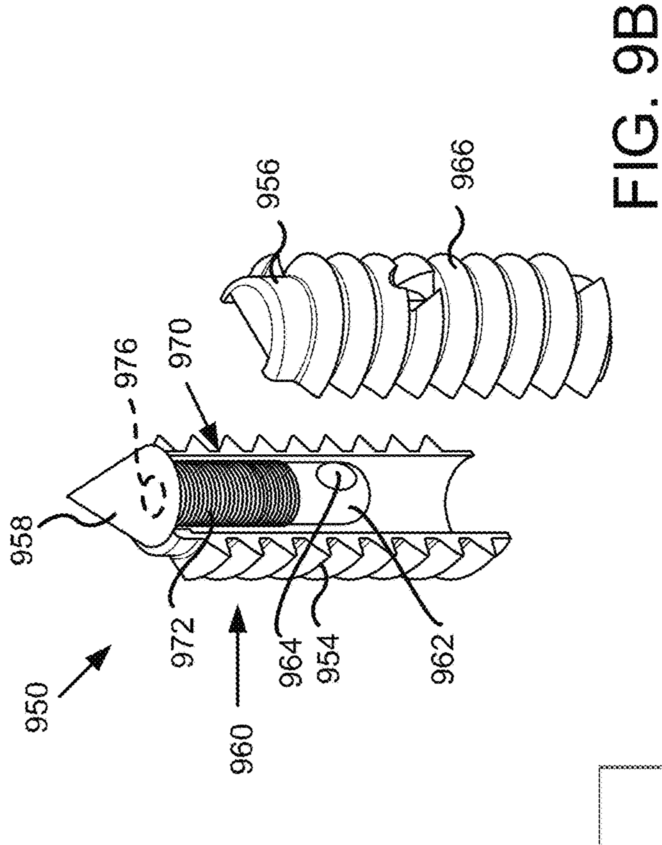
FIG. 9B depicts a suture anchor including a deformable inductor, according to one example.
Figure 9C:
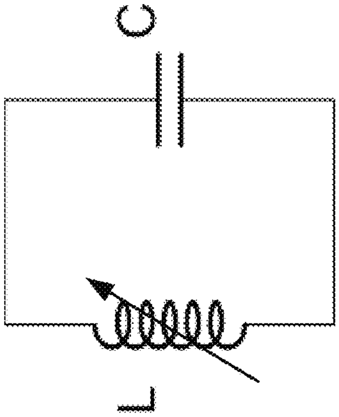
FIG. 9C depicts a circuit diagram of a resonant circuit embedded in the suture button of FIG. 9A or suture anchor of FIG. 9B.
Figure 9A:
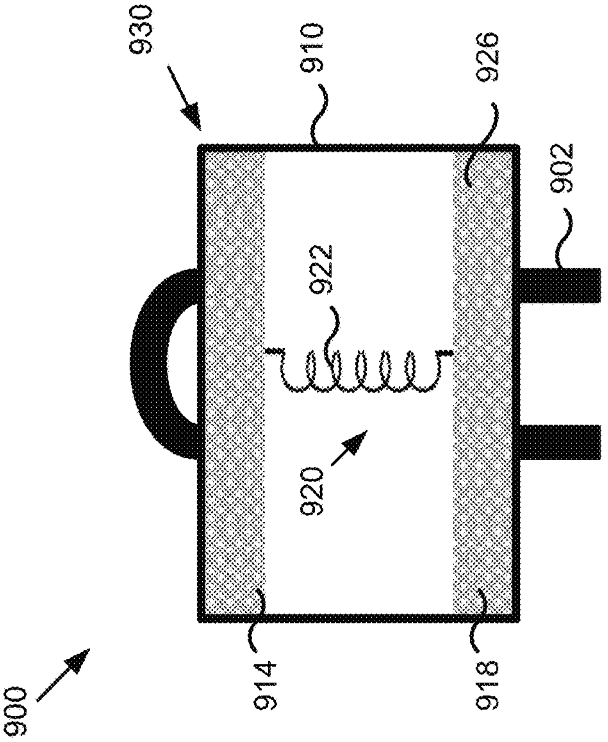
FIG. 9A schematically illustrates a cross-sectional view of a suture button, according to another example.

FIG. 9A (not drawn to scale) schematically depicts another example suture button 900 that can be connected to a suture 902. The suture button 900 has a substrate 930 and a resonant circuit 920 coupled to the substrate 930. The substrate 930 includes an enclosure 910 and two plates 914, 918 encased by the enclosure. The suture 902 can be connected to the substrate 930 using similar attachment mechanisms as described above in reference to FIG. 6B.

In the depicted example, the resonant circuit 920 is an LC resonant circuit including at least one capacitor 926 and at least one inductor 922 that are connected in series. The capacitor 926 can be a surface mount capacitor similar to 726 or 826 that is disposed within the enclosure 910 (e.g., embedded within the plate 918 or 914). The inductor 922 can be a spring coil inductor extending between and connecting the two plates 914, 918. Deformation of the enclosure 910 via a tensile force applied to the suture 902 can change the distance between the two plates 914, 918, thereby varying the length of the inductor 922. For example, the length of the spring coil inductor is shortened when the two plates 914, 918 are moving close to each other and lengthened when the two plates 914, 918 are moving away from each other. As a result, the inductance of the inductor 922 can change accordingly.

A circuit diagram of the resonant circuit 920 is shown in FIG. 9C, which shows the capacitor 926 having a constant capacitance C and the inductor 922 having a variable inductance L. The conductor resistance is considered negligible and not shown. Similar to the LC resonant circuit 620 described above, the resonant frequency of the resonant circuit 920 can be calculated based on L and C. Thus, by measuring the resonant frequency of the resonant circuit 920, the length of the inductor 922 and the suture tension can be determined.

FIG. 9B (not drawn to scale) schematically depicts another example suture anchor 950 that can be connected to a suture. The suture anchor 950 has a substrate 960 and a resonant circuit 970 coupled to the substrate 960.

Similar to 800, the substrate 960 includes an enclosure 954 comprising a conic tip portion 958 and a generally cylindrical body portion 956 which has external threads 966. In the depicted example, the resonant circuit 970 is an LC resonant circuit including at least one capacitor 976 and at least one inductor 972 that are connected in series. The capacitor 976 can be a surface mount capacitor similar to 726 or 826 that is disposed within the enclosure 954 (e.g., embedded within the tip portion 958). The inductor 972 can be a spring coil type (e.g., similar to 922) having an inductance that varies in response to a deformation of the inductor 972. Thus, the resonant circuit 970 can also be represented by the circuit diagram of FIG. 9C.

As depicted in FIG. 9B, the substrate 960 can include an inductor holder, such as a spring 962, disposed inside the enclosure 954. For example, one end of the spring 962 can be fixedly attached to the tip portion 958 and the body of the spring 962 can extend axially within an inner lumen of the body portion 956. The inductor 972 can be wrapped around the spring 816. Thus, axial elongation or compression of the spring 962 can cause corresponding elongation or compression of the inductor 972, thus changing its inductance. Similarly, the suture can be connected to the substrate 960 by looping through an eyelet 964 on the spring 962. Thus, varying suture tension can cause axial movement of the spring 962 and the inductor 972, thereby changing the inductance of the inductor 972 and the resonant frequency of the resonant circuit 970. Accordingly, by measuring the resonant frequency of the resonant circuit 970, the length of the inductor 972 and the suture tension can be determined.

Many other variants of the resonant circuits can be embedded in the implantable sensor based on the same principles described herein. As noted above, in certain examples, additional capacitors, inductors, and/or resistors can be added to the resonant circuit. These additional electrical components can be connected to existing circuit components in the resonant circuit in series and/or in parallel. Despite such variations, these resonant circuits are essentially LC (or LCR) resonant circuits having characteristic resonant properties. For example, the resonant frequency of a resonant circuit can be dependent on the inductance of all inductors and capacitance of all capacitors in the circuit, and the resonance quality factor of the resonant circuit can be further dependent on the resistance of all resistors in the circuit.

In the examples described above, the resonant circuit is configured to have only one electrical component that varies its electrical parameter in response to a deformation of the substrate to which the resonant circuit is attached. For example, in FIG. 6B, only the capacitance of the capacitor 626 changes in response to the deformation of the substrate 630. In FIGS. 7A-7C and 8A, only the resistance of the strain gauge 706 or 806 changes in response to the deformation of the substrate 730 or 830. In FIGS. 9A-9B, only the inductance of the inductor 922 or 972 changes in response to the deformation of the substrate 930 or 960. Nonetheless, it is to be understood that in certain circumstances, more than one electrical components (e.g., capacitors, inductors, resistors) can change their respective electrical parameters (e.g., capacitance, inductance, resistance) in response to the deformation of the substrate. So long as the resulting resonant parameters (e.g., resonant frequency and/or resonance quality factor) can be properly calibrated with the suture tension that causes the deformation of the substrate, such resonant circuit can be embedded in an implantable sensor connected to a suture to measure the tensile force applied to the suture.

Example Detection Device for Suture Buttons and Suture Anchors

The implantable sensors described above (e.g., 600, 700, 800, 900, 950) can be remotely monitored through an externally placed a detector (e.g., 320, 420, 520) having a detection coil (e.g., 322, 422, 522), which inductively couples with at least one inductor (e.g., 622, 624, 722, 822, 922, 972) embedded in the implantable sensor. When the detection coil and the inductor are inductively coupled, the total impedance measured from the coil antenna ($Z_T$) becomes:

$$Z_T = Z_D + \frac{\omega^2 M}{Z_S} \tag{4}$$

where $Z_D$ is the impedance of the detection coil, ω is the radian frequency, M is the mutual inductance coupling, and $Z_S$ is:

$$Z_s(j\omega) = r + R_s + j(X_L - X_C) \tag{5}$$

where $X_L$ and $X_C$ are the implantable sensor's inductive and capacitive reactance, respectively, r is the conductor resistance in the sensor, and $R_s$ is the resistance of the strain gauge (e.g., 706, 806) if it is included in the resonant circuit of the implantable sensor. As noted above, the impedance $Z_S$ is minimum when the capacitive reactance and inductive reactance cancel each other out (i.e., $X_L = X_C$). This happens at the resonant frequency of the resonant circuit embedded in the implantable sensor given by equation (1) above. Also as noted above, the resonance quality factor of the resonant circuit can be determined using equation (3) above based on the conductance, inductance, and resistance of the resonant circuit. Thus, based on impedance measurement, the detector can measure the resonant circuit's resonant parameters (e.g., resonant frequency and/or resonance quality factor) which vary in response to a deformation of a substrate due to suture tension, based on which the tensile force applied to the suture can be determined.

Figure 10:
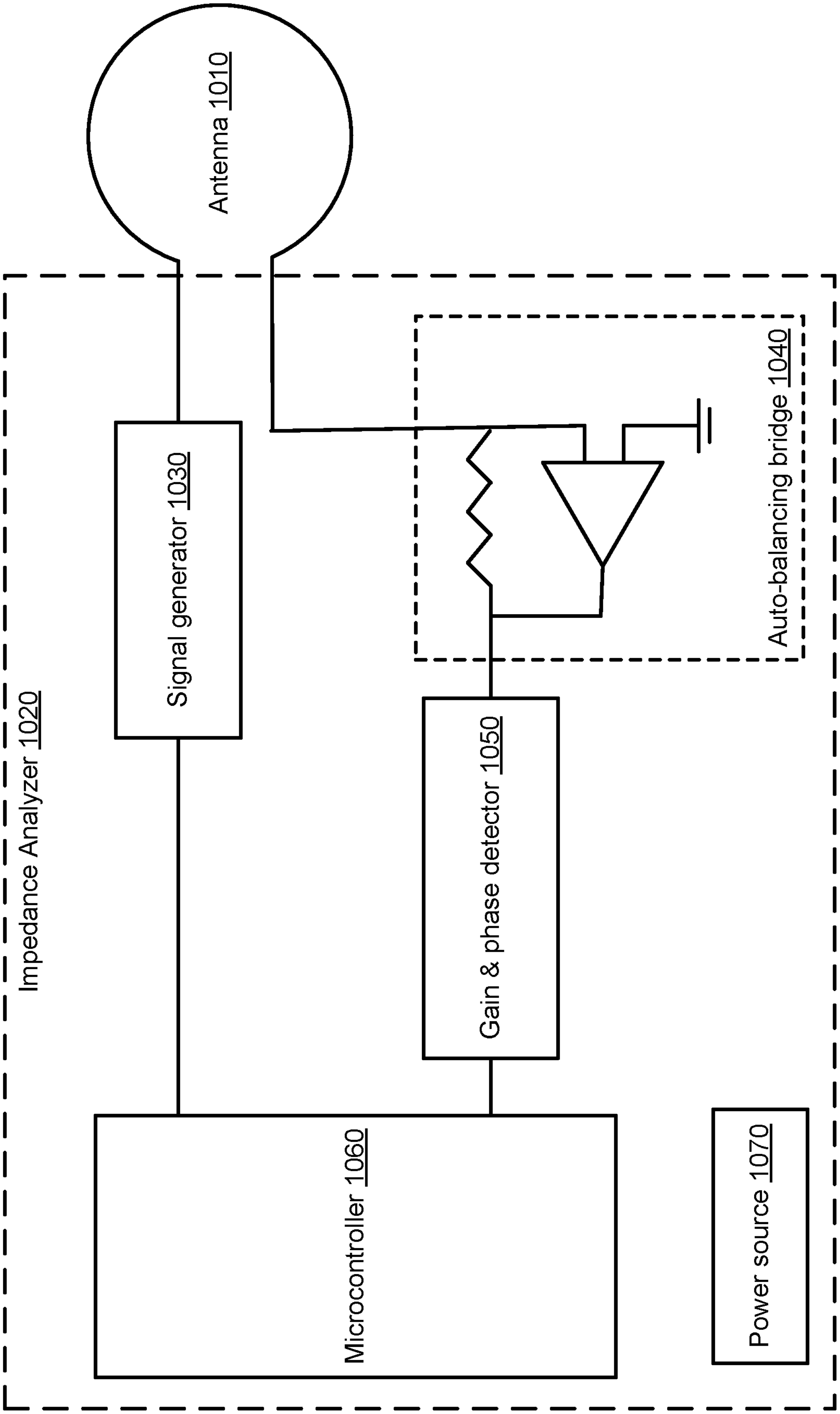
FIG. 10 is a block diagram of an example circuit for a detection device configured to measure a tensile force applied to a suture that is connected to an implanted sensor.

FIG. 10 is a block diagram of an example circuit 1000 for a detection device configured to measure a tensile force applied to a suture that is connected to an implanted sensor (e.g., 600, 700, 800, 900, 950). The circuit 1000 can be embedded in any one of the detectors 320, 420, 520 described above.

As shown, the circuit 1000 includes an antenna 1010 configured to inductively couple with an inductor in the implantable sensor and an impedance analyzer 1020 configured to measure the impedance of the antenna 1010. The antenna 1010 can be any one of the detection coils 322, 422, 522 described above. In certain examples, the antenna 1010 can be a planar, multi-turn coil antenna made of copper magnetic wire. The impedance analyzer 1220 can be included in any of the electronics 324, 424, 524 described above. The antenna 1010 can be spaced apart from the impedance analyzer 1020 (as illustrated in FIGS. 3B, 4B, and 5A), but electrically connected to the impedance analyzer 1020 via wires.

The impedance analyzer 1020 can include a signal generator 1030, an auto-balancing bridge 1040, a gain and phase detector 1050, and a microcontroller 1060. In addition, the impedance analyzer 1020 can have a power source 1070 configured to provide electrical power to the circuit 1000. In certain examples (e.g., when the detector is a wearable device), the power source 1070 can include one or more batteries (which can be rechargeable). In certain examples, the power source 1070 can include circuitry configured to receive electrical power from an external power supply.

The microcontroller 1060 can be configured to control all operations of the circuit 1000, such as generation of excitation signal, detection of the secondary field generated by an implantable sensor, extraction of the impedance spectrum, calculation of the resonant parameters (e.g., resonant frequency and/or resonance quality factor), determination of the suture tension, etc. For simplicity, certain computing components associated with the microcontroller 1060, such as memories, input/output interfaces, buses, etc., are not shown in the block diagram, and more detailed description of example computing systems are described further below.

Under the control of the microcontroller 1060, the signal generator 1030 can be configured to generate an excitation signal (e.g., a sinusoidal wave) to produce an excitation electromagnetic field via the antenna 1010. The microcontroller 1060 can be configured to modulate a frequency of the excitation signal so that the excitation signal can sweep a frequency spectrum that contains the resonant frequency of the resonant circuit of the implantable sensor. In certain examples, the generated excitation signal can have a frequency up to 100 MHz or higher.

In use, the antenna 1010 can be placed at close proximity from the implantable sensor (for example, within a distance of less than 4 cm, e.g., about 2 cm) to capture the secondary electromagnetic field generated by the resonant circuit embedded in the implantable sensor through inductive coupling between the antenna 1010 and an inductor of the implantable sensor. The resonance spectrum of the implantable sensor can be extracted from the measured impedance spectrum. As noted above, multiple implantable sensors can be simultaneously detected even when they are in close proximity among each other by changing the designs so they resonate at different resonant frequencies.

The auto-balancing bridge 1040 can be configured to condition the signal to the antenna for impedance measurement. The gain and phase detector 1050 (which can operate in the radio frequency) can be configured to digitize the impedance of the antenna and measure a magnitude response and a phase response over the frequency spectrum based on the captured secondary electromagnetic field. In certain examples, amplifiers and/or pre-amplifiers can be used to boost the measured impedance signal and filter out measurement noise.

Figure 11:
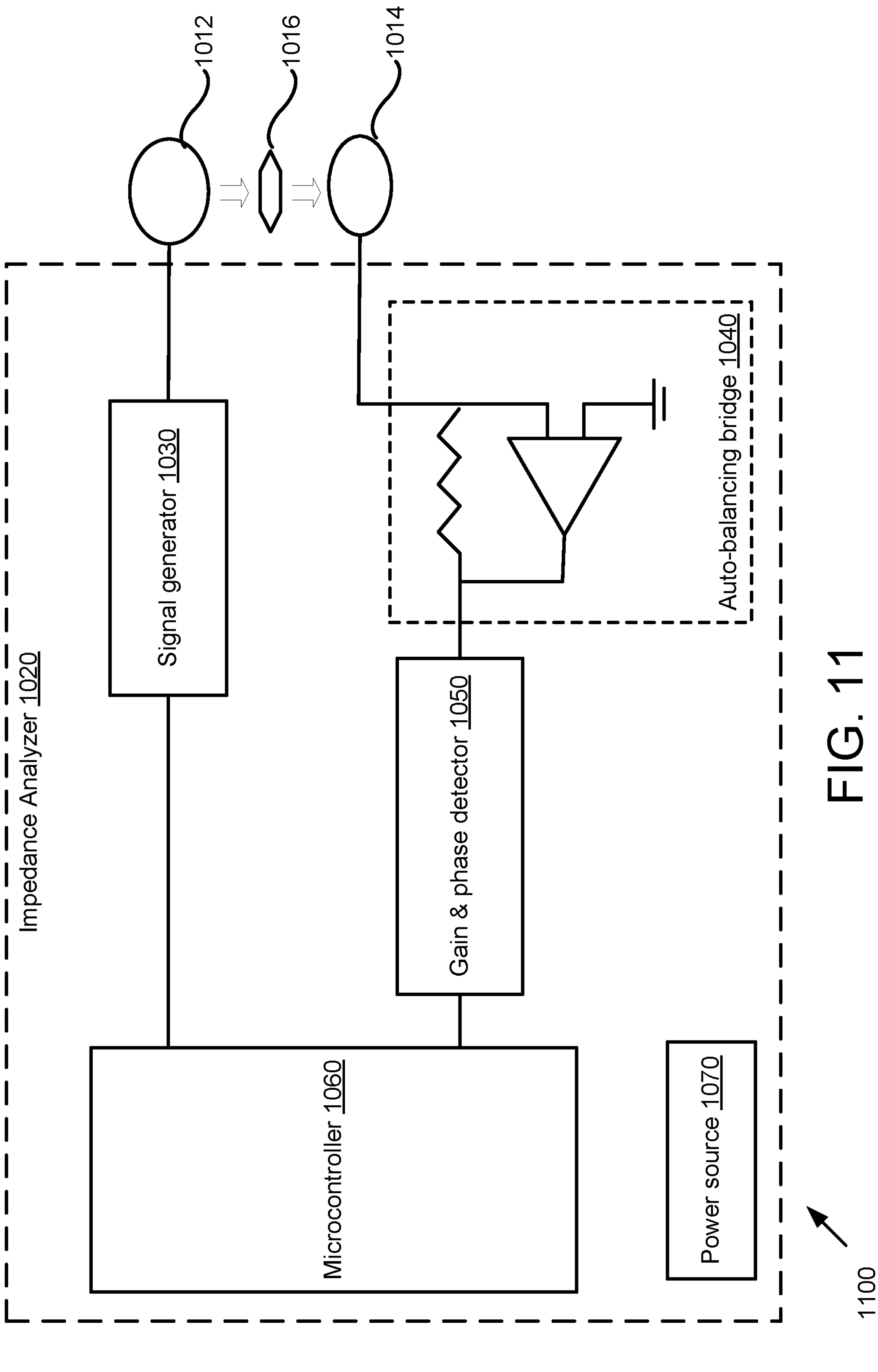
FIG. 11 is a block diagram of another example circuit for a detection device configured to measure a tensile force applied to a suture that is connected to an implanted sensor.

In certain examples, the resonant circuit can include multiple antennas. For example, one antenna can be used to generate an excitation electromagnetic field to activate the implantable sensor, while a second antenna can be used to capture the secondary electromagnetic field signal emitted from the implantable sensor. This can be illustrated in FIG. 11, which shows a block diagram of another example circuit 1100 that is similar to the circuit 1000 except that the impedance analyzer 1020 is connected to two antennas 1012, 1014. Specifically, the first antenna 1012 (also referred to as a "drive coil") is connected to the signal generator for generation of an excitation electromagnetic field, which can activate an implantable sensor 1016 (e.g., 600, 700, 800, 900, 950). The second antenna 1014, which is connected to the auto-balancing bridge 1040, can pick up the secondary electromagnetic field emitted from the implantable sensor 1016. In certain examples, the first and second antennas 1012, 1014 can be configured to be concentric and one is sized to have a slightly larger diameter than the other so that these two antennas can be placed generally coplanar.

Note that the detection device described herein can also be used for pledget sensors described further below.

Example Calibration of the Implantable Sensors

Any of the implantable sensors described above (e.g., 600, 700, 800, 900, 950) can be calibrated to obtain sensor-specific resonant characteristics.

Figure 12A:
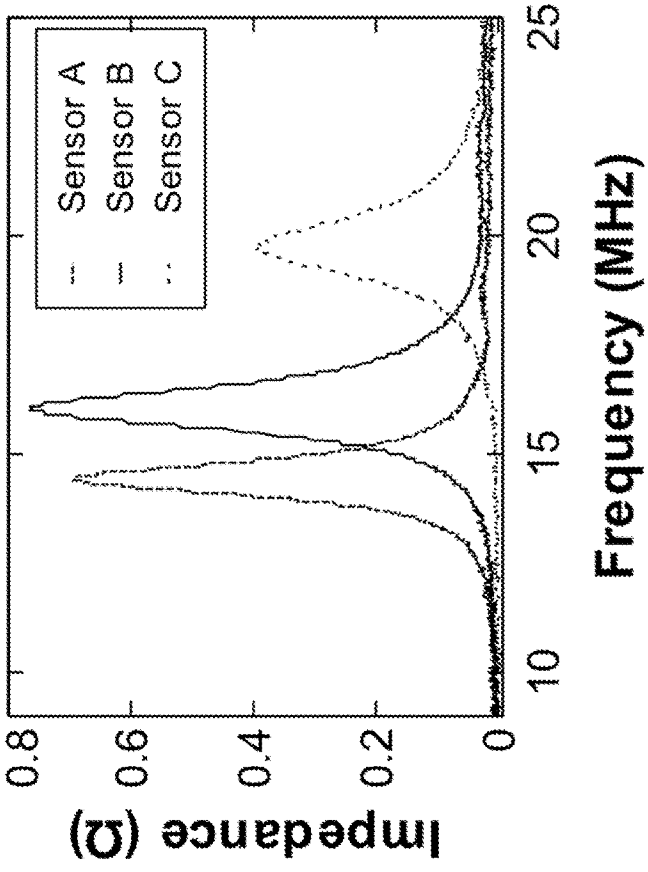
FIG. 12A depicts resonant responses of three different implantable sensors.

As an example, FIG. 12A depicts resonant responses of three different implantable sensors A, B, and C when exposed to an excitation electromagnetic field. In this particular example, the three implantable sensors A, B, C have the same structure as the suture anchor 800 depicted in FIG. 8A but are fabricated using different springs 816 (e.g., with different materials, stiffness, and flexibility) and inductors 822 (e.g., with inductances of 2.58 μH, 2.6 μH, and 2.8 μH, respectively). As shown, the three implantable sensors A, B, and C resonates at 14.4 kHz, 16.1 kHz, and 19.8 kHz, respectively. The resonance quality factors of three sensors A, B and C calculated from their respective resonance curves are 20.75, 23.81, and 18.27, respectively. The differences in the resonant frequency and resonance quality factor of these implantable sensors are due to the variations in inductance of the sensor as indicated by equation (3). The strain sensitivities of these three implantable sensors are not affected by the resonant frequencies and the resonance quality factors because the sensitivity is dependent on the gauge factor of the strain gauge 806 and the hardness of the spring 816.

Figure 12B:
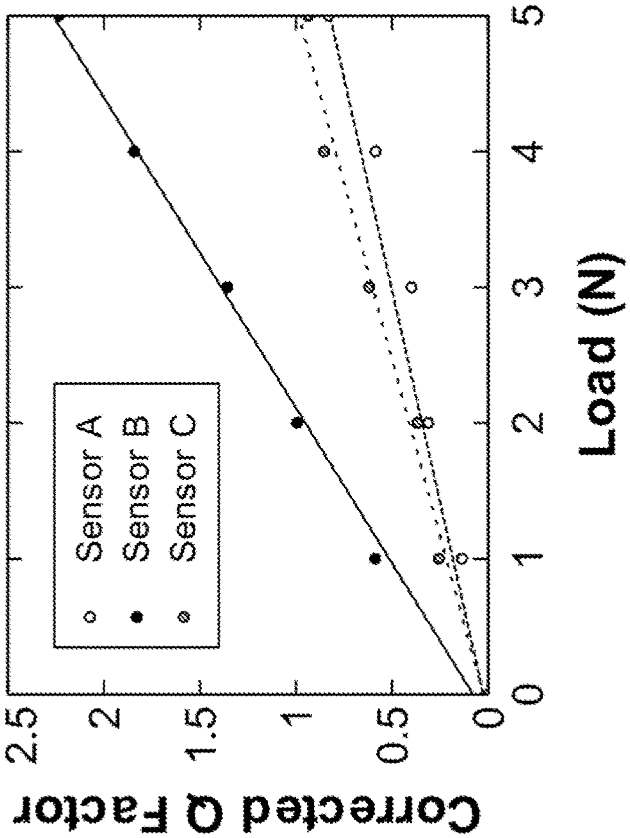
FIG. 12B depicts change of resonance quality factor for the three implantable sensors under different force loading conditions.

FIG. 12B depicts change of resonance quality factor (i.e., Q factor) for the three implantable sensors A, B, and C under different force loading conditions. As shown, loading magnitude ranging from 0 N to 5 N is applied to each implantable sensor and the corresponding resonance quality factor is measured. The curve corresponding to each implantable sensor can be used as a calibration curve that characterizes a relationship between the resonance resonant parameter (e.g., the resonance quality factor in this example) of the resonant circuit and a tensile force applied to the suture. The calibration curves can be pre-obtained via experiments in controlled settings and stored in a computer readable media. In the depicted example, a generally linear relationship between the resonance quality factor and the applied suture tension (within the depicted range of tensile force) is obtained for each implantable sensor. More generally, it is to be understood that a calibration curve charactering the relationship between a resonant parameter and the suture tension needs not to be linear so long as it can be used to convert the measured resonant parameter to the measured tensile force applied by the suture based on such calibration curve.

FIG. 12B also shows that the sensitivities (e.g., measured based on the slopes of the calibration curves) of the three implantable sensors A, B, and C differ under different tensile forces. As shown, the implantable sensor B has a higher sensitivity of 0.44 $N^{-1}$ compared to 0.16 $N^{-1}$ and 0.19 $N^{-1}$ for implantable sensors A and C, respectively. Even though identical in design, the implantable sensor B is more sensitive than implantable sensor A because the spring material used in the implantable sensor B is more flexible than the implantable sensor C (e.g., flexural modular is 0.82 GPa for implantable sensor B versus 1.60 GPa for implantable sensor C). On the other hand, the springs of the implantable sensors B and A are made with the same material, but the design of the implantable sensor A makes it stiffer than that of implantable sensor B (e.g., in implantable sensor A, a thin layer of flap is added between gaps of the spring coils to increase the spring constant of the spring 816). As FIG. 12B illustrates, the sensitivity and operating frequency of the implantable sensors A, B, and C can be tuned for specific applications by changing spring constant of the spring 816 and the inductor value, separately. Similar principles of tuning resonant parameters can be applied to other types of implantable sensors described above.

Figure 13:
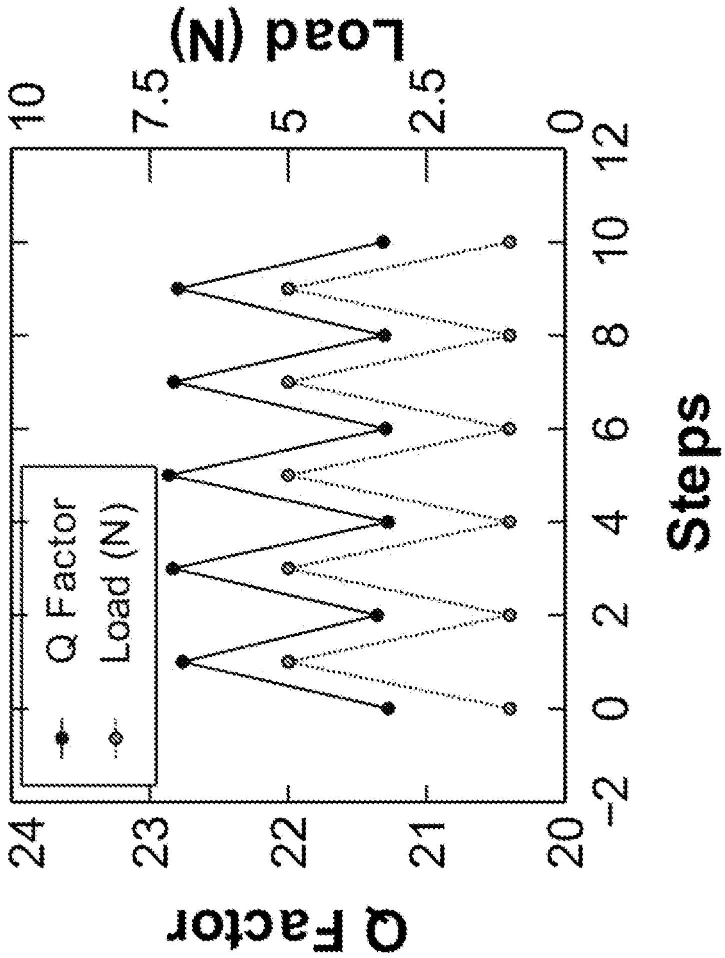
FIG. 13 depicts response of one implantable sensor when under repetitive loading cycles.

As an example, FIG. 13 depicts response of the implantable sensor B when under repetitive loading cycles (e.g., one loading cycle includes one step of increasing load followed by one step of decreasing load) with the loading magnitude varies between 1 N and 5 N. As shown, there is no noticeable drift or change in sensitivity after five loading cycles.

The signal amplitude and resonant parameters of the implantable sensors can also be measured as a function of a relative angle between the suture and implantable sensor to account for the effect of pulling direction. For example, investigations were performed to determine if the implantable sensors A, B, and C can provide accurate measurement when the suture was being pulled from a different angle between −32° and 32°, in parallel or in perpendicular to the width of the strain gauge 806. Experimental results show that the sensor response was within an error of 2 standard of deviation of the sensor response when the pulling angle is at 0°, and only slight deviation was observed with angle of pull in all the test conditions.

In addition, to ensure the implantable sensor can be accurately detected when the detection coil (e.g., 322, 422, 522) is not aligned with it, the sensor response can also be measured as a function of its relative orientation and position from the detection coil. Specifically, investigations were performed to create various axial displacements, radial displacements and relative angle changes between the implantable sensor A, B, and C and a detection coil. The experimental results indicate that when the normal axis of the implantable sensor was aligned with the normal axis of the detection coil, the Q factor of the implantable sensor was consistent when it was within a space of 20 mm along the normal axis of the coil and 15 mm along the radial axis of the coil. In addition, when the normal axis of the implantable sensor was misaligned with the detection coil's normal axis, the implantable sensor could still maintain its measurement accuracy for up to 50° of misalignment.

Although specific implantable sensors (e.g., A, B, and C) are described above to illustrate example calibration methods/results, it is to be understood that the sensor-specific resonant characteristics can also be calibrated for other implantable sensors described above based on the same principles described herein. For example, for an LC resonant circuit represented by FIGS. 6C and 9C, its calibration curve can be obtained by measuring the resonant frequency of the resonant circuit when the suture is applied to a tensile force of varying amplitudes. Sensitivity of the implantable sensor under different loading conditions, the effects of suture angle relative to the sensor, and/or the effects of misalignment between the sensor and the detection coil can also be determined using similar methods described above.

Example Pledget Sensors

Another specific example suture sensor, a pledget sensor 1600 (or simply "pledget," see, e.g., FIGS. 15A-15B and FIG. 16), is described herein. Although specific parameter values are described below, it is to be understood that those values are merely illustrative and different parameter values can be chosen based on design considerations.

Figure 14A:
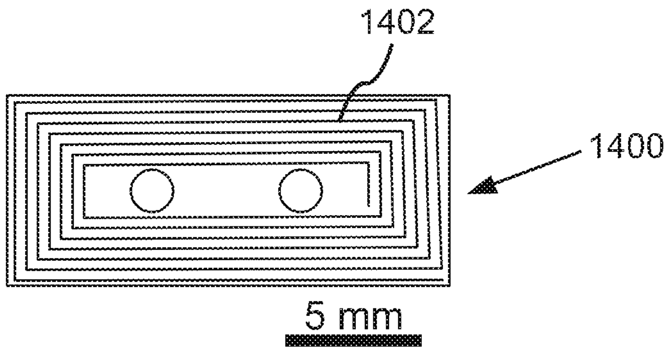
FIG. 14A shows a printed planar inductor coil on a flexible polyimide substrate, according to one example.
Figure 14B:
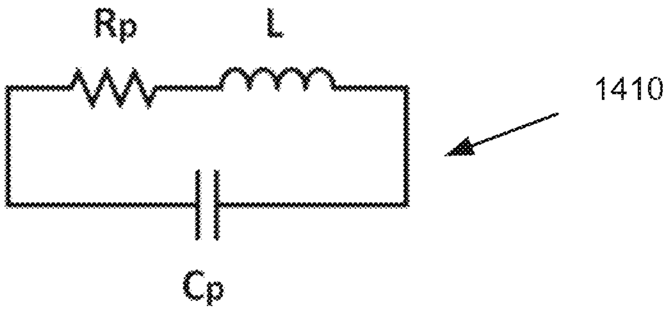
FIG. 14B shows an equivalent circuit diagram of a resonant circuit including the planar inductor coil of FIG. 14A (Rp=parasitic resistance, Cp=parasitic capacitance, L=inductance).
Figure 14C:
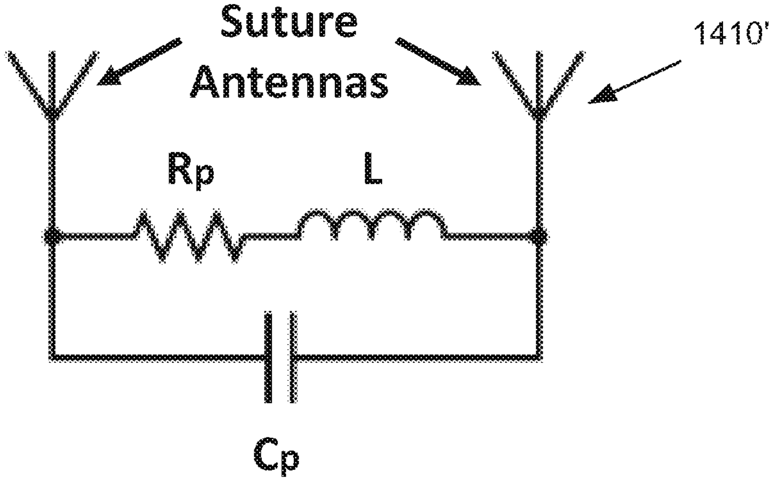
FIG. 14C shows another equivalent diagram of a resonant circuit including the planar inductor coil of FIG. 14B in connection with suture antennas, according to one example.
Figure 15A:
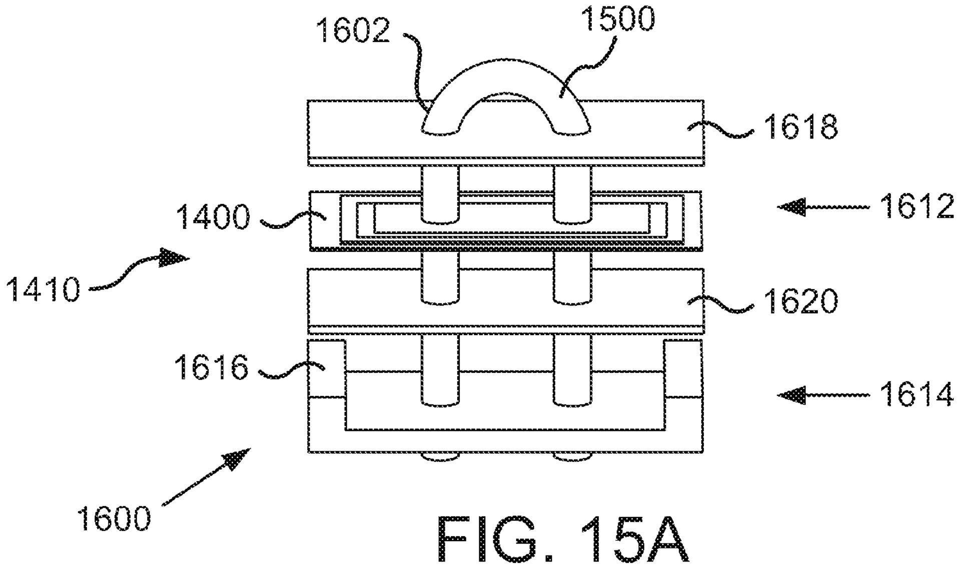
FIG. 15A depicts a CAD model showing a suture passing through an exploded view of pledget sensor components (PLA=polylactic acid, LC=inductor-capacitor).
Figure 15B:
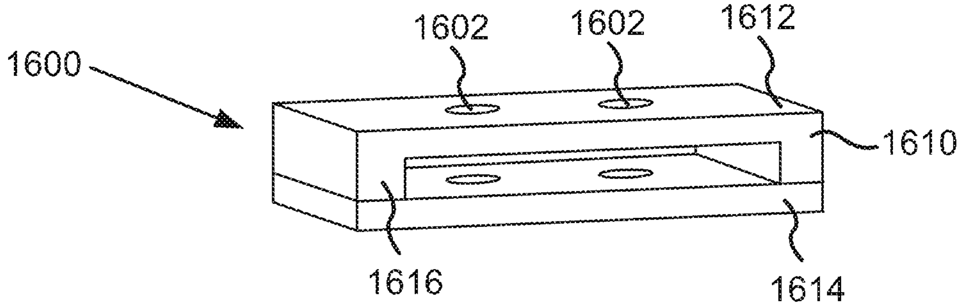
FIG. 15B shows suture pledget dimensions in the assembled CAD model, according to one example.
Figure 16:
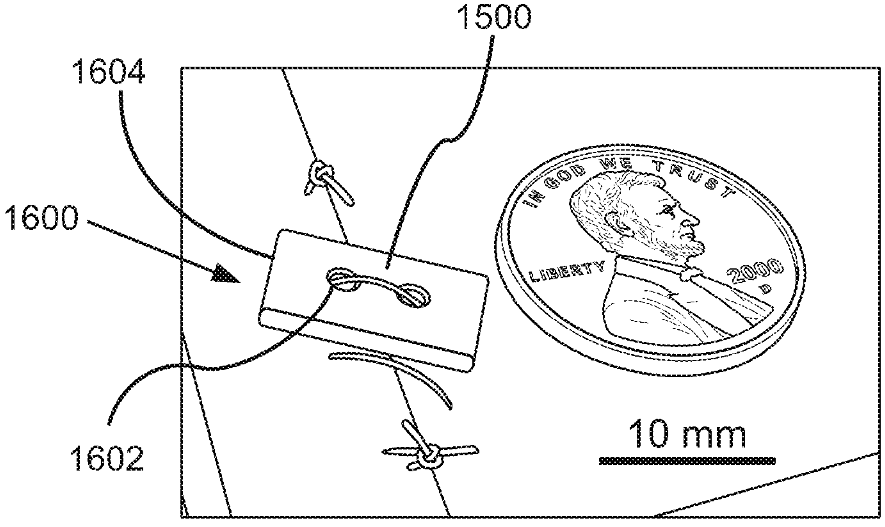
FIG. 16 depicts an image of an assembled pledget sensor incorporation in a basic continuous suture pattern.

In this specific example, the development of the pledget sensor 1600 began by modeling pledgets in computer aided drafting (CAD) software (Fusion 360; AutoDesk, San Rafael, CA) and 3D printing design components (Original Prusa i3 MK3S+; Prusa, Prague, Praha, Czech Republic) with polylactic acid (PLA; eSUN, Shenzhen, China). A 7-turn planar inductor coil 1402 was generated with circuit design software (Eagle; AutoDesk) and printed on a flexible polyimide substrate 1400 (Flex Printed Circuit Boards; OSH Park, Lake Oswego, OR) to create an inductor-capacitor (LC) circuit pattern (FIG. 14A). Instead of using a tangible or discrete capacitor (e.g., 626, 726, 826) to form an LC resonant circuit as described above, the pledget sensor circuit has no physical capacitor but can achieve electrical resonance by utilizing a simple planar inductor with inherent parasitic capacitance (Cp). FIG. 14B shows an equivalent circuit diagram of a resonant circuit 1410 including the planar inductor coil 1402. In some cases, a suture 1500 passing through the pledget 1600 can include a conductive material so that the conductive suture can act as antennas, as indicated in FIG. 14C, which shows the equivalent circuit diagram of another resonant circuit 1410' including the planar inductor coil 1402. Thermal fusion at 200° C. was utilized to embed the flexible circuit within the PLA pledget structure. All pledget components were designed with concentric holes 1602 to allow the suture 1500 to pass through the sensor 1600 (FIGS. 15A-15B and 16). Overall, the size of the fabricated pledget sensor 1600 in this specific example was 12 mm×6.5 mm×2.5 mm.

Although the depicted substrate 1400 includes only one inductor coil 1402 of a specific configuration, it is to be understood that the inductor coil 1402 can have different configurations. For example, the number of turns of the inductor coil 1402 can be less than or more than 7 turns. As another example, the resonant circuit 1410 (or 1410') can comprise a stack of two or more inductor coils 1402 disposed on and/or attached to the substrate 1400.

As shown in FIGS. 15A-15B, the pledget sensor 1600 has a sensor body 1610 and a resonant circuit 1410 (or 1410') embedded within the sensor body 1610. The suture 1500 can be connected to the sensor body 1610. Similar to other resonant circuits described above, the resonant circuit 1410 (or 1410') is configured to electrically resonate at a resonant frequency when exposed to a first electromagnetic field and to emit a second remotely detectable electromagnetic field. A deformation of the sensor body 1610 in response to a tensile force applied by the suture 1500 is configured to change a resonant parameter of the resonant circuit 1410 (or 1410') in response to the deformation.

As described herein, the deformation of the sensor body 1610 includes bending, elongation, compression, rotation, torsion, or flexion of at least a portion of the sensor body 1610. Similar to the suture buttons, suture button assemblies, and suture anchors described above, for the pledget sensor 1600, the resonant parameter can include a resonant frequency, a resonant quality factor, or a real impedance magnitude of the resonant circuit 1410 (or 1410').

In some examples, the pledget sensor 1600 can include a case 1604 enclosing the sensor body 1610. In some examples, the case 1604 can comprise meshes of polylactic acid, polyglycolic acid, polycaprolactone, or the combinations thereof.

As shown in FIGS. 15A-15B, the sensor body 1610 can include a top portion 1612, a base portion 1614, and one or more legs 1616 connecting the top portion 1612 to the base portion 1614. The top portion 1612 can include a first layer 1618 and a second layer 1620. The resonant circuit 1410 (or 1410') can be disposed between the first layer 1618 and the second layer 1620. In some examples, the resonant circuit 1410 (or 1410') can be printed on a substrate (e.g., 1400) that is sandwiched between the first layer 1618 and the second layer 1620. In some examples, the resonant circuit 1410 (or 1410') can be printed directly on the first layer 1618 or the second layer 1620. In certain examples, the substrate 1400 is embedded within the sensor body 1610. In certain examples, the substrate 1400 can be deemed as a part of the sensor body 1610. In certain examples, the sensor body 1610 itself can be the substrate to which the resonant circuit 1410 (or 1410') is coupled.

In some examples, the sensor body 1610 comprise a biodegradable material, such as polylactic acid, polyglycolic acid, polycaprolactone, and any combination thereof. In some examples, the substrate 1400 can also be configured to be biodegradable. For example, the inductor coil 1402 can comprise a biocompatible and biodegradable material, such as zinc, magnesium, or the combination thereof. Thus, after implantation in a body tissue, the sensor body 1610 and the substrate 1400 can gradually decompose over time.

In certain examples, the base portion 1614 can further include a conductive layer or another resonant circuit (not shown), which can enhance or amplify the electrical resonance of the resonant circuit 1410 (or 1410'). In certain examples, such conductive layer can also be configured to be biocompatible and biodegradable. For example, such conductive layer can comprise any one of zinc, magnesium, a semiconductor, and iron oxide, or the combination thereof.

The sensor body 1610 can have a coupling mechanism configured to receive the suture 1500. In the depicted example, the coupling mechanism comprises a plurality of apertures 1602 (e.g., two apertures on the top portion 1612 and two apertures on the base portions 1614), through which the suture 1500 can loop around at least a portion of the sensor body 1610. Although not shown, the coupling mechanism can take a variety of other forms. For example, the coupling mechanism can include a hook configured to receive the suture 1500. In another example, the coupling mechanism can include a clamping member configured to receive the suture 1500. In still another example, the coupling mechanism can include a knot formed by the suture 1500 (e.g., the suture 1500 can form a knot and is directly tied to the sensor body 1610). In yet another example, the suture 1500 can be fixedly attached to the sensor body 1610 via an adhesive (e.g., glue, etc.).

In some examples, the coupling mechanism can extend through both the top portion 1612 and the base portion 1614 (e.g., the apertures 1602 in FIGS. 15A-15B). In some examples, the coupling mechanism (e.g., the hook, knot, adhesive, etc.) can be located at a top surface of the top portion 1612, or at a bottom surface of the top portion 1612, or at a side of the top portion 1612.

In certain examples, the sensor body 1610 can comprise a radiopaque material (e.g., iodine, barium, tantalum, bismuth, etc.) so that the pledget sensor 1600 can be viewable/traceable via fluoroscopy, and facilitate placement and/or alignment of a detection device, which is described further below.

As described above, the resonant circuit 1410 (or 1410') includes the inductor coil 1402. The resonant frequency of the resonant circuit 1410 (or 1410') is determined at least by an inductance of the inductor coil and an inherent parasitic capacitance (Cp) of the inductor coil 1402. In some examples, the deformation of the sensor body 1610 (e.g., by applying a tensile force to the suture 1500) is configured to change the inductance of the inductor coil 1402. In some examples, the deformation of the sensor body 1610 (e.g., by applying a tensile force to the suture 1500) is configured to change the parasitic capacitance (Cp). In some examples, the deformation of the sensor body 1610 (e.g., by applying a tensile force to the suture 1500) is configured to change both the inductance of the inductor coil 1402 and the parasitic capacitance (Cp).

In some examples, the resonant circuit 1410 (or 1410') can be one of a plurality of resonant circuits embedded at different locations within the sensor body 1610. The plurality of resonant circuits can be configured differently, e.g., to have different inductance and/or parasitic capacitance (Cp), so that each resonant circuit has a distinct resonant frequency. Thus, multiple measurements of the tensile force of the suture 1500 can be obtained by sweeping a frequency range (by a detection device). Based on locations of the resonant circuit, these multiple measurements can be analyzed (e.g., using average or weighted average, etc.) to more accurately determine the tensile force of the suture 1500.

It should be understood that the shape, size, and/or geometry of the pledget sensor 1600 can be altered to influence deformation behavior and therefore sensitivity and detection ranges of the resonant circuit. As non-exhaustive examples, FIGS. 24A-24E respectively depict five pledget sensors 2400A, 2400B, 2400C, 2400D, and 2400E, which have different body shapes.

Specifically, the pledge sensor 2400A has a generally rectangular sensor body 2410A, which has two opposing flat body surfaces: a top surface 2412A and a bottom surface 2414A. The pledge sensor 2400B has a curved sensor body 2410B, which have two rounded or arched body surfaces: an arched top surface 2412B and an arched bottom surface 2414B. The top and bottom surfaces 2412B and 2414B can have about the same curvature so that a vertical distance between the top and bottom surfaces 2412B and 2414B remains approximately constant throughout the sensor body 2410B. The pledge sensor 2400C has a sensor body 2410C, which has an arched top surface 2412C and a flat bottom surface 2414C such that a middle portion 2416C of the sensor body 2410C has a larger vertical dimension than two side portions 2418C of the sensor body 2410C. The pledge sensor 2400D has a sensor body 2410D that is similar to 2410C, e.g., including an arched top surface 2412D and a flat bottom surface 2414D, except that the curvature of the top surface 2412D is smaller than that of 2412C. Thus, while two side portions 2418D of the sensor body 2410D can have about the same dimension as 2410C, a middle portion 2416D of the sensor body 2410D has a smaller vertical dimension than 2416C. Finally, the pledge sensor 2400E also has a curved sensor body 2410E, which is defined by a curved top surface 2412E and a curved bottom surface 2414E. Unlike FIG. 24B where the top and bottom surfaces 2412B and 2414B are arched throughout the sensor body 2410B, in FIG. 24E, only a middle portion 2416E of the sensor body 2410E is arched, whereas two side portions 2418E of the sensor body 2410E are generally flat.

In certain examples, the suture 1500 can be deemed as a part of the pledget sensor 1600. In this case, the pledget sensor 1600 an also be referred to as a suture pledget. In other examples, the suture 1500 can be deemed as a component that is external (i.e., not part of) the pledget sensor 1600. In that case, the combination of the pledget sensor 1600 and the suture 1500 can also be referred to as a suture pledget.

As described above, suture 1500 can be conductive so that when connected to the sensor body 1610, the conductive suture 1500 can act as antennas connected to the resonant circuit 1410'. In certain examples, the suture 1500 can comprise a conductive polymer, which can include polyaniline, polypyrrole, polystyrene sulfonate, poly(3,4-ethylenedioxythiophene), or any combination thereof. In some examples, such conductive polymer can be coated at an outer surface of the suture 1500.

In certain examples, the suture 1500 can include a first suture and a second suture braided or coupled with the first suture. At least one of the first suture and the second suture can include a conductive material, such as the conductive polymer described above.

In certain examples, the suture 1500 can be biodegradable. For example, the suture 1500 can include poly (lactic-co-glycolic acid) and/or other biodegradable materials.

In certain examples, any of the pledget sensor disclosed herein can incorporate or be integrated with one or more other types of sensors, such as a temperature sensing unit, a pH sensing unit, an oxygen concentration sensing unit, a motion sensing unit (e.g., accelerometers, gyroscopes, etc.), etc.

Features of the pledget sensors described herein can also be incorporated into the suture buttons, suture button assemblies, and suture anchors described above. For example, components of the suture buttons, suture button assemblies, and suture anchors (e.g., enclosures, substrates, inductor coils, and/or sutures, etc.) can be configured to be biodegradable. As another example, sutures coupled to the suture buttons, suture button assemblies, and suture anchors can comprise a conductive layer so that the sutures can act as antennas. Additionally, discrete capacitors in the suture buttons, suture button assemblies, and suture anchors can be removed, while electrical resonance can still be achieved using inherent parasitic capacitance of one or more inductor coils.

Example Detection Device for Pledget Sensor

Specific examples of a detection system for the pledget sensor 1600 are described herein. Note that the detection system described herein can also be used for suture buttons, suture button assemblies, and/or suture anchors sensor described above.

Figure 17A:
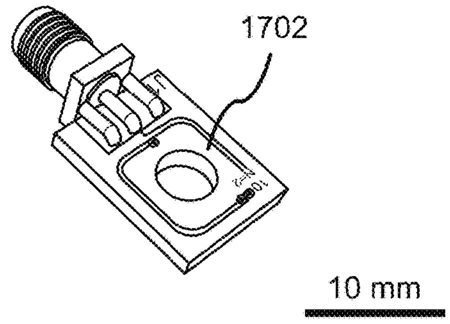
FIG. 17A depicts an example detection coil.
Figure 17B:
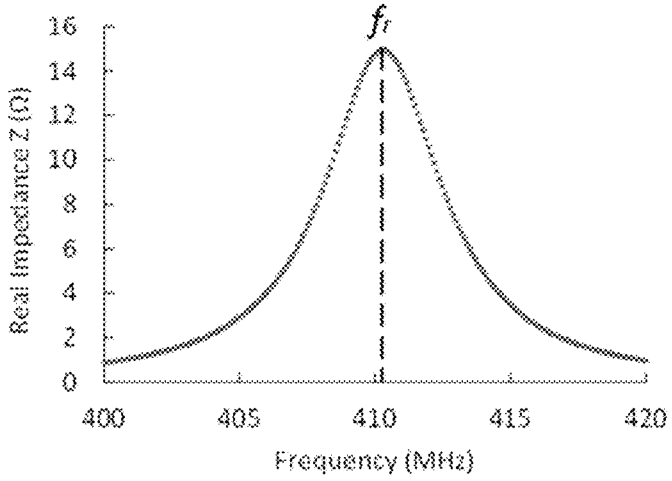
FIG. 17B depicts an example unloaded pledget sensor impedance spectrum showing resonance frequency ($f_r$) at 410.25 MHz.

To monitor resonance characteristics of the pledget sensor 1600, one specific external detection coil 1702 (also referred to as "coil antenna" or simply "antenna") was fabricated with a printed 2-turn planar inductor coil (OSH Park) approximately 10 mm in diameter (FIG. 17A). The detection coil 1702 can be configured to be placed over a body surface of a patient that is adjacent to a pledget sensor (e.g., 1600) implanted within the patient. Thus, this detection coil 1702 allowed electromagnetic coupling with the inductive component of the pledget sensor 1600 to enable wireless functionality. The pledget sensor's impedance spectrum can be generated by connecting the detection coil to an impedance analyzer, such as a network analyzer (E5061B ENA Vector Network Analyzer; Keysight, Santa Rosa, CA), which can produce a frequency-varying, alternating current electromagnetic field. In this specific example, the resonance frequency ($f_r$) of the unloaded pledget sensor 1600 was measured as 410.25 MHz as shown in the real part of the sensor's complex impedance spectrum (FIG. 17B).

Figure 17C:
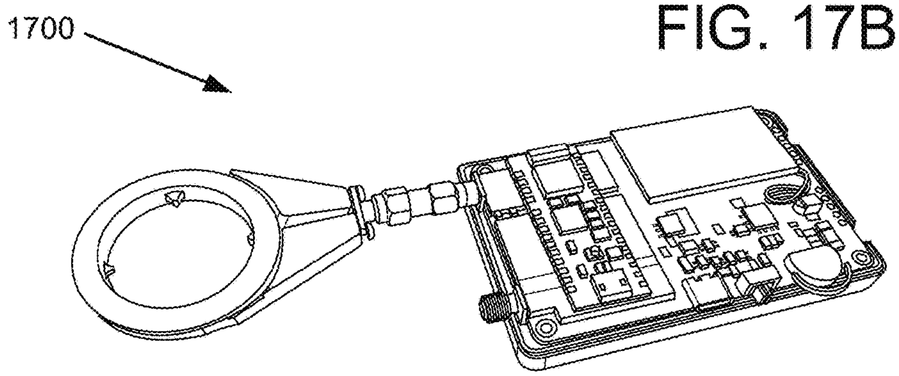
FIG. 17C depicts a protype of a detection device having a single coil.

In some examples, as depicted in FIG. 17C, a detection system 1700 can have a single coil (e.g., 1702) configured for both excitation (e.g., generating a first electromagnetic field to excite the pledget sensor 1600) and detection (e.g., detecting a second electromagnetic field emitted from the pledget sensor 1600). For example, the single coil can receive electrical current from the electronics. Sensor response can alter the reflected voltage to the coil. The change in the reflected voltage, measured as a function of frequency, can be used to determine the resonance characteristics of the pledget sensor 1600.

Figure 17D:
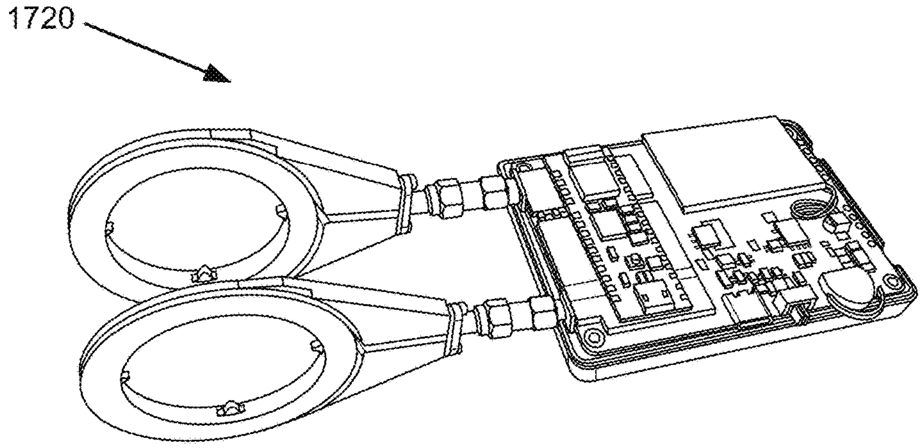
FIG. 17D depicts a protype of a detection device having dual coils.

In some examples, as depicted in FIG. 17D, a detection system 1720 can have dual coils (e.g., each can be configured as 1702) where one coil is used for excitation and another coil is used (as an antenna) for detection. In certain circumstances, having one coil for excitation and another coil for detection can improve signal detection ranges of the pledget sensor.

Similar to the detection devices described above with reference to FIGS. 1 and 3-5, each of the detection systems 1700 and 1720 can include an impedance analyzer (similar to 1020 in FIGS. 10-11) which is in electrical communication with a detection coil (e.g., 1702). Similarly, the impedance analyzer can be configured to generate a first electromagnetic field that causes a resonant circuit (e.g., 1410 or 1410') of the pledget sensor to resonate at a resonant frequency and emit a second electromagnetic field. The detection coil can detect the second electromagnetic field, and the impedance analyzer can be configured to measure a resonant parameter of the resonant circuit associated with a suture tension based on the detected second electromagnetic field. For example, the impedance analyzer can include a microcontroller (similar to 1060 of FIGS. 10-11) configured to sweep a frequency of the first electromagnetic field within a frequency spectrum. Similarly, the detection systems (e.g., 1700 and/or 1720) can be wearable, e.g., by having a wearable mount (e.g., similar to the ones shown in FIGS. 3-5) to which the detection coil and the impedance analyzer are attached. Likewise, the detection system (e.g., 1700, 1720) can further include a mobile computing unit (e.g., tablet computers or smart phones) in wireless communication with the impedance analyzer.

Example Simulation of Suture Pledget Loading

Figure 18:
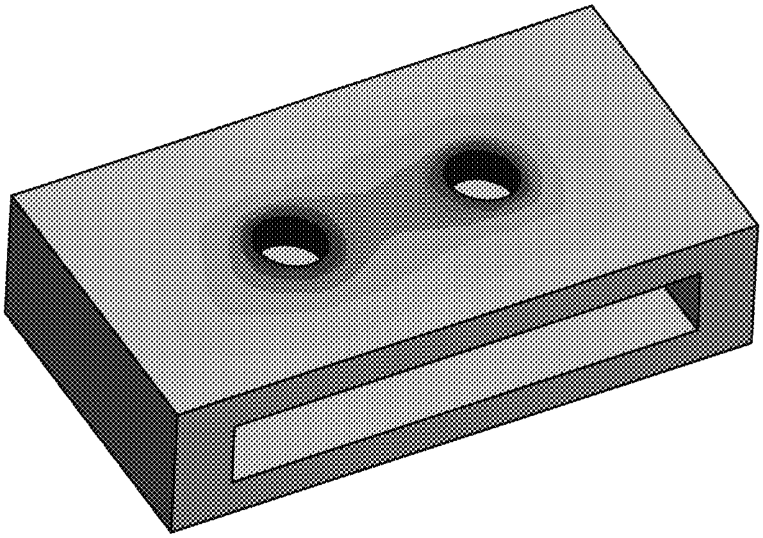
FIG. 18 depicts an example suture pledget mesh utilized in a finite element analysis (FEA) deformation study.

In one experimental study, deformation behavior of the pledget sensor 1600 was visualized with static structural simulations in finite element analysis (FEA) software (Ansys Workbench; Ansys, Canonsburg, PA). The PLA in the pledget structure was assumed to be linear elastic with a Young's modulus of 3.986 GPa and a Poisson's ratio of 0.332. Effects of the embedded flexible polyimide circuit substrate were not included in the simulations. Tetrahedral elements ranging from 0.1 mm to 0.5 mm in size were utilized in the pledget mesh, with the smaller element resolution near the deformation area of interest (FIG. 18). For deformation simulations, the bottom face of the pledget sensor 1600 was fixed while a 12 N force was applied to element faces beneath the suture loop passing through the pledget sensor 1600.

Figure 19:
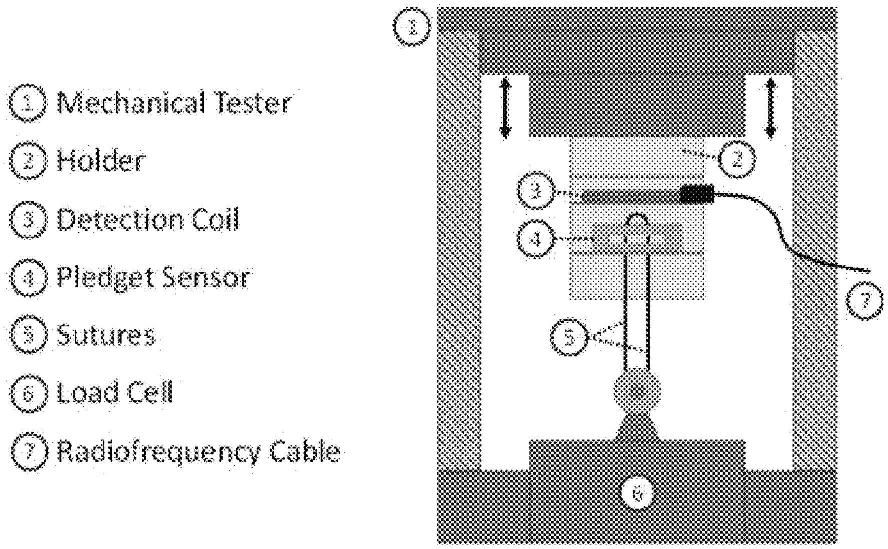
FIG. 19 schematically depicts an example mechanical testing system setup for suture pledget sensor loading studies.

To assess characteristics of the pledget sensor 1600, tensile loading studies were performed with a mechanical testing system (ElectroForce 3200; TA Instruments, New Castle, DE) and a custom 3D printed holder (Clear Resin; Formlabs, Somerville, MA) (FIG. 19). All loading studies used United States Pharmacopeia size #2 polyester braided sutures (Medtronic, Minneapolis, Minnesota). A 110% prestress was exerted on the pledget sensor 1600 before loading studies were performed to minimize any plastic deformation effects. Ramped loads varying from 2-12 N by a step of 2 N were applied to the pledget sensor 1600 to characterize sensitivity while hysteresis was evaluated by comparing sensor response during both loading and unloading conditions. Drift was then assessed with repeated loading from 2 to 12 N for 4 cycles. For all mechanical testing experiments, sensor resonance frequency was measured as a function of loading and each data point was collected within 10 seconds of applied loading.

Example Detection Distance Measurements

In one study, attenuation of the electronic signature of the pledget sensor 1600 through tissue mimics was tested by using synthetic gelatin sheets (Clear Ballistics, Fort Smith, AR) of varying thickness (2-16 mm). The gelatin tissue mimics were placed between the pledget sensor 1600 and detection coil whereafter subsequent signal amplitude measurements were completed.

Example Simulation Results of Pledget Deformation

Bending of the circuit pattern embedded in the pledget sensor 1600 alters the parasitic capacitance of the LC resonant circuit and therefore the measured resonance frequency during force transduction. Since the pledget sensor 1600 relies on flexion of the circuit pattern or substrate 1400 to determine suture force loading, pledget deformation dictates load sensing characteristics of the platform. Therefore, any design modifications that affect sensor bending of the pledget sensor 1600 can alter the sensitivity and detection range of the sensor. Some examples of how to modify pledget flexion include changing the aspect ratio of the pledget sensor, sheet thickness, leg height, leg thickness, and hole separation distance of the pledget design. For example, if the width of the pledget sensor is kept constant while increasing the sensor length by 200%, the force-sensing range will decrease by the power of 3, which is only about 12.5% of the original sensitivity range. If the length of the pledget sensor is kept constant while increasing the width by 200%, the force sensing range will increase by 200% as well. Changing the thickness of the pledget sensor should behave similarly to the behavior observed when changing the width of the pledget sensor.

Figure 20A:
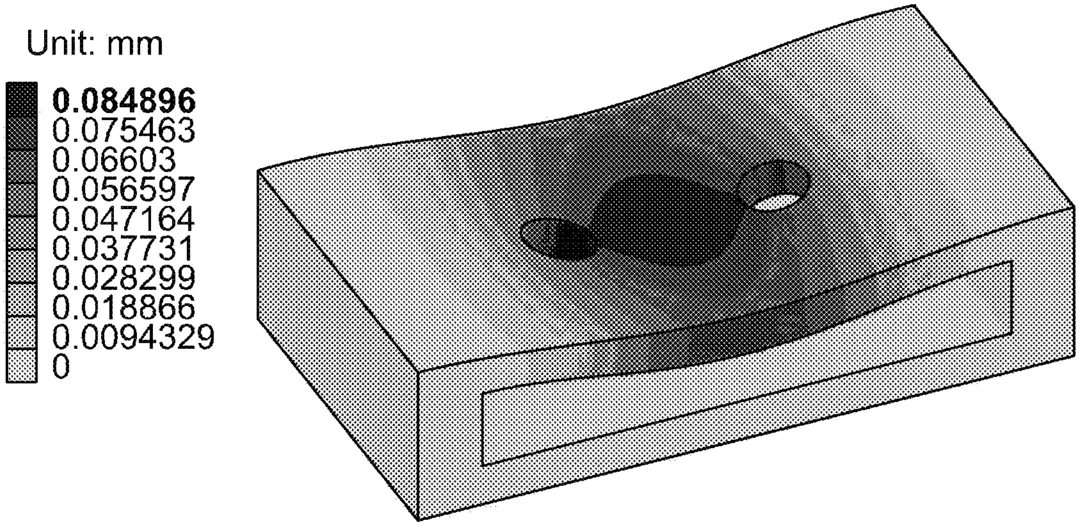
FIG. 20A depicts deformation of a suture pledget under loading from an example FEA study.
Figure 20B:
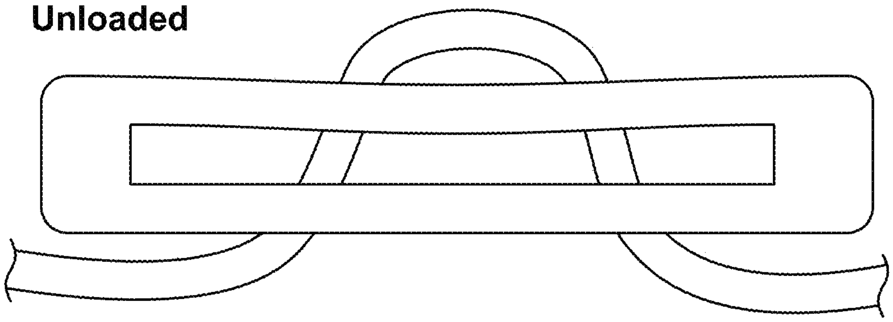
FIG. 20B depicts a side view of the suture pledget sensor deformation of FIG. 7A under an unloaded condition.
Figure 20C:
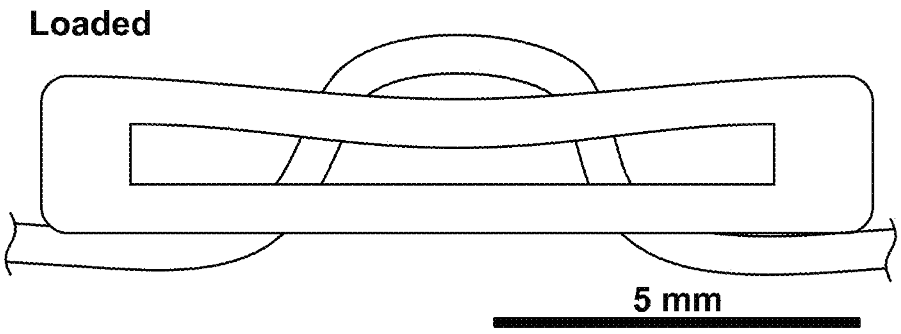
FIG. 20C depicts a side view of the suture pledget sensor deformation of FIG. 7A under a loaded condition.

Example pledget deformation simulation results showed pledget bending behavior under 12 N of loading (FIG. 20A). Greatest deformation occurred in the area where the loaded suture is adjacent to the upper face of the pledget, and deformation gradually decreased when approaching the leg attachment regions. A suture threaded thru a pledget prototype also demonstrated visible pledget deformation with applied tension (FIGS. 20B and 20C). Overall, the device design was able to achieve bending of the pledget's upper sheet containing the circuit pattern in response to suture loading.

Example Results on Pledget Sensor Suture Tension Detection

The resonance frequency of the unloaded pledget sensor 1600 (410 MHz) was within the ultra-high band (300 MHz to 3 GHz) of the radiofrequency spectra. If needed, the resonance frequency of the pledget sensor 1600 can be raised or lowered by changing the number of turns, trace spacing, and line thickness of the spiral inductor. For example, if the number of turns of the planar inductor is increased from 6 to 7, the resonance frequency is expected to be reduced from 480 MHz to about 410 MHz as resonance frequency is inversely proportional to the number of turns. If the tracing spacing of the planar inductor is reduced, the resonance frequency will also decrease as the parasitic capacitance is increased. The exact relationship between tracing space and resonance frequency can be determined through numerical simulations and/or actual experimental measurements. Line thickness of the planar inductor may have less of an effect on the resonance frequency but will indirectly affect the dimensions of the sensor since increasing the thickness of trace lines leads to larger sensors, which reduces the resonance frequency.

Figure 21:
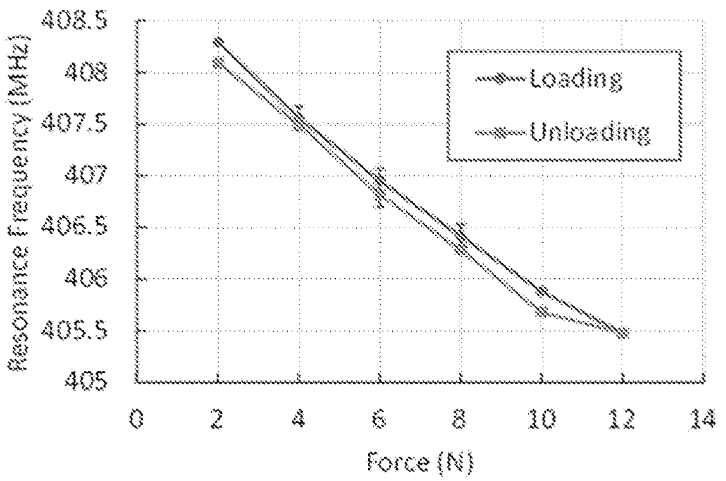
FIG. 21 depicts change in sensor resonance frequency during loading (circles) and unloading (squares), according to one example. Error bars represent standard deviation (n=3).
Figure 22:
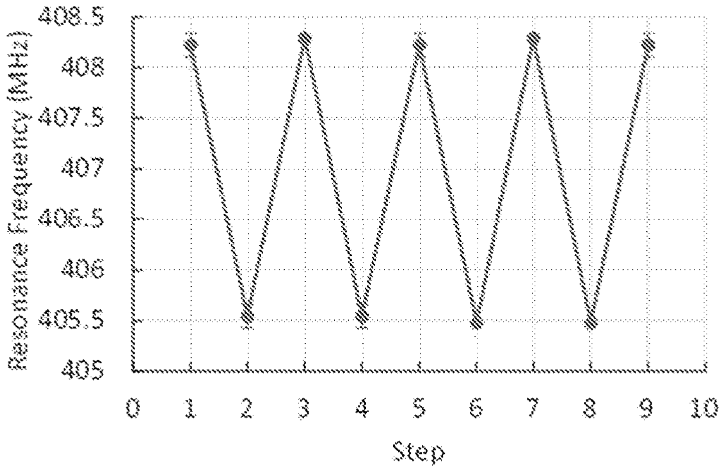
FIG. 22 depicts sensor resonance frequency under repetitive loading from 2 N (408.25±0.04 MHz) to 12 N (405.51±0.04 MHz), according to one example. Error bars represent standard deviation (n=3).

In one study, mechanical testing of the pledget sensor 1600 indicated that suture loading and unloading between 2 to 12 N was linearly related to changes in sensor resonance frequency (FIG. 21). Specifically, the sensitivity of the pledget sensor was 0.248 MHz/N and the full-scale output (FSO) of the sensor was 2.814 MHz for the tested loading range. Hysteresis associated with loading and unloading conditions of the pledget sensor did not exceed 7% of the FSO. Hysteresis was consistently the greatest between unloading and loading conditions at 10 N likely due to plastic deformation of the pledget material occurring during maximum force loading (12 N). In this specific study, loading magnitudes were lower than the forces experienced by some human connective tissues including the Achilles tendon or anterior cruciate ligament (ACL). Thus, the pledget sensor 1600 described in this particular example is more suitable for tissues including flexor tendons in the hand that experience 2.9 N to 8.8 N of tensile loading during passive and active motion respectively. However, with modifications to the pledget sensor design and material composition, the platform may be adapted to accommodate for greater loading ranges. An example modification is to change the composition of the sensor substrate material, which alters the elastic modulus of the material. By increasing the elastic modulus of the material, the loading range will increase since more force will be needed to create the same amount of deformation. For example, if the elastic modulus is increased by 200%, the force sensing range will increase by the same amount for the same sensor design. Further mechanical testing indicated that repetitive loading of the pledget sensor 1600 from 2 to 12 did not produce any drift or change in sensitivity over 4 cycles of recurring loads demonstrating the repeatability of platform (FIG. 22). This result is significant because maintaining sensor performance with cyclic loading is vital in the suturing of tissues that experience repetitive motion such as tendons and ligaments. In summary, these loading experiments showed the ability of the pledget design to transduce and quantify changes in suture loading.

Example Results on Pledget Sensor Detection Distance

Figure 23:
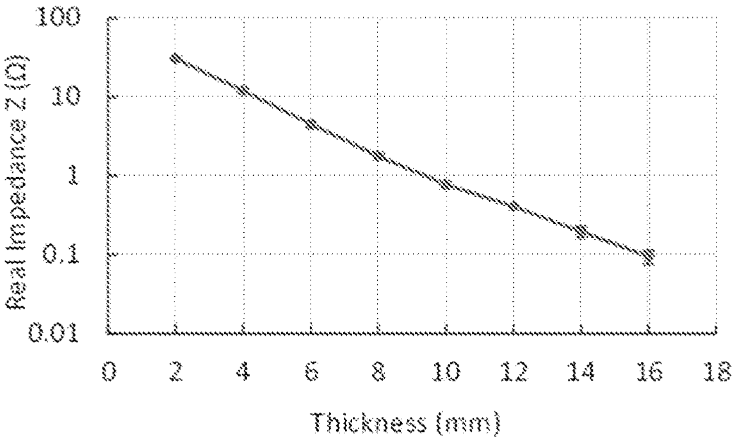
FIG. 23 depicts sensor impedance at the resonance frequency as a function of tissue mimic thickness, according to one example. Error bars represent standard deviation (n=3).
Figure 24A:
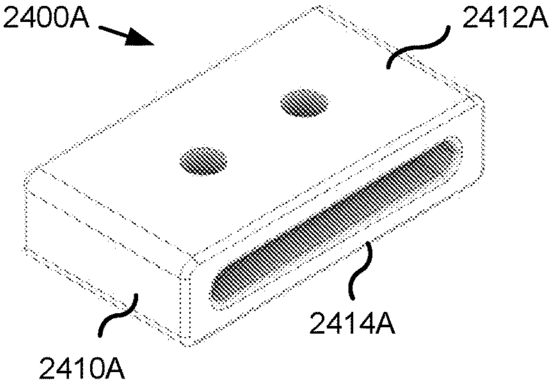
FIG. 24A-24E depict five example sensor body shapes.
Figure 24B:
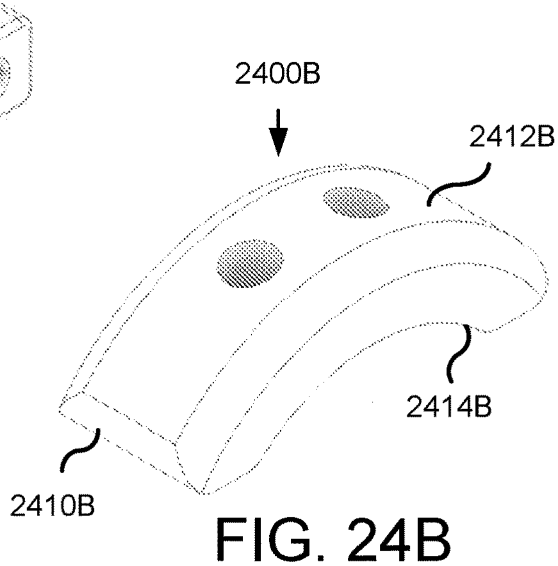
Figure 24C:
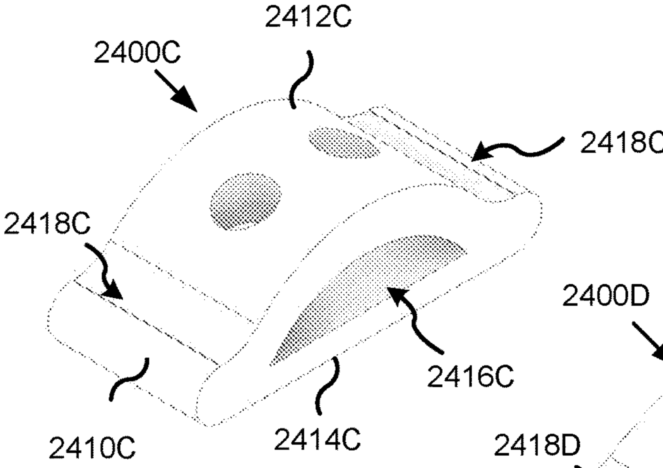
Figure 24D:
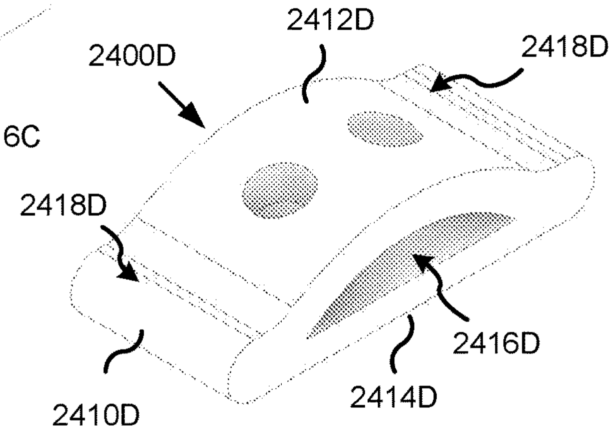
Figure 24E:
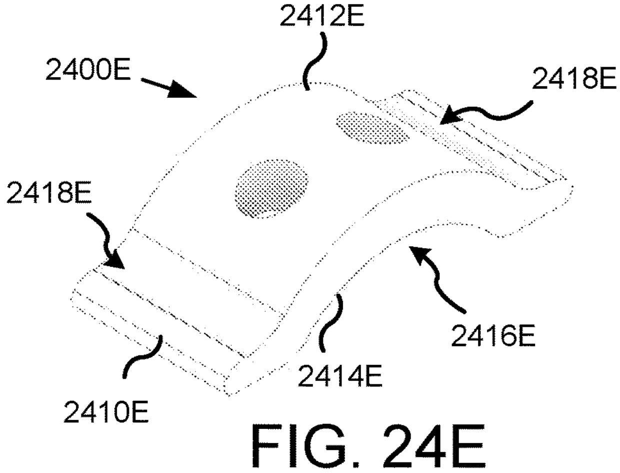

One important design consideration with wireless, implantable biosensors is ensuring remote communication can be maintained when passing through body tissues (i.e., skin, fat, muscle, etc.). In one study, detection distance of the pledget sensor 1600 evaluated with the use of varying thickness tissue mimics indicated a logarithmic relationship between tissue thickness and measured sensor impedance magnitude (FIG. 23). Tissue thickness superficial to tendons and ligaments within the human body is highly location specific. The maximum thickness tested (16 cm) reduced sensor impedance amplitude to 0.1Ω, restricting the current design to more superficial repair applications. Transmission depth limitations could be improved by stacking multiple inductor circuits within the sensor, optimizing detection coil design, and increasing the power output form the detection device. Additionally, by rendering the suture material conductive, sutures can be used as antennas to increase the electromagnetic coupling of the pledget sensor.

Example Applications of the Pledget Sensor

As described above, an example suture pledget sensor 1600 was engineered and characterized to demonstrate functionality in quantifying suture loading. Tracking suture loading during surgical recovery exercises could help physical therapists make more informed, less speculative treatment decisions on the intensity and duration of rehabilitation regimes for patients. Evidence-based care enabled by this transformative technology could ideally allow patients to resume their normal activity levels earlier and athletes to return to peak performance after injury more quickly by preventing tendon and ligament reinjury while optimizing patient recovery during physical therapy. This sensor technology can also provide patients biofeedback with visual targets and ranges during independent, at-home rehabilitation exercises. Additionally, decreased force measured by the pledget sensor over time could be an indicator of tissue bridging or healing since it is expected that tissues will begin bearing loading with regeneration. This wound healing metric could further aid physical therapists in making treatment decisions when patients can return to their typical physical activity levels.

As described above, the sensor pledget 1600 described herein can be configured to be fully biodegradable by using bioresorbable metals and polymers. Advantages of a degradable sensor include eliminating potentially cytotoxic circuit components and the need for secondary surgeries associated with device removal where complications such as additional patient anesthesia risks, the potential for surgical infection, further scarring at the surgical site, and interruption of the healing process could occur.

Additionally, the disclosed technology can increase transmission distance capabilities of the pledget sensor through the modification of the external excitation and detection system designs. Further, the exterior circuitry can be integrated into a wearable device that can be used during physical therapy exercises.

Example Computing Systems

Figure 25:
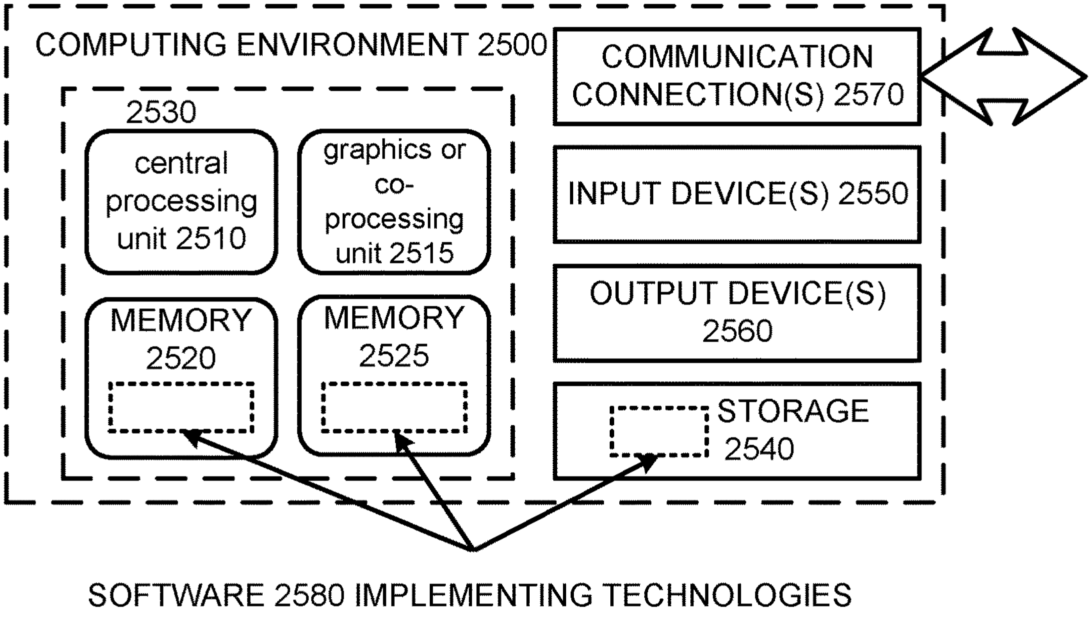
FIG. 25 is a block diagram of an example computing system in which described examples can be implemented.

FIG. 25 depicts an example of a suitable computing system 2500 in which the described innovations can be implemented. For example, the computing system 2500 can be used as the impedance analyzer 180 respectively depicted in FIGS. 3B, 4B, 5A, and/or the microcontroller 1060 depicted in FIGS. 10-11. The computing system 2500 is not intended to suggest any limitation as to scope of use or functionality of the present disclosure, as the innovations can be implemented in diverse computing systems.

With reference to FIG. 25, the computing system 2500 includes one or more processing units 2510, 2515 and memory 2520, 2525. In FIG. 25, this basic configuration 2530 is included within a dashed line. The processing units 2510, 2515 execute computer-executable instructions, such as for implementing the features described in the examples herein. A processing unit can be a general-purpose central processing unit (CPU), processor in an application-specific integrated circuit (ASIC), or any other type of processor. In a multi-processing system, multiple processing units execute computer-executable instructions to increase processing power. For example, FIG. 25 shows a central processing unit 2510 as well as a graphics processing unit or co-processing unit 2515. The tangible memory 2520, 2525 can be volatile memory (e.g., registers, cache, RAM), non-volatile memory (e.g., ROM, EEPROM, flash memory, etc.), or some combination of the two, accessible by the processing unit(s) 2510, 2515. The memory 2520, 2525 stores software 2580 implementing one or more innovations described herein, in the form of computer-executable instructions suitable for execution by the processing unit(s) 2510, 2515.

A computing system 2500 can have additional features. For example, the computing system 2500 includes storage 2540, one or more input devices 2550, one or more output devices 2560, and one or more communication connections 2570, including input devices, output devices, and communication connections for interacting with a user. An interconnection mechanism (not shown) such as a bus, controller, or network interconnects the components of the computing system 2500. Typically, operating system software (not shown) provides an operating environment for other software executing in the computing system 2500, and coordinates activities of the components of the computing system 2500.

The tangible storage 2540 can be removable or non-removable, and includes magnetic disks, magnetic tapes or cassettes, CD-ROMs, DVDs, or any other medium which can be used to store information in a non-transitory way and which can be accessed within the computing system 2500. The storage 2540 stores instructions for the software implementing one or more innovations described herein.

The input device(s) 2550 can be an input device such as a keyboard, mouse, pen, or trackball, a voice input device, a scanning device, touch device (e.g., touchpad, display, or the like) or another device that provides input to the computing system 2500. The output device(s) 2560 can be a display, printer, speaker, CD-writer, or another device that provides output from the computing system 2500.

The communication connection(s) 2570 enable communication over a communication medium to another computing entity (e.g., the server 190 depicted in FIG. 1). The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

The innovations can be described in the context of computer-executable instructions, such as those included in program modules, being executed in a computing system on a target real or virtual processor (e.g., which is ultimately executed on one or more hardware processors). Generally, program modules or components include routines, programs, libraries, objects, classes, components, data structures, etc. that perform particular tasks or implement particular abstract data types. The functionality of the program modules can be combined or split between program modules as desired in various examples. Computer-executable instructions for program modules can be executed within a local or distributed computing system.

For the sake of presentation, the detailed description uses terms like "determine" and "use" to describe computer operations in a computing system. These terms are high-level descriptions for operations performed by a computer, and should not be confused with acts performed by a human being. The actual computer operations corresponding to these terms vary depending on implementation.

Example Computer-Readable Media

Any of the computer-readable media herein can be non-transitory (e.g., volatile memory such as DRAM or SRAM, nonvolatile memory such as magnetic storage, can be implemented by storing in one or more computer-readable media (e.g., computer-readable storage media or other tangible media). Any of the things (e.g., data created and used during implementation) described as stored can be stored in one or more computer-readable media (e.g., computer-readable storage media or other tangible media). Computer-readable media can be limited to implementations not consisting of a signal.

Any of the methods described herein can be implemented by computer-executable instructions in (e.g., stored on, encoded on, or the like) one or more computer-readable media (e.g., computer-readable storage media or other tangible media) or one or more computer-readable storage devices (e.g., memory, magnetic storage, optical storage, or the like). Such instructions can cause a computing device to perform the method. The technologies described herein can be implemented in a variety of programming languages.

Example Cloud Computing Environment

Figure 26:
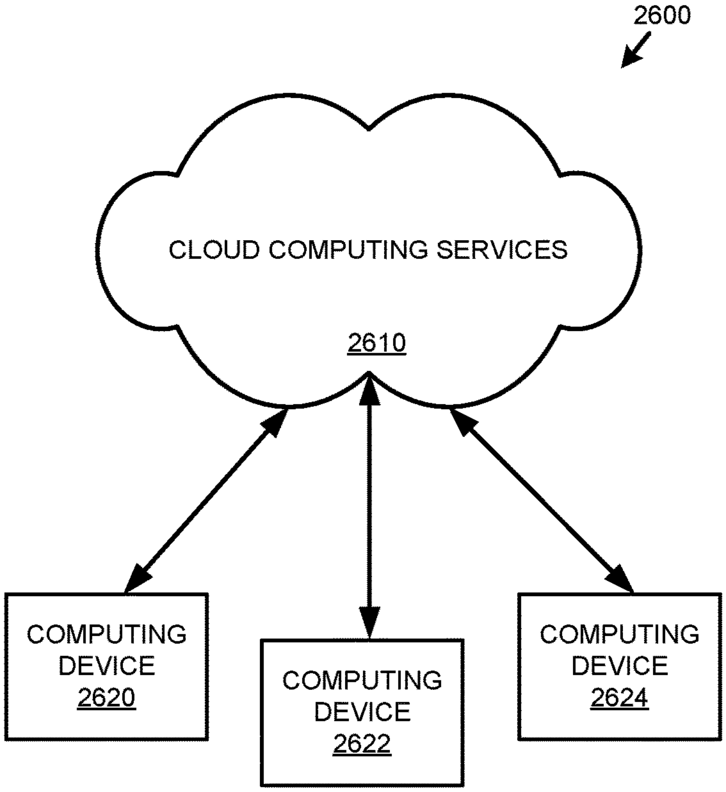
FIG. 26 is a block diagram of an example cloud computing environment that can be used in conjunction with the technologies described herein.

FIG. 26 depicts an example cloud computing environment 2600 in which the described technologies can be implemented, including, e.g., the system disclosed above and other systems herein. In certain examples, the cloud computing environment 2600 can be used to allow remote control and monitoring of implantable sensors described herein. For example, through the cloud computing environment 2600 (e.g., including the server 190 and/or gateway 192), an operator can remotely program the frequency, amplitude, and/or other parameters that control the excitation electromagnetic field generated by the detector 160, and/or remotely monitor the tensile force applied to the suture 140 connected to the sensor 110.

The cloud computing environment 2600 comprises cloud computing services 2610. The cloud computing services 2610 can comprise various types of cloud computing resources, such as computer servers, data storage repositories, networking resources, etc. The cloud computing services 2610 can be centrally located (e.g., provided by a data center of a business or organization) or distributed (e.g., provided by various computing resources located at different locations, such as different data centers and/or located in different cities or countries).

The cloud computing services 2610 are utilized by various types of computing devices (e.g., client computing devices), such as computing devices 2620, 2622, and 2623. For example, the computing devices (e.g., 2620, 2622, and 2624) can be computers (e.g., desktop or laptop computers), mobile devices (e.g., tablet computers or smart phones), or other types of computing devices. For example, the computing devices (e.g., 2620, 2622, and 2624) can utilize the cloud computing services 2610 to perform computing operations (e.g., data processing, data storage, and the like).

In practice, cloud-based, on-premises-based, or hybrid scenarios can be supported.

Example Implementations

Although the operations of some of the disclosed methods are described in a particular, sequential order for convenient presentation, such manner of description encompasses rearrangement, unless a particular ordering is required by specific language set forth herein. For example, operations described sequentially can in some cases be rearranged or performed concurrently.

Example Embodiments

Any of the following example embodiments can be implemented:

Embodiment 1. An implantable sensor, comprising:

a sensor body configured to connect to a suture; and a resonant circuit embedded within the sensor body, wherein the resonant circuit is configured to electrically resonate at a resonant frequency when exposed to a first electromagnetic field and to emit a second remotely detectable electromagnetic field;

wherein a deformation of the sensor body in response to a tensile force applied by the suture is configured to change a resonant parameter of the resonant circuit in response to the deformation.

Embodiment 2. The implantable sensor of embodiment 1, wherein the sensor body comprises a biodegradable material.

Embodiment 3. The implantable sensor of embodiment 2, wherein the biodegradable material comprises any one of polylactic acid, polyglycolic acid, polycaprolactone, and any combination thereof.

Embodiment 4. The implantable sensor of any one of embodiments 1-3, wherein the sensor body comprises a top portion, a base portion, and one or more legs connecting the top portion to the base portion.

Embodiment 5. The implantable sensor of embodiment 4, wherein the top portion comprises a first layer and a second layer, wherein the resonant circuit is disposed between the first layer and the second layer.

Embodiment 6. The implantable sensor of embodiment 5, wherein the resonant circuit is printed on a substrate sandwiched between the first layer and the second layer.

Embodiment 7. The implantable sensor of embodiment 6, wherein the substrate is biodegradable.

Embodiment 8. The implantable sensor of embodiment 5, wherein the resonant circuit is printed directly on the first layer or the second layer.

Embodiment 9. The implantable sensor of any one of embodiments 4-8, wherein the base portion comprises a conductive layer or another resonant circuit.

Embodiment 10. The implantable sensor of embodiment 9, wherein the conductive layer is biodegradable.

Embodiment 11. The implantable sensor of any one of embodiments 9-10, wherein the conductive layer comprises any one of zinc, magnesium, a semiconductor, and iron oxide, or the combination thereof.

Embodiment 12. The implantable sensor of any one of embodiments 4-11, wherein the sensor body comprises a coupling mechanism configured to receive the suture.

Embodiment 13. The implantable sensor of embodiment 12, wherein the coupling mechanism comprises at least two apertures through which the suture can loop around at least a portion of the sensor body.

Embodiment 14. The implantable sensor of any one of embodiments 12-13, wherein the coupling mechanism comprises a hook configured to receive the suture.

Embodiment 15. The implantable sensor of any one of embodiments 12-14, wherein the coupling mechanism comprises a clamping member.

Embodiment 16. The implantable sensor of any one of embodiments 12-15, wherein the coupling mechanism comprises a knot formed by the suture.

Embodiment 17. The implantable sensor of any one of embodiments 12-16, wherein the coupling mechanism comprises an adhesive.

Embodiment 18. The implantable sensor of any one of embodiments 12-17, wherein the coupling mechanism is located at a top surface of the top portion.

Embodiment 19. The implantable sensor of any one of embodiments 12-17, wherein the coupling mechanism is located at a bottom surface of the top portion.

Embodiment 20. The implantable sensor of any one of embodiments 12-17, wherein the coupling mechanism is located at a side of the top portion.

Embodiment 21. The implantable sensor of any one of embodiments 1-20, wherein the resonant circuit comprises an inductor coil, wherein the resonant frequency of the resonant circuit is determined at least by an inductance of the inductor coil and an inherent parasitic capacitance of the inductor coil.

Embodiment 22. The implantable sensor of embodiment 21, wherein the inductor coil is biodegradable.

Embodiment 23. The implantable sensor of embodiment 22, wherein the inductor coil comprises zinc, magnesium, or the combination thereof.

Embodiment 24. The implantable sensor of any one of embodiments 21-23, wherein the deformation of the sensor body is configured to change the inductance of the inductor coil.

Embodiment 25. The implantable sensor of any one of embodiments 21-24, wherein the deformation of the sensor body is configured to change the parasitic capacitance.

Embodiment 26. The implantable sensor of any one of embodiments 1-25, wherein the sensor body comprises a radiopaque material.

Embodiment 27. The implantable sensor of any one of embodiments 1-26, wherein the sensor body has a rectangular shape with two opposing flat body surfaces.

Embodiment 28. The implantable sensor of any one of embodiments 1-26, wherein the sensor body has at least one rounded body surface.

Embodiment 29. The implantable sensor of embodiment 28, wherein the sensor body has two opposing first and second body surfaces, wherein the first body surface is flat and the second body surface is rounded.

Embodiment 30. The implantable sensor of embodiment 28, wherein the sensor body has two opposing first and second body surfaces, wherein both the first and body surfaces are rounded.

Embodiment 31. The implantable sensor of any one of embodiments 1-30, wherein the deformation of the sensor body comprises bending, elongation, compression, rotation, torsion, or flexion of at least a portion of the sensor body.

Embodiment 32. The implantable sensor of any one of embodiments 1-31, wherein the resonant circuit comprises a stack of two or more inductor coils.

Embodiment 33. The implantable sensor of any one of embodiments 1-32, wherein the resonant parameter comprises a resonant frequency, a resonant quality factor, or a real impedance magnitude of the resonant circuit.

Embodiment 34. The implantable sensor of any one of embodiments 1-33, further comprising a case enclosing the sensor body, wherein the case comprises meshes of polylactic acid, polyglycolic acid, polycaprolactone, or the combinations thereof.

Embodiment 35. The implantable sensor of any one of embodiments 1-34, further comprising the suture connected to the sensor body.

Embodiment 36. The implantable sensor of embodiment 35, wherein the suture comprises a conductive polymer.

Embodiment 37. The implantable sensor of embodiment 36, wherein the suture is configured as an antenna connected to the resonant circuit.

Embodiment 38. The implantable sensor of any one of embodiments 36-37, wherein the conductive polymer comprises polyaniline, polypyrrole, poly(3,4-ethylenedioxythiophene), or polystyrene sulfonate.

Embodiment 39. The implantable sensor of any one of embodiments 36-38, wherein the conductive polymer is coated at an outer surface of the suture.

Embodiment 40. The implantable sensor of any one of embodiments 35-38, wherein the suture comprises a first suture and a second suture braided or coupled with the first suture, wherein at least one of the first suture and the second suture comprises a conductive material.

Embodiment 41. The implantable sensor of any one of embodiments 35-38, wherein the suture is biodegradable.

Embodiment 42. The implantable sensor of embodiment 41, wherein the suture comprises poly (lactic-co-glycolic acid).

Embodiment 43. The implantable sensor of any one of embodiments 1-42, wherein the resonant circuit is one of a plurality of resonant circuits embedded within the sensor body.

Embodiment 44. The implantable sensor of any one of embodiments 1-43, further comprising a temperature sensing unit coupled to the sensor body.

Embodiment 45. A device, comprising:

at least one antenna configured to be placed over a body surface of a patient that is adjacent to an implanted sensor; and an impedance analyzer which is in electrical communication with the at least one antenna;

wherein the impedance analyzer is configured to generate a first electromagnetic field that causes a resonant circuit of the implanted sensor to resonate at a resonant frequency and emit a second electromagnetic field;

wherein the at least one antenna is configured to detect the second electromagnetic field, wherein the impedance analyzer is configured to measure a resonant parameter of the resonant circuit associated with a suture tension based on the detected second electromagnetic field.

Embodiment 46. The device of embodiment 46, further comprising a wearable mount configured to be worn by the patient, wherein the antenna and the impedance analyzer are attached to the wearable mount.

Embodiment 47. The device of any one of embodiments 45-46, wherein the at least one antenna comprises a single coil antenna configured to both transmit the first electromagnetic field and detect the second electromagnetic field.

Embodiment 48. The device of any one of embodiments 45-46, wherein the at least one antenna comprises a first coil antenna and a second coil antenna, wherein the first coil antenna is configured to transmit the first electromagnetic field, wherein the second coil antenna is configured to detect the second electromagnetic field.

Embodiment 49. The device of any one of embodiments 45-48, further comprising a microcontroller configured to sweep a frequency of the first electromagnetic field within a frequency spectrum.

Embodiment 50. The device of any one of embodiments 45-49, further comprising a mobile computing unit in wireless communication with the impedance analyzer.

Embodiment 51. A system, comprising:

an implantable sensor configured to be implanted inside a body of a patient; and a detector located outside the body of the patient and configured to wirelessly communicate with the implantable sensor;

wherein the implantable sensor is any one of the implantable sensors of embodiments 1-44.

Embodiment 52. The system of embodiment 51, wherein the detector is any one of the devices of embodiments 45-50.

Embodiment 53. A method of fabricating an implantable sensor, the method comprising:

embedding a resonant circuit within a sensor body, wherein the resonant circuit and the sensor body are any of the respective resonant circuits and sensor bodies of embodiments 1-44.

Embodiment 54. A method, comprising:

generating a first electromagnetic field with an interrogation source, wherein the first electromagnetic field produces a resonance at a resonant frequency in a resonant circuit of a sensor wirelessly spaced apart from the interrogation source and causes the sensor to emit a second electromagnetic field, wherein the sensor comprises a resonant circuit embedded within a sensor body, wherein the sensor body is configured to deform in response to a tensile force applied by a suture, wherein the deformation of the sensor body is configured to change a resonant parameter of the resonant circuit; and detecting the second electromagnetic field and measuring the resonant parameter of the resonant circuit based on the detected second electromagnetic field.

Embodiment 55. The method of embodiment 54, wherein the sensor is any one of the implantable sensors of embodiments 1-44.

Embodiment 56. The method of any one of embodiments 54-55, further comprising affixing the suture to the sensor body.

Embodiment 57. The method of any one of embodiments 54-56, wherein the interrogation source is any one of the devices of embodiments 45-50.

Embodiment 58. The method of any one of embodiments 54-57, further comprising controlling a degradation rate of the sensor.

Embodiment 59. The method of embodiment 58, wherein controlling the degradation rate comprises defining copolymer composition ratios and polymer molecular weight for polymer constituents of the sensor.

Embodiment 60. The method of any one of embodiments 58-59, wherein controlling the degradation rate comprises defining alloying compositions ratios for metal constituents of the sensor.

Embodiment 61. The method of any one of embodiments 58-60, wherein controlling the degradation rate comprises applying a focused ultrasound to heat the sensor.

Embodiment 62. The method of any one of embodiments 54-61 further comprising rendering the suture conductive.

Embodiment 63. The method of embodiment 62, wherein rendering the suture conductive comprises embedding a conductive polymer within the suture.

Embodiment 64. The method of any one of embodiments 62-63, wherein rendering the suture conductive comprises coating the suture with a conductive polymer.

Embodiment 65. The method of any one of embodiments 62-64, wherein rendering the suture conductive comprises braiding or coupling another conductive wire with the suture.

Embodiment 66. The method of any one of embodiments 54-65, further comprising compensating plastic deformation of a substrate of the sensor.

Embodiment 67. The method of any one of embodiments 54-66, further comprising compensating environmental conditions of the sensor.

Embodiment 68. The method of any one of embodiments 54-67, further comprising generating one or more calibration curves for the sensor.

Embodiment 69. The method of any one of embodiments 54-68, further comprising determining a suture tension based on the measured resonant parameter.

Embodiment 70. The method of embodiment 69, further comprising calculating a healing parameter based on the suture tension, wherein the healing parameter indicates a status of tissue bridging around the sensor.

Embodiment 71. An implantable sensor, comprising:

a sensor assembly configured to connect to a suture, wherein the sensor assembly includes a substrate and a resonant circuit coupled to the substrate;

wherein the resonant circuit is configured to electrically resonate at a resonant frequency when exposed to a first electromagnetic field and to emit a second remotely detectable electromagnetic field;

wherein the substrate is configured to deform in response to a tensile force applied by the suture and to change a resonant parameter of the resonant circuit in response to the deformation.

Embodiment 72. The implantable sensor of embodiment 71, wherein the resonant circuit comprises at least one inductor connected to at least one capacitor, wherein the resonant frequency of the resonant circuit is determined at least by an inductance of the at least one inductor and a capacitance of the at least one capacitor.

Embodiment 73. The implantable sensor of embodiment 72, wherein the deformation of the substrate comprises an elongation of at least a portion of the substrate.

Embodiment 74. The implantable sensor of embodiment 72, wherein the deformation of the substrate comprises a compression of at least a portion of the substrate.

Embodiment 75. The implantable sensor of embodiment 72, wherein the deformation of the substrate comprises a bending or a torsion of at least a portion of the substrate.

Embodiment 76. The implantable sensor of any one of embodiments 72-75, wherein the deformation of the substrate is configured to change the capacitance of the at least one capacitor, thereby causing a change of the resonant frequency of the resonant circuit.

Embodiment 77. The implantable sensor of any one of embodiments 72-76, wherein the deformation of the substrate is configured to change the inductance of the at least one inductor, thereby causing a change of the resonant frequency of the resonant circuit.

Embodiment 78. The implantable sensor of any of embodiments 72-77, wherein the resonant circuit further comprises a resistive transducer having a resistance that varies in response to a deformation of the resistive transducer caused by the deformation of the substrate.

Embodiment 79. The implantable sensor of embodiment 78, wherein the resistive transducer is electrically connected to the at least one inductor and the at least one capacitor in series.

Embodiment 80. The implantable sensor of any one of embodiments 78-79, wherein the lowest resistance of the resistive transducer when it is deformed is at least 10 times more than a conductor resistance of the resonant circuit.

Embodiment 81. The implantable sensor of any one of embodiments 72-80, wherein the at least one inductor comprises a planar spiral coil.

Embodiment 82. The implantable sensor of any one of embodiments 72-81, wherein the at least one capacitor comprises a parallel plate capacitor or an interdigital capacitor.

Embodiment 83. The implantable sensor of any one of embodiments 72-82, wherein the resonant circuit comprises two or more inductors that are connected in series.

Embodiment 84. The implantable sensor of any one of embodiments 72-83, wherein the resonant circuit comprises two or more inductors that are connected in parallel.

Embodiment 85. The implantable sensor of any one of embodiments 72-84, wherein the resonant circuit comprises two or more capacitors that are connected in series.

Embodiment 86. The implantable sensor of any one of embodiments 72-85, wherein the resonant circuit comprises two or more capacitors that are connected in parallel.

Embodiment 87. The implantable sensor of any one of embodiments 72-86, wherein the at least one inductor is a first inductor, wherein the resonant circuit further comprises a second inductor that is connected to the at least one capacitor in parallel.

Embodiment 88. The implantable sensor of any one of embodiments 72-87, wherein the at least one capacitor is a first capacitor, wherein the resonant circuit further comprises a second capacitor that is connected to the at least one inductor in parallel.

Embodiment 89. The implantable sensor of any one of the embodiments 71-88, wherein the resonant parameter of the resonant circuit comprises the resonant frequency of the resonant circuit.

Embodiment 90. The implantable sensor of any one of the embodiments 71-89, wherein the resonant parameter of the resonant circuit comprises a resonance quality factor of the resonant circuit.

Embodiment 91. The implantable sensor of any one of embodiments 71-90, wherein the substrate comprises an enclosure enclosing the resonant circuit, wherein the enclosure comprises a biocompatible material.

Embodiment 92. The implantable sensor of any one of embodiments 71-91, further comprising one or more other resonant circuits, wherein the resonant circuit and the one or more other resonant circuits have different respective resonant frequencies when exposed to the first electromagnetic field.

Embodiment 93. The implantable sensor of embodiments 92, wherein the resonant circuit and the one or more other resonant circuits are coupled to the same substrate.

Embodiment 94. The implantable sensor of embodiment 93, wherein the resonant circuit and the one or more other resonant circuits are configured to change respective resonant frequencies in response to the same deformation of the substrate.

Embodiment 95. The implantable sensor of embodiment 92, wherein the resonant circuit and at least one of the other resonant circuits are configured to change respective resonant frequencies in response to different deformations of the substrate.

Embodiment 96. The implantable sensor of embodiment 95, wherein the different deformations of the substrate are along different axes of the substrate.

Embodiment 97. The implantable sensor of embodiments 92, wherein at least one of the other resonant circuits is coupled to another substrate that is different from the substrate, wherein the other substrate is configured to deform in response to the tensile force applied by the suture.

Embodiment 98. The implantable sensor of embodiment 97, wherein the substrate and the other substrate are configured to deform in the same direction in response to the tensile force applied by the suture.

Embodiment 99. The implantable sensor of embodiments 98, wherein the substrate and the other substrate are configured to deform to different extents in response to the tensile force applied by the suture.

Embodiment 100. The implantable sensor of embodiments 97, wherein the substrate and the other substrate are configured to deform in different directions in response to the tensile force applied by the suture.

Embodiment 101. The implantable sensor of any of embodiments 72-100, wherein the deformation of the substrate is configured to change the inductance of the at least one inductor and/or the capacitance of the at least one capacitor, thereby changing the resonant frequency of the resonant circuit.

Embodiment 102. The implantable sensor of embodiment 101, wherein the at least one inductor is fixedly attached to the substrate such that deformation of the substrate causes a corresponding dimensional change of the at least one inductor, thereby changing the inductance of the at least one inductor.

Embodiment 103. The implantable sensor of embodiment 102, wherein the substrate comprises a spring.

Embodiment 104. The implantable sensor of any one of embodiments 102-103, wherein the deformation of the substrate is configured to cause an elongation of the at least one inductor.

Embodiment 105. The implantable sensor of any one of embodiments 102-103, wherein the deformation of the substrate is configured to cause a compression of the at least one inductor.

Embodiment 106. The implantable sensor of any one of embodiments 101-105, wherein the at least one capacitor comprises two conductive plates and the substrate comprises a compliant layer situated between the two conductive plates.

Embodiment 107. The implantable sensor of embodiment 106, wherein the deformation of the substrate is configured to decrease a distance between the two conductive plates, thereby increasing the capacitance of the at least one capacitor.

Embodiment 108. The implantable sensor of embodiment 106, wherein the deformation of the substrate is configured to increase a distance between the two conductive plates, thereby decreasing the capacitance of the at least one capacitor.

Embodiment 109. The implantable sensor of any one of embodiments 106-108, wherein the at least one inductor is disposed adjacent to one of the two conductive plates.

Embodiment 110. The implantable sensor of embodiment 109, wherein the resonant circuit comprises two inductors respectively disposed adjacent to the two conductive plates.

Embodiment 111. The implantable sensor of any of embodiments 72-100, wherein the resonant circuit comprises a resistive transducer having a resistance that varies in response to the deformation;

wherein the resonant circuit has a resonance quality factor determined at least by an inductance of the at least one inductor, a capacitance of the at least one capacitor, and the resistance of the resistive transducer;

wherein the deformation of the substrate is configured to deform the resistive transducer, thereby changing the resistance of the resistive transducer and the resonance quality factor of the resonant circuit.

Embodiment 112. The implantable sensor of embodiment 111, wherein the resistive transducer is fixedly attached to the substrate such that deformation of the substrate causes a corresponding deformation of the resistive transducer.

Embodiment 113. The implantable sensor of embodiment 112, wherein the substrate comprises a spring.

Embodiment 114. The implantable sensor of any of embodiments 111-113, wherein the deformation of the substrate is configured to increase the resistance of the resistive transducer.

Embodiment 115. The implantable sensor of any of embodiments 111-113, wherein the deformation of the substrate is configured to decrease the resistance of the resistive transducer.

Embodiment 116. The implantable sensor of any of embodiments 111-115, wherein the resistive transducer is oriented relative to the substrate such that the resistive transducer is deformed substantially in the same direction as the tensile force applied by the suture.

Embodiment 117. The implantable sensor of any of embodiments 111-115, wherein the resistive transducer is oriented relative to the substrate such that the resistive transducer is deformed in a direction that forms an oblique angle relative to a direction of the tensile force applied by the suture.

Embodiment 118. The implantable sensor of any of embodiments 111-117, wherein the deformation of the substrate is configured to change the capacitance of the at least one capacitor and/or the inductance of the at least one inductor.

Embodiment 119. The implantable sensor of any of embodiments 111-117, wherein the inductance of the at least one inductor is configured to remain constant when the substrate is deformed.

Embodiment 120. The implantable sensor of any of embodiments 111-117 and 119, wherein the capacitance of the at least one capacitor is configured to remain constant when the substrate is deformed.

Embodiment 121. The implantable sensor of embodiment 71, wherein the substrate comprises an enclosure enclosing the resonant circuit;

wherein the resonant circuit comprises at least one inductor and at least one capacitor, wherein the resonant circuit has a resonant frequency determined at least by an inductance of the at least one inductor and a capacitance of the at least one capacitor;

wherein the enclosure is configured to deform in response to the tensile force applied by the suture;

wherein the deformation of the enclosure is configured to change the inductance of the at least one inductor and/or the capacitance of the at least one capacitor, thereby changing the resonant frequency of the resonant circuit.

Embodiment 122. The implantable sensor of embodiment 121, wherein the deformation of the enclosure is configured to elongate or compress the at least one inductor, thereby changing the inductance of the at least one inductor.

Embodiment 123. The implantable sensor of embodiment 122, wherein the substrate comprises an inductor holder disposed inside the enclosure, wherein the at least one inductor is fixedly attached to the inductor holder, wherein the deformation of the enclosure is configured to deform the inductor holder.

Embodiment 124. The implantable sensor of any one of embodiments 121-123, wherein the at least one capacitor comprises two parallel conductive plates.

Embodiment 125. The implantable sensor of embodiment 124, wherein the deformation of the enclosure is configured to press the two parallel conductive plates toward each other.

Embodiment 126. The implantable sensor of embodiment 124, wherein the deformation of the enclosure is configured to pull the two parallel conductive plates away from each other.

Embodiment 127. The implantable sensor of any one of embodiments 121-126, wherein the enclosure comprises a suture retaining member configured to retain a portion of the suture.

Embodiment 128. The implantable sensor of any one of embodiments 121-127, wherein the enclosure comprises a first cover and a second cover, wherein the resonant circuit is sandwiched between the first and second covers, wherein the suture extends across at least a portion of the first cover.

Embodiment 129. The implantable sensor of embodiment 128, wherein when a portion of the suture is connected to a biological tissue, the second cover of the enclosure is located closer to the biological tissue than the first cover of the enclosure.

Embodiment 130. The implantable sensor of embodiment 128, wherein when a portion of the suture is connected to a biological tissue, the first cover of the enclosure is located closer to the biological tissue than the second cover of the enclosure.

Embodiment 131. The implantable sensor of embodiment 71, wherein the substrate comprises an enclosure enclosing the resonant circuit;

wherein the resonant circuit comprises at least one inductor, at least one capacitor, and a resistive transducer having a resistance that varies in response to the deformation;

wherein the resonant circuit has a resonance quality factor determined at least by an inductance of the at least one inductor, a capacitance of the at least one capacitor, and the resistance of the resistive transducer;

wherein the enclosure is configured to deform in response to the tensile force applied by the suture; wherein the deformation of the enclosure is configured to deform the resistive transducer, thereby changing the resistance of the resistive transducer and the resonance quality factor of the resonant circuit.

Embodiment 132. The implantable sensor of embodiment 131, wherein the at least one inductor, the at least one capacitor, and the resistive transducer are connected in series.

Embodiment 133. The implantable sensor of any one of embodiments 131-132, further comprising a frame to which the resistive transducer is fixedly attached, wherein the deformation of the enclosure is configured to deform the frame, thereby deforming the resistive transducer attached thereto.

Embodiment 134. The implantable sensor of embodiment 133, wherein the frame comprises stainless-steel, titanium, or an alloy of two or more materials selected from the group consisting of iron, cobalt, chromium, titanium, and tantalum.

Embodiment 135. The implantable sensor of any one of embodiments 133-134, wherein the enclosure comprises parallel first cover and second cover, wherein the frame is sandwiched between and generally parallel to the first and second covers.

Embodiment 136. The implantable sensor of embodiment 135, wherein the at least one inductor is disposed on the first cover.

Embodiment 137. The implantable sensor of embodiment 136, wherein the at least one inductor is a first inductor, wherein the resonant circuit further comprises a second inductor disposed on the second cover, wherein the first and second inductors are connected in series.

Embodiment 138. The implantable sensor of any one of embodiments 133-137, wherein the resistive transducer is attached to a portion of the frame configured to receive a loop of the suture.

Embodiment 139. The implantable sensor of any one of embodiments 131-138, wherein the enclosure comprises one or more apertures through which the suture can extend and loop around at least a portion of the enclosure.

Embodiment 140. The implantable sensor of any one of embodiments 131-139, wherein the enclosure comprises one or more recesses through which the suture can extend and loop around at least a portion of the enclosure.

Embodiment 141. The implantable sensor of embodiment 71, wherein the resonant circuit comprises at least one inductor, at least one capacitor, and a resistive transducer having a resistance that varies in response to the deformation;

wherein the resonant circuit has a resonance quality factor determined at least by an inductance of the at least one inductor, a capacitance of the at least one capacitor, and the resistance of the resistive transducer;

wherein the deformation of the substrate is configured to deform the resistive transducer, thereby changing the resistance of the resistive transducer and the resonance quality factor of the resonant circuit.

Embodiment 142. The implantable sensor of embodiment 141, wherein the substrate comprises a spring to which the resistive transducer is fixedly attached.

Embodiment 143. The implantable sensor of embodiment 142, wherein the spring comprises an eyelet through which the suture can extend.

Embodiment 144. The implantable sensor of any one of embodiments 141-143, further comprising an enclosure, wherein the enclosure comprises a conic tip portion and a body portion connected to the tip portion, wherein the body portion has a cylindrical shape.

Embodiment 145. The implantable sensor of embodiment 144, wherein the body portion of the enclosure comprises a plurality of external threads.

Embodiment 146. The implantable sensor of any one of embodiments 144-145, wherein the substrate comprises an inductor holder enclosed by the body portion of the enclosure, wherein the at least one inductor wraps around the inductor holder.

Embodiment 147. The implantable sensor of embodiment 146, wherein the inductor holder comprises an inner lumen through which the suture can extend.

Embodiment 148. The implantable sensor of any one of embodiments 146-147, wherein the inductor holder is coaxial with the body portion of the enclosure.

Embodiment 149. The implantable sensor of any one of embodiments 144-148, wherein an end of the body portion opposite to the tip portion has a first aperture through which the suture can exit from the enclosure.

Embodiment 150. The implantable sensor of any one of embodiments 144-149, wherein the enclosure comprises a second aperture extending through a side wall of the body portion, thereby allowing access to the suture located inside the enclosure.

Embodiment 151. A device, comprising:

a coil antenna configured to be placed over a body surface portion of a patient that is adjacent to a medical implant; and an impedance analyzer which is in electrical communication with the coil antenna;

wherein the impedance analyzer is configured to generate a first electromagnetic field that causes a resonant circuit of the medical implant to resonate at a resonant frequency and emit a second electromagnetic field;

wherein the coil antenna is configured to detect the second electromagnetic field and the impedance analyzer is further configured to measure a resonant parameter of the resonant circuit associated with a suture tension based on the detected second electromagnetic field.

Embodiment 152. The device of embodiment 151, further comprising a wearable mount configured to be worn by the patient, wherein the coil antenna and the impedance analyzer are attached to the wearable mount.

Embodiment 153. The device of embodiment 152, wherein the wearable mount comprises a brace configured to wrap around a body part of the patient.

Embodiment 154. The device of any one of embodiments 152-153, wherein the wearable mount comprises an adhesive tape that can be attached to a skin of the patient.

Embodiment 155. The device of any one of embodiments 151-154, wherein the impedance analyzer comprises a signal generator, a gain and phase detector, and a microcontroller.

Embodiment 156. The device of embodiment 155, wherein the signal generator is configured to provide an excitation signal to the coil antenna, wherein the excitation signal is configured to generate the first electromagnetic field.

Embodiment 157. The device of embodiment 156, wherein the impedance analyzer further comprises an auto-balancing bridge configured to condition the excitation signal to the coil antenna.

Embodiment 158. The device of any one of embodiments 156-157, wherein the microcontroller is configured to modulate a frequency of the excitation signal so that the excitation signal can sweep a frequency spectrum that contains the resonant frequency of the resonant circuit of the medical implant.

Embodiment 159. The device of embodiment 158, wherein the gain and phase detector is configured to measure a magnitude response and a phase response over the frequency spectrum based on the detected second electromagnetic field.

Embodiment 160. The device of embodiment 159, wherein the microcontroller is configured to measure the resonant frequency of the resonant circuit based on the measured magnitude response over the frequency spectrum.

Embodiment 161. The device of embodiment 160, wherein the microcontroller is configured to measure a resonance quality factor of the resonant circuit based on the measured magnitude response over the frequency spectrum.

Embodiment 162. The device of any one of embodiments 151-161, wherein the impedance analyzer is configured to measure a tensile force applied to a suture connected to the medical implant based on the measured resonant parameter of the resonant circuit.

Embodiment 163. The device of embodiment 162, wherein the impedance analyzer comprises a computer readable media storing at least one calibration curve, wherein the impedance analyzer is configured to convert the measured resonant parameter of the resonant circuit to the measured tensile force applied by the suture based on the at least one calibration curve.

Embodiment 164. A system, comprising:

a medical implant configured to be implanted inside a body of a patient; and a detector located outside the body of the patient;

wherein the medical implant comprises a sensor and a suture connected to the sensor, wherein the sensor comprises a substrate and a resonant circuit coupled to the substrate, wherein a tensile force applied by the suture is configured to cause a deformation of the substrate which changes a resonant parameter of the resonant circuit;

wherein the detector is configured to wirelessly detect the change of the resonant parameter.

Embodiment 165. The system of embodiment 164, wherein the detection is further configured to measure the tensile force applied by the suture based on the detected change of the resonant parameter.

Embodiment 166. The system of any one of embodiments 164-165, wherein the detector is wearable or portable by the patient.

Embodiment 167. The system of any one of embodiments 164-166, further comprising a server station, wherein the detector is configured to wireless communicate with the server station.

Embodiment 168. The system of any one of embodiments 164-167, wherein the medical implant is any one of the implantable sensors of embodiments 71-150.

Embodiment 169. The system of any one of embodiments 164-168, wherein the detector is any one of the devices of embodiments 151-163.

Embodiment 170. A method of fabricating an implantable sensors, the method comprising:

coupling a resonant circuit to a substrate, wherein the resonant circuit and the substrate are any of the respective resonant circuits and substrates of embodiments 71-150.

Embodiment 171. A method of assembling a detection device, the method comprising:

connecting an impedance analyzer to a coil antenna, wherein the impedance analyzer and the coil antenna are any of the respective impedance analyzers and coil antennas of embodiments 151-163.

Embodiment 172. A method, comprising:

generating a first electromagnetic field with an interrogation source, wherein the first electromagnetic field produces a resonance at a resonant frequency in a resonant circuit of a sensor wirelessly spaced apart from the interrogation source and causes the sensor to emit a second electromagnetic field, wherein the sensor comprises a substrate and the resonant circuit is coupled to the substrate, wherein the substrate is configured to deform in response to a tensile force applied by a suture, wherein the deformation of the substrate is configured to change a resonant parameter of the resonant circuit; and detecting the second electromagnetic field and measuring the resonant parameter of the resonant circuit based on the detected second electromagnetic field.

Embodiment 173. The method of embodiment 172, wherein the sensor is any one of the implantable sensors of embodiments 71-150.

Embodiment 174. The method of any one of embodiments 172-173, further comprising attaching the suture to the substrate of the sensor.

Embodiment 175. The method of any one of embodiments 172-174, wherein the interrogation source is any one of the devices of embodiments 151-163.

Embodiment 176. The method of any one of embodiments 172-175, further comprising adjusting a position and/or orientation of the interrogation source to increase a sensitivity of the interrogation source.

Embodiment 177. The method of any one of embodiments 172-176, further comprising determining a suture tension based on the measured resonant parameter.

Embodiment 178. The method of embodiment 177, wherein the determining the suture tension comprises obtaining a calibration curve that characterizes a relationship between the resonant parameter of the resonant circuit and a tensile force applied to the suture.

Embodiment 179. The method of embodiment 178, wherein the determining the suture tension comprises converting the measured resonant parameter of the resonant circuit to a measured tensile force based on the calibration curve.

Embodiment 180. A system, comprising:

a detector configured to wirelessly detect a change of resonant parameter of a resonant circuit and measure a tensile force applied to a suture based on the detected change of the resonant parameter;

wherein the resonant circuit is coupled to a substrate;

wherein the tensile force applied to the suture is configured to cause a deformation of the substrate which changes the resonant parameter of the resonant circuit.

Embodiment 181. The system of embodiment 180, wherein the detector is any one of the devices of embodiments 151-163.

Embodiment 182. The system of any one of embodiments 180-181, further comprising a sensor comprising the resonant circuit and the substrate, wherein the sensor is any one of the implantable sensors of embodiments 71-150.

Embodiment 183. One or more computer-readable media having encoded thereon computer-executable instructions causing one or more processors to perform a method comprising:

generating a first electromagnetic field that causes a resonant circuit to resonate at a resonant frequency and emit a second electromagnetic field;

detecting the second electromagnetic field;

measuring a resonant parameter of the resonant circuit based on the detected second electromagnetic field; and converting the measured resonant parameter of the resonant circuit to a tensile force applied by a suture;

wherein the resonant circuit is coupled to a substrate;

wherein the substrate is configured to deform in response to the tensile force applied by the suture;

wherein the deformation of the substrate is configured to change the resonant parameter of the resonant circuit.

Embodiment 184. An assembly, comprising:

an adaptor configured to receive a suture button, wherein the adaptor comprises a substrate and a resonant circuit coupled to the substrate, wherein the substrate is configured to contact the suture button when the suture button is received by the adaptor, wherein the resonant circuit is configured to electrically resonate at a resonant frequency when exposed to a first electromagnetic field and to emit a second remotely detectable electromagnetic field;

wherein the substrate is configured to deform responsive to a deformation of the suture button, thereby changing a resonant parameter of the resonant circuit in response to the deformation of the substrate.

Embodiment 185. The assembly of embodiment 184 further comprising the suture button and a suture connected to the suture button.

Embodiment 186. The assembly of embodiment 185, wherein the suture button has no embedded electronics.

Embodiment 186. The assembly of any one of embodiments 184-186, wherein the substrate comprises a deformable member and the resonant circuit includes at least one strain gauge attached to the deformable member.

Example Alternatives

The technologies from any example can be combined with the technologies described in any one or more of the other examples. In view of the many possible examples to which the principles of the disclosed technology can be applied, it should be recognized that the illustrated embodiments are examples of the disclosed technology and should not be taken as a limitation on the scope of the disclosed technology. Rather, the scope of the claimed subject matter is defined by the following claims and their equivalents.

We claim:

1. An implantable sensor, comprising:

a sensor body configured to connect to a suture; and a resonant circuit embedded within the sensor body, wherein the resonant circuit is configured to electrically resonate at a resonant frequency when exposed to a first electromagnetic field and to emit a second remotely detectable electromagnetic field;

wherein a deformation of the sensor body in response to a tensile force applied by the suture is configured to change a parasitic capacitance of the resonant circuit in response to the deformation; and wherein the resonant frequency of the resonant circuit is determined at least in part by the change in parasitic capacitance.

2. The implantable sensor of claim 1, wherein the sensor body comprises a biodegradable material.

3. The implantable sensor of claim 1, wherein the sensor body comprises a top portion, a base portion, and one or more legs connecting the top portion to the base portion, wherein the top portion comprises a first layer and a second layer, wherein the resonant circuit is disposed between the first layer and the second layer.

4. The implantable sensor of claim 3, wherein the resonant circuit is printed on a substrate sandwiched between the first layer and the second layer, wherein the substrate is biodegradable.

5. The implantable sensor of claim 3, wherein the base portion comprises a conductive layer or another resonant circuit.

6. The implantable sensor of claim 5, wherein the conductive layer is biodegradable.

7. The implantable sensor of claim 1, wherein the sensor body comprises a coupling mechanism configured to receive the suture.

8. The implantable sensor of claim 1, further comprising the suture connected to the sensor body.

9. The implantable sensor of claim 8, wherein the suture comprises a conductive polymer.

10. An implantable sensor, comprising:

a sensor assembly configured to connect to a suture, wherein the sensor assembly includes a substrate and a resonant circuit coupled to the substrate;

wherein the resonant circuit is configured to electrically resonate at a resonant frequency when exposed to a first electromagnetic field and to emit a second remotely detectable electromagnetic field;

wherein the substrate is configured to deform in response to a tensile force applied by the suture and to change a parasitic capacitance of the resonant circuit in response to the deformation; and wherein the resonant frequency of the resonant circuit is determined at least in part by the change in parasitic capacitance.

11. The implantable sensor of claim 10, wherein the resonant circuit comprises at least one inductor, wherein the resonant frequency of the resonant circuit is determined at least by an inductance of the at least one inductor and the parasitic capacitance.

12. The implantable sensor of claim 11, wherein the resonant circuit further comprises a resistive transducer having a resistance that varies in response to a deformation of the resistive transducer caused by the deformation of the substrate.

13. The implantable sensor of claim 11, wherein the deformation of the substrate is configured to change the inductance of the at least one inductor or, thereby changing the resonant frequency of the resonant circuit.

14. The implantable sensor of claim 11, wherein the resonant circuit comprises a resistive transducer having a resistance that varies in response to the deformation;

wherein the resonant circuit has a resonance quality factor determined at least by an inductance of the at least one inductor, the parasitic capacitance, and the resistance of the resistive transducer;

wherein the deformation of the substrate is configured to deform the resistive transducer, thereby changing the resistance of the resistive transducer and the resonance quality factor of the resonant circuit.

15. The implantable sensor of claim 10, wherein the substrate comprises an enclosure enclosing the resonant circuit;

wherein the resonant circuit comprises at least one inductor, wherein the resonant circuit has a resonant frequency determined at least in part by an inductance of the at least one inductor and the parasitic capacitance;

wherein the enclosure is configured to deform in response to the tensile force applied by the suture;

wherein the deformation of the enclosure is configured to change the inductance of the at least one inductor and/or the parasitic capacitance, thereby changing the resonant frequency of the resonant circuit.

16. The implantable sensor of claim 10, wherein the substrate comprises an enclosure enclosing the resonant circuit;

wherein the resonant circuit comprises at least one inductor and a resistive transducer having a resistance that varies in response to the deformation;

wherein the resonant circuit has a resonance quality factor determined at least by an inductance of the at least one inductor, the parasitic capacitance, and the resistance of the resistive transducer;

wherein the enclosure is configured to deform in response to the tensile force applied by the suture;

wherein the deformation of the enclosure is configured to deform the resistive transducer, thereby changing the resistance of the resistive transducer and the resonance quality factor of the resonant circuit.

17. The implantable sensor of claim 10, wherein the resonant circuit comprises at least one inductor and a resistive transducer having a resistance that varies in response to the deformation;

wherein the resonant circuit has a resonance quality factor determined at least by an inductance of the at least one inductor, the parasitic capacitance, and the resistance of the resistive transducer;

wherein the deformation of the substrate is configured to deform the resistive transducer, thereby changing the resistance of the resistive transducer and the resonance quality factor of the resonant circuit.

18. A system, comprising:

a medical implant configured to be implanted inside a body of a patient; and a detector located outside the body of the patient;

wherein the medical implant comprises a sensor and a suture connected to the sensor, wherein the sensor comprises a substrate and a resonant circuit coupled to the substrate, wherein a tensile force applied by the suture is configured to cause a deformation of the substrate which changes a parasitic capacitance of the resonant circuit;

wherein the detector is configured to wirelessly detect the change of the parasitic capacitance.

* * * * *